United States Patent [19]

Nakamura et al.

[11] Patent Number: 5,068,340

[45] Date of Patent: Nov. 26, 1991

[54] ISOTHIAZOLYL SUBSTITUTED GLYCEROL DERIVATIVES CONTAINING PHOSPHATE GROUPS

[75] Inventors: Norio Nakamura; Hiroyuki Koike; Takeshi Oshima, all of Tokyo, Japan

[73] Assignee: Sankyo Company, Limited, Tokyo, Japan

[21] Appl. No.: 368,132

[22] Filed: Jun. 16, 1989

Related U.S. Application Data

[63] Continuation of Ser. No. 14,936, Feb. 13, 1987, abandoned.

[30] Foreign Application Priority Data

Feb. 13, 1986 [JP] Japan .................................. 61-29624

[51] Int. Cl.$^5$ ........................ C07F 9/09; C07F 9/6561
[52] U.S. Cl. ........................................ 548/119; 546/21
[58] Field of Search ............................ 548/119; 546/21

[56] References Cited

U.S. PATENT DOCUMENTS

| | | | |
|---|---|---|---|
| 4,408,052 | 10/1983 | Hozumi et al. | 546/22 |
| 4,794,183 | 12/1988 | Nakamura et al. | 546/22 |
| 4,891,363 | 1/1990 | Nakamura et al. | 514/94 |
| 4,921,865 | 5/1990 | Broquet et al. | 514/314 |

FOREIGN PATENT DOCUMENTS 0146258 6/1985 European Pat. Off. .
0157609 10/1985 European Pat. Off. .

OTHER PUBLICATIONS

N. Nakamura et al., "2-O-(3-Isoxazolyl) Glycerol Derivatives as PAF Agonists and Antagonists"; Third International Conference on Platelet-Activating Factor and Structurally Related Alkyl Ether Lipids, May 8–12, 1989, Tokyo, Japan, p. 96.

Upjohn, Abstract U-66985, *J. Biol. Chem.*, 260, 12710–12714 (1985).

*Research Communications in Chemical Pathology and Pharmacology*, 38, 3 et seq. (1982).

Nakamura et al., *Tetrahedron Letters,* 31, 699–702 (1990).

*Primary Examiner*—David B. Springer
*Attorney, Agent, or Firm*—Frishauf, Holtz, Goodman & Woodward

[57] ABSTRACT

Glycerol derivatives having at least one heterocyclic group on the 1 or 2 position are PAF antagonists which may be used to treat asthma, inflammation and shock.

13 Claims, No Drawings

ISOTHIAZOLYL SUBSTITUTED GLYCEROL DERIVATIVES CONTAINING PHOSPHATE GROUPS

The application is a continuation of application Ser. No. 07/014,936 filed Feb. 13, 1987.

BACKGROUND TO THE INVENTION

The present invention relates to a series of novel glycerol derivatives containing a heterocyclic system and provides processes for producing these compounds and compositions containing them for therapeutic use, especially for use as antagonists to platelet activating factor (hereinafter abbreviated, as is conventional, to "PAF").

Natural PAF, at least as isolated from mammalian tissues, is a mixture of from 2 to 5 phospholipids, the number depending upon the nature of the original tissue. The major constituents of PAF may be represented by the formula (A):

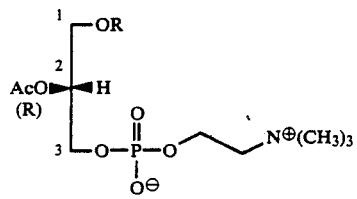

in which R represents a long chain aliphatic hydrocarbon group which may be saturated or unsaturated. Natural PAF is levorotatory and the various components of natural PAF may be identified, for example as: 1-$C_{16:0}$=formula (A) where R represents a hexadecyl group; 1-$C_{18:0}$=formula (A) where R represents an octadecyl group; 1-$C_{18:1}$=formula (A) where R represents a 9(Z)-octadecenyl group.

PAF exhibits a strong platelet activating and aggregating effect. It also has a hypotensive effect and increases vasopermeability; it is believed to be an active agent in the induction of the shock state (for example endotoxin-induced shock) and to act as a mediator of inflammatory disease. Accordingly, PAF antagonists have been investigated with a view to developing new types of anti-shock agent and of anti-inflammatory agent. Accordingly, analogs of natural PAF's have been investigated in an attempt to find such PAF antagonists. Currently, several compounds are known as PAF antagonists. For example, the compound of formula (B):

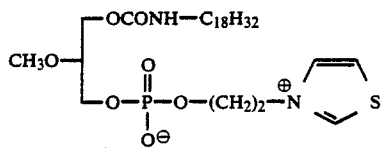

(also known as CV-3988) is disclosed in U.S. Pat. No. 4,408,052, whilst the compound of formula (C):

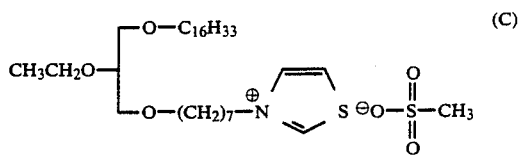

known as ONO-6240) is disclosed in European Patent Publication No. 146258. These compounds, however, are unsatisfactory for one or more of the following reasons: they lack sufficient intensity of antagonism towards PAF; the duration of their effect is insufficient; biological utilization is inadequate.

Other glycerol derivatives known to have PAF inhibitory activity are disclosed in EP Patent Publication No. 157,609, which discloses a series of glycerol derivatives for use as PAF inhibitors. Certain of the compounds disclosed therein have certain structural similarities to the compounds of the invention, although those compounds are said in that EP Specification not to be the preferred compounds. Those compounds of the EP Specification differ from the compounds of the present invention in that, where they have a heterocyclic group at the 2-position, they lack an intervening oxygen atom, which is an essential requirement of the compounds of the present invention.

We have now discovered a series of PAF antagonists which are glycerol derivatives containing a heterocyclic structure. The compounds of the present invention have been found to be excellent PAF antagonists, resulting in anti-asthmatic, anti-inflammatory and anti-shock activities which have excellent duration, bioavailability and level of activity.

BRIEF SUMMARY OF INVENTION

It is an object of the present invention to provide a series of novel compounds having excellent PAF antagonist activity.

It is a further object of the invention to provide methods and compositions for using such compounds in the treatment and prophylaxis of asthma, inflammation and the shock state.

It is a still further object of the invention to provide processes for producing such compounds.

The compounds of the invention are glycerol derivatives of formula (I):

in which:

$R^1$ represents a $C_8$–$C_{22}$ alkyl group, an alkylcarbamoyl group in which the alkyl part is $C_8$–$C_{22}$, a heterocyclic group having one $C_8$–$C_{22}$ alkyl substituent or a heterocyclic group having one $C_8$–$C_{22}$ alkyl substituent and at least one of substituents (a), defined below;

$R^2$ represents a $C_1$–$C_6$ alkyl group, a $C_1$–$C_6$ aliphatic acyl group, an aromatic acyl group, an aryl group, a $C_7$–$C_{14}$ aralkyl group, a heterocyclic group or a substituted heterocyclic group having at least one substituent selected from the group consisting of substituents (a), defined below;

Y represents an oxygen atom, a sulfur atom, a group of formula —$NR^3$—, a group of formula —X-

—CO—R$^4$—, a group of formula —R$^4$—CO—X—, a group of formula —NR$^3$—CO—, a group of formula —CO—NR$^3$— or a group of formula —X—P(O)(OH)—O—,
where:

R$^3$ represents a hydrogen atom, a C$_1$-C$_6$ alkyl group, a C$_1$-C$_6$ aliphatic acyl group, an aromatic acyl group, a C$_2$-C$_7$ alkoxycarbonyl group or a substituted C$_2$-C$_7$ alkoxycarbonyl group having at least one substituent selected from the group consisting of halogen atoms and trialkylsilyl groups where each alkyl part is C$_1$-C$_6$; and R$^4$ represents a direct bond or a group of formula —NR$^3$ where R$^3$ is as defined above; and X represents an oxygen atom or a sulfur atom;

D represents a C$_1$-C$_{14}$ alkylene group or a substituted C$_1$-C$_{14}$ alkylene group having one substituent selected from the group consisting of carboxy groups and protected carboxy groups;

Q represents a nitrogen-containing heterocyclic group containing at least one ring nitrogen atom and/or quaternary ring nitrogen atom, a substituted nitrogen-containing heterocyclic group containing at least one ring nitrogen atom and/or quaternary ring nitrogen atom, said substituted nitrogen-containing heterocyclic group having at least one substituent selected from the group consisting of substituents (b), a group of formula —NR$^5$R$^6$ or a group of formula —N$^+$R$^5$R$^6$R$^7$. Z$^-$;

where R$^5$, R$^6$ and R$^7$ are independently selected from the group consisting of hydrogen atoms and C$_1$-C$_6$ alkyl groups and Z$^-$ represents a pharmaceutically acceptable anion;

substituents (a):

C$_1$-C$_6$ alkyl groups. C$_1$-C$_6$ aliphatic acyl groups, aromatic acyl groups, aryl groups and C$_7$-C$_{14}$ aralkyl groups.

substituents (b):

C$_1$-C$_6$ alkyl groups, C$_1$-C$_6$ alkoxy groups, carbamoyl groups, halogen atoms and C$_1$-C$_6$ hydroxyalkyl groups, said aryl groups and the aryl parts of said aralkyl and aromatic acyl groups being C$_6$-C$_{10}$ carbocyclic aryl groups which are unsubstituted or have at least one substituent selected from the group consisting of substituents (c);

substituents (c):

C$_1$-C$_6$ alkyl groups; C$_1$-C$_6$ alkoxy groups; C$_1$-C$_6$ alkyl groups having at least one halogen substituent; halogen atoms; amino groups; C$_1$-C$_6$ alkylamino groups; dialkylamino groups in which each alkyl part is C$_1$-C$_6$; nitro groups; cyano groups; C$_1$-C$_6$ aliphatic acyl groups; aromatic acyl groups; aryl groups; C$_7$-C$_{14}$ aralkyl groups; carbamoyl groups; C$_1$-C$_6$ hydroxyalkyl groups; C$_2$-C$_7$ alkoxycarbonyl groups; substituted C$_2$-C$_7$ alkoxycarbonyl groups having at least one substituent selected from the group consisting of halogen atoms and trialkylsilyl groups where each alkyl part is C$_1$-C$_6$; groups of formula —CONR'$_2$ where R' represents a C$_1$-C$_6$ alkyl group or an aryl group; C$_1$-C$_4$ alkylenedioxy groups; hydroxy groups; heterocyclic groups; and substituted heterocyclic groups having at least one substituent selected from the group consisting of substituents (a) and substituents (b) defined above; and said heterocyclic groups and nitrogen-containing heterocyclic groups having from 5 to 11 ring atoms, of which from 1 to 3 are hetero-atoms selected from the group consisting of nitrogen, oxygen and sulfur hetero-atoms; provided that, when R$^1$ represents said alkyl or alkylcarbamoyl group R$^2$ represents said heterocyclic or substituted heterocyclic group; and pharmaceutically acceptable salts, esters and amides thereof.

The invention also provides a pharmaceutical composition for the treatment of inflammation or shock, comprising a PAF antagonist in combination with a pharmaceutically acceptable carrier or diluent, wherein the PAF antagonist is selected from the group consisting of compounds of formula (I) and pharmaceutically acceptable salts thereof.

The invention still further provides a method for the treatment or prophylaxis of asthma, inflammation or shock comprising administering an amount of a PAF antagonist to an animal (which may be a mammal, e.g. human) sufficient to effect treatment or prophylaxis of inflammation or shock, wherein said PAF antagonist is selected from the group consisting of compounds of formula (I) and pharmaceutically acceptable salts thereof.

DETAILED DESCRIPTION OF INVENTION

The compounds of the invention can exist in the form of an inner salt when Y represents a group of formula —X—P(O)(OH)—O— and Q represents a group containing an ammonio moiety. For example, such an inner salt may be a compound of formula (I), in which —Y—D—Q represents a group of formula (II):

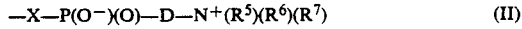
$$-X-P(O^-)(O)-D-N^+(R^5)(R^6)(R^7) \tag{II}$$

(in which D, X, R$^5$, R$^6$ and R$^7$ are as defined above) or it may exist in the form of a salt, in which —Y—D—Q represents a group of formula (IIa):

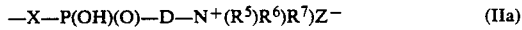
$$-X-P(OH)(O)-D-N^+(R^5)R^6)R^7)Z^- \tag{IIa}$$

(in which D, X, R$^5$, R$^6$ and R$^7$ are as defined above, and Z$^-$ represents a pharmaceutically acceptable anion, preferably a hydroxy group, a halogen atom, a C$_1$-C$_6$ alkylsulfonyloxy group, a C$_1$-C$_6$ haloalkylsulfonyloxy group or an arylsulfonyloxy group).

Where one of R$^5$, R$^6$ and R$^7$ (for example R$^7$) represents a hydrogen atom, the group of formula (II) which is represented by —Y—D—Q, may be represented by the following formula (IIb):

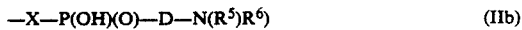
$$-X-P(OH)(O)-D-N(R^5)R^6) \tag{IIb}$$

(in which X, R$^5$, R$^6$ and D are as defined above) which is tautomeric with the group of formula (IIc):

$$-X-P(O^-)(O)-D-N^+(H)(R^5)(R^6) \tag{IIc}$$

(in which X, R$^5$, R$^6$ and D are as defined above).

Salts in which —Y—D—Q represents the aforementioned group of formula (IIa) can also form salts with cations, particularly metals (e.g. alkali metals such as sodium or potassium or alkaline earth metals such as calcium or magnesium or other metals such as tin), in which the cation replaces the hydrogen atom of the hydroxy group attached to the phosphorus atom in the group of formula (IIa).

Where Z in the above formula (IIa) represents a halogen atom, this may be, for example, a chlorine, bromine or iodine atom. Where Z represents an alkylsulfonyloxy group, the alkyl part is C$_1$-C$_6$ and may be a straight or branched chain group; examples include the methanesulfonyloxy and ethanesulfonyloxy groups. Where Z represents a haloalkylsulfonyloxy group, the alkyl part is $C_1-C_6$ and may be a straight or branched chain group; an example is the trifluoromethanesulfonyloxy group. Where Z represents an arylsulfonyloxy group, the aryl part is a $C_6-C_{10}$ carbocyclic aryl group, which may be substituted or unsubstituted and, if substituted, may have from 1 to 3 substituents preferably selected from the group consisting of $C_1-C_4$ alkyl (preferably methyl) groups, halogen atoms, $C_1-C_4$ alkoxy groups, aliphatic acyloxy groups (e.g. acetoxy, oxalyloxy and maleoyloxy groups), amino acid residues (e.g. glycyloxy, alanyloxy, asparagyloxy and glutamyloxy groups) and nitro groups. Examples of such arylsulfonyloxy groups include the benzenesulfonyloxy and p-toluenesulfonyloxy groups.

In the compounds of the invention, when $R^1$ represents an alkyl group having from 8 to 22 carbon atoms or an alkylcarbamoyl group in which the alkyl part has from 8 to 22 carbon atoms or when $R^1$ represents a heterocyclic group substituted by an alkyl group having from 8 to 22 carbon atoms, this alkyl group may be a straight or branched chain group, and examples include the octyl, nonyl, decyl, 3-methylnonyl, 8-methylnonyl, 3-ethyloctyl, 3,7-dimethyloctyl, undecyl, dodecyl, tridecyl, tetradecyl, pentadecyl, hexadecyl, 1-methylpentadecyl, 14-methylpentadecyl, 13,13-dimethyltetradecyl, heptadecyl, 15-methylhexadecyl, octadecyl, 1-methylheptadecyl, nonadecyl, icosyl, henicosyl and docosyl groups, of which the straight and branched chain alkyl groups having from 13 to 20, more preferably from 14 to 18, carbon atoms are preferred.

Where $R^2$, $R^3$, $R^5$, $R^6$, $R^7$ or substituent (a), (b) or (c) represents an alkyl group this may be a straight or branched alkyl group having from 1 to 6 carbon atoms, and examples include the methyl, ethyl, propyl, isopropyl, butyl, sec-butyl, t-butyl, pentyl, isopentyl, 2-methylbutyl, neopentyl, hexyl, 4-methylpentyl, 3-methylpentyl, 2-methylpentyl, 3,3-dimethylbutyl, 2,2-dimethylbutyl, 1,1-dimethylbutyl, 1,2-dimethylbutyl, 1,3-dimethylbutyl and 2,3-dimethylbutyl groups, of which those alkyl groups having from 1 to 4 carbon atoms are preferred.

Where $R^2$, $R^3$, or substituent (a) or (c) represents an aliphatic acyl group this may be a straight or branched chain, saturated or unsaturated aliphatic acyl group having from 1 to 6 carbon atoms and is preferably an alkanoyl, alkenoyl or alkynoyl group which may be substituted or unsubstituted. Where it is substituted, the substituents are preferably selected from the group consisting of substituents (c), defined above, more preferably halogen atoms and $C_1$ to $C_4$ alkoxy groups. Examples of such groups include the formyl, acetyl, chloroacetyl, dichloroacetyl, trichloroacetyl, trifluoroacetyl, methoxyacetyl, propionyl, butyryl, (E)-2-methyl-2-butenoyl, isobutyryl, pentanoyl and pivaloyl groups, of which the saturated aliphatic acyl groups having from 1 to 6 carbon atoms are preferred and the acetyl group is more preferred.

Where $R^2$, $R^3$, or substituent (a) or (c) represents an aromatic acyl group, the aryl part thereof may be as defined above, the group being an arylcarbonyl group, in which the aryl part may be substituted or unsubstituted. Where it is substituted, the substituents ar preferably selected from the group consisting of substituents (c), defined above, more preferably halogen atoms and $C_1$ to $C_4$ alkyl, $C_1$ to $C_4$ haloalkyl, $C_1$ to $C_4$ alkoxy, $C_2$ to $C_5$ alkoxycarbonyl, aryl and nitro groups. Examples of such aromatic acyl groups include the benzoyl, o-(dibromomethyl)benzoyl, o-(methoxycarbonyl)benzoyl, p-phenylbenzoyl, 2,4,6-trimethylbenzoyl, p-toluoyl, p-anisoyl, p-chlorobenzoyl, p-nitrobenzoyl, o-nitrobenzoyl and 1- and 2-naphthoyl, preferably 1-naphthoyl, of which the benzoyl group is preferred.

Where $R^2$ or substituent (a) or (c) represents an aryl group, it may be as defined above and may be substituted or unsubstituted. Where it is substituted, the substituents are preferably selected from the group consisting of substituents (c), defined above, more preferably halogen atoms and $C_1$ to $C_4$ alkyl, $C_1$ to $C_4$ haloalkyl, $C_1$ to $C_4$ alkoxy, $C_2$ to $C_5$ alkoxycarbonyl, aryl and nitro groups. Examples of such aryl groups include aryl groups having, in total, from 6 to 12 carbon atoms, for example the phenyl, tolyl, xylyl and naphthyl groups, of which the phenyl group is preferred.

Where $R^2$ or substituent (a) or (c) represents an aralkyl group, the aryl part may be as defined above and may be substituted or unsubstituted. Where it is substituted, the substituents are preferably selected from the group consisting of substituents (c), defined above, more preferably halogen atoms and $C_1$ to $C_4$ alkyl, $C_1$ to $C_4$ haloalkyl, $C_1$ to $C_4$ alkoxy, $C_2$ to $C_5$ alkoxycarbonyl, aryl and nitro groups. The alkyl part is preferably a $C_1$ to $C_4$ alkyl group for example selected from those alkyl groups defined above in relation to $R^2$, more preferably a methyl or ethyl group. Examples of such aralkyl groups include aralkyl groups having, in total, from 7 to 13 carbon atoms, for example the benzyl, phenethyl, phenylpropyl and 1- or 2-, preferably 1-, naphthylmethyl, of which the benzyl group is preferred.

Where $R^1$ and/or $R^2$ represents a heterocyclic group, this has from 5 to 11, preferably from 5 to 7, ring atoms, of which from 1 to 3 are hetero-atoms selected from the group consisting of sulfur and/or oxygen and/or nitrogen atoms. Examples of such groups include the furyl, thienyl, pyrrolyl, pyrazolyl, imidazolyl, imidazolinyl, oxazolyl, isoxazolyl, thiazolyl, oxadiazolyl (e.g. 1,2,3-oxadiazolyl), triazolyl, thiadiazolyl, pyranyl, pyridyl, pyridazinyl, pyrimidinyl and pyrazinyl groups. Other examples include partly or completely hydrogenated analogs of each of the above. Also included are analogs of the above groups in which a phenyl or substituted phenyl group is fused to the heterocyclic ring, for example the benzofuryl, isobenzofuryl, benzothienyl, indolizinyl, indolyl, isoindolyl, indazolyl, quinolyl, isoquinolyl, phthalazinyl, quinoxalinyl, quinazolinyl, cinnolinyl, chromanyl, indolinyl and isoindolinyl groups. Of these, the nitrogen-containing aromatic heterocyclic groups are preferred, and the isoxazolyl, thiazolyl, imidazolyl and oxazolyl groups are more preferred. Where $R^1$ represents such a group it has one $C_8-C_{22}$ alkyl substituent, e.g. as exemplified above, and optionally at least one substituent selected from the group consisting of substituents (a), e.g. as exemplified below. Where $R^2$ represents such a group, it may be unsubstituted or may have at least one substituent selected from the group consisting of substituents (a), e.g. as exemplified below.

Where $R^3$ represents an alkoxycarbonyl group this has from 1 to 6 carbon atoms in the alkoxy moiety, i.e. it is a $C_2-C_7$ group. Examples include the methoxycarbonyl, ethoxycarbonyl, propoxycarbonyl, isopropoxycarbonyl, butoxycarbonyl, sec-butoxycarbonyl, t-butoxycarbonyl, pentoxycarbonyl, isopentoxycarbonyl, 2-methylbutoxycarbonyl, neopentoxycarbonyl, hexoxycarbonyl, 4-methylpentoxycarbonyl, 3-methylpentoxycarbonyl, 2-methylpentoxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl and 2,3-dimethylbutoxycarbonyl groups, of which those alkoxycarbonyl groups having from 2 to 5 carbon atoms are preferred, the methoxycarbonyl and ethoxycarbonylgroups being most preferred.

Such alkoxycarbonyl groups may be substituted or unsubstituted. Where they are substituted, the substituents are preferably selected from the group consisting of halogen atoms and trialkylsilyl groups. Examples of such halogen atoms include the fluorine, chlorine, bromine and iodine atoms. In the trialkylsilyl groups, the alkyl parts may be the same or different and each has from 1 to 4 carbon atoms. Examples of such trialkylsilyl groups include the trimethylsilyl, triethylsilyl, tripropylsilyl, triisopropylsilyl, tributylsilyl, methyldiethylsilyl, ethyldimethylsilyl and t-butyldimethylsilyl groups.

Specific examples of preferred groups which may be represented by $R^3$ include the lower aliphatic and aromatic acyl groups, such as the formyl, acetyl, chloroacetyl, propionyl and benzoyl groups; alkyloxycarbonyl groups, such as the t-butyloxycarbonyl, 2,2,2-tribromoethyloxycarbonyl and 2-trimethylsilylethoxycarbonyl groups; and alkenyloxycarbonyl groups, such as the allyloxycarbonyl group.

The group D represents a $C_1$-$C_{14}$ alkylene group or a substituted $C_1$-$C_{14}$ alkylene group having one substituent selected from the group consisting of carboxy groups and protected carboxy groups. Of these alkylene groups, the $C_1$-$C_{10}$ alkylene groups are preferred and the $C_1$-$C_8$ alkylene groups are more preferred. Examples of such groups include groups of formulae: —$CH_2$—, —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$(CH_2)_9$—, —$(CH_2)_{10}$—, —$(CH_2)_{11}$—, —$(CH_2)_{12}$—, —$(CH_2)_{13}$—, —$(CH_2)_{14}$—, —$CHR^8$—, —$CHR^8CH_2$—, —$CH_2CHR^8CH^2$—, —$CHR^8(CH_2)_2$—, —$CHR^8(CH_2)_3$—, —$CHR^8(CH_2)_4$—, —$CHR^8(CH_2)_5$—, —$CHR^8(CH_2)_6$—, —$CHR^8(CH_2)_7$—, —$CHR^8(CH_2)_8$—, —$CH_2CHR^8(CH_2)_2$—, —$CH_2CHR^8(CH_2)_2$—, —$CH_2CHR^8(CH_2)_4$—, —$CH_2CHR^8(CH_2)_5$—, —$CH_2CHR^8(CH_2)_6$—, —$CH_2CHR^8(CH_2)_7$—, —$(CH_2)_2CHR^8(CH_2)_2$—, —$(CH_2)_2CHR^8(CH_2)_3$—, —$(CH_2)_2CHR^8(CH_2)_4$—, —$(CH_2)_2CHR^8(CH_2)_5$—, —$(CH_2)_3CHR^8(CH_2)_2$—, —$(CH_2)_4CHR^8(CH_2)_3$—, —$(CH_2)_4CHR^8(CH_2)_2$— and —$(CH_2)_5CHR^8(CH_2)_2$— groups, in which $R^8$ represents a carboxy group or a protected carboxy group Examples of protecting groups which may be represented by $R^8$ include: any one of the lower alkyl groups defined above; aralkyl groups, such as the benzyl, p-nitrobenzyl, o-nitrobenzyl, triphenylmethyl, diphenylmethyl, bis(o-nitrophenyl)methyl, 9-anthrylmethyl, 2,4,6-trimethylbenzyl, p-bromobenzyl, p-methoxybenzyl and piperonyl groups; aliphatic acyloxymethyl groups, such as the acetoxymethyl, propionyloxymethyl, butyryloxymethyl, isobutyryloxymethyl and pivaloyloxymethyl groups; 1-(alkoxycarbonyloxy)ethyl groups, in which the alkoxy part is $C_1$-$C_6$, preferably $C_1$-$C_4$, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl and 1-isobutoxycarbonyloxyethyl groups; carboxy-protecting groups capable of being hydrolyzed in vivo, such as the phthalidyl and (2-oxo-5-methyl-1,3-dioxolen-4-yl)methyl groups; alkyloxymethyl groups, in which the alkyl part is $C_1$-$C_6$, preferably $C_1$-$C_4$, such as the methoxymethyl, ethoxymethyl, propoxymethyl, isopropoxymethyl, butoxymethyl and methoxyethoxymethyl groups; and halogenated $C_1$-$C_6$, preferably $C_1$-$C_4$, alkyl groups, such as the 2,2,2-trichloroethyl, 2-haloethyl (e.g. 2-chloroethyl, 2-fluoroethyl, 2-bromoethyl or 2-iodoethyl) and 2,2-dibromoethyl groups. Of these, the alkyl groups, the aralkyl groups and carboxy-protecting groups capable of being hydrolyzed in vivo are preferred.

Where Q represents a nitrogen-containing heterocyclic group, this has from 5 to 11, preferably from 5 to 7, ring atoms, of which from 1 to 3 are hetero-atoms selected from the group consisting of sulfur and/or oxygen and/or nitrogen atoms, at least one being a nitrogen atom. Such groups may be fully unsaturated or partly or completely hydrogenated. Also included are analogs of such groups in which a phenyl or substituted phenyl group is fused to the heterocyclic ring. Examples of these heterocyclic groups include the pyrrolidinyl, piperidinyl, piperazinyl, azepinyl, morpholinyl (e.g. morpholino), thiomorpholinyl (e.g. thiomorpholino), pyridyl, thiazolyl, oxazolyl, imidazolinyl, pyridazinyl, quinolyl, isoquinolyl, imidazolyl, triazolyl and tetrazolyl groups, of which aromatic heterocyclic groups having 5 or 6 ring atoms and optionally having a phenyl group fused thereto are preferred and the pyridyl, imidazolyl, thiazolyl, quinolyl and isoquinolyl groups are more preferred. Such groups may be quaternized, in which case the positive charge of the quaternary nitrogen atom is balanced by a negative charge from an anion $Z^-$, as defined above.

Where substituent (b) or (c) represents a halogen atom, this is preferably a fluorine, chlorine, bromine or iodine atom.

Where substituent (b) or (c) represents an alkoxy group, this is preferably a methoxy, ethoxy, propoxy, isopropoxy, butoxy, sec-butoxy, t-butoxy, pentoxy, isopentoxy, 2-methylbutoxy, neopentoxy or hexoxy group more preferably a methoxy, ethoxy or propoxy group and most preferably a methoxy or ethoxy group.

Where substituent (c) represents a group of formula —$CONR'_2$, this is a carbamoyl group or a mono- or di-alkylcarbamoyl groups in which the or each alkyl part is $C_1$-$C_6$. Examples include such groups as the methylcarbamoyl, ethylcarbamoyl, propylcarbamoyl, isopropylcarbamoyl, butylcarbamoyl, isobutylcarbamoyl, sec-butylcarbamoyl, t-butylcarbamoyl, pentylcarbamoyl, t-pentylcarbamoyl, dimethylcarbamoyl, diethylcarbamoyl, dipropylcarbamoyl, dibutylcarbamoyl, methylethylcarbamoyl and methylpropylcarbamoyl groups. R' may also represent an aryl group, in which case the group is preferably a phenylcarbamoyl group.

Where substituent (c) represents an amino group or a mono- or di-alkylamino groups in which the or each alkyl part is $C_1$-$C_6$. Examples include such groups as the methylamino, ethylamino, propylamino, isopropylamino, butylamino, isobutylamino, sec-butylamino, t-butylamino, pentylamino, t-pentylamino, dimethylamino, diethylamino, dipropylamino, dibutylamino, methylethylamino and methylpropylamino groups.

Where substituent (c) represents a heterocyclic group or a substituted heterocyclic group having at least one substituent selected from the group consisting of substituents (a) and substituents (b), defined above, the heterocyclic group may be any one of those exemplified above in relation to $R^1$, $R^2$ or Q and may be unsubstituted or substituted as defined.

Preferred compounds of the invention are those compounds of formula (I) in which:

$R^1$ represents a $C_8$-$C_{22}$ alkyl group, an alkylcarbamoyl group in which the alkyl part is $C_8$-$C_{22}$ or an aromatic heterocyclic group having 5 or 6 ring atoms and having one $C_8$-$C_{22}$ alkyl substituent;

$R^2$ represents a $C_1$-$C_6$ alkyl group, a $C_1$-$C_6$ aliphatic acyl group, an aromatic heterocyclic group or substituted heterocyclic group having 5 or 6 ring atoms, said substituted heterocyclic group having at least one substituent selected from the group consisting of substituents (a'), defined below;

Y represents an oxygen atom, a sulfur atom, a group of formula —X—CO—$R^4$—, a group of formula —$R^4$—CO—X—, a group of formula —$NR^3$—CO—, a group of formula —CO—$NR^3$— or a group of formula —X—P(O)(OH)—O—, where:

$R^3$ represents a hydrogen atom, a $C_1$-$C_6$ alkyl group, a $C_1$-$C_6$ aliphatic acyl group, a $C_2$-$C_7$ alkoxycarbonyl group or a substituted $C_2$-$C_7$ alkoxycarbonyl group having at least one substituent selected from the group consisting of halogen atoms and trialkylsilyl groups where each alkyl part is $C_1$-$C_6$; and $R^4$ represents a direct bond or a group of formula —$NR^3$ where $R^3$ is as defined above; and X represents an oxygen atom or a sulfur atom;

D represents a $C_1$-$C_{10}$ alkylene group or a substituted $C_1$-$C_{10}$ alkylene group having one substituent selected from the group consisting of carboxy groups and $C_2$-$C_7$ alkoxycarbonyl groups;

Q represents a nitrogen-containing heterocyclic group having 5 or 6 ring atoms of which from 1 to 3 are hetero-atoms selected from the group consisting of nitrogen, oxygen and sulfur atoms, at least one of said hetero-atoms being a nitrogen atom and/or quaternary ring nitrogen atom, a substituted nitrogen-containing heterocyclic group containing at least one ring nitrogen atom and/or quaternary ring nitrogen atom, said substituted nitrogen-containing heterocyclic group having at least one substituent selected from the group consisting of substituents (b'), such a nitrogen-containing heterocyclic group having a phenyl group fused thereto, a group of formula —$NR^5R^6$ or a group of formula —$N^+R^5R^6R^7$.$Z^-$;

where $R^5$, $R^6$ and $R^7$ are independently selected from the group consisting of hydrogen atoms and $C_1$-$C_6$ alkyl groups and $Z^-$ represents a pharmaceutically acceptable anion; substituents (a'):

$C_1$-$C_6$ alkyl groups, $C_1$-$C_6$ aliphatic acyl groups, and aryl groups.

substituents (b'):

$C_1$-$C_6$ alkyl groups, $C_1$-$C_6$ alkoxy groups, halogen atoms and $C_1$-$C_6$ hydroxyalkyl groups.

provided that, when $R^1$ represents said alkyl or alkylcarbamoyl group. $R^2$ represents said heterocyclic or substituted heterocyclic group; and pharmaceutically acceptable salts, esters and amides thereof.

More preferred compounds of the invention are those compounds of formula (I) in which:

$R^1$ represents a $C_{14}$-$C_{20}$ alkyl group, an alkylcarbamoyl group in which the alkyl part is $C_8$-$C_{22}$ or an aromatic heterocyclic group having 5 or 6 ring atoms and having one $C_8$-$C_{22}$ alkyl substituent;

$R^2$ represents a $C_1$-$C_6$ alkyl group, an aromatic heterocyclic group or substituted aromatic heterocyclic group having 5 or 6 ring atoms, said substituted heterocyclic group having at least one substituent selected from the group consisting of substituents (a'') defined below;

Y represents an oxygen atom, a sulfur atom, a group of formula —X—CO—$R^4$—, or a group of formula —X—P(O)(OH)—O—, where:

$R^4$ represents a direct bond or a group of formula —$NR^3$ where $R^3$ represents a hydrogen atom, a $C_1$-$C_6$ alkyl group, a $C_1$-$C_6$ aliphatic acyl group or a $C_2$-$C_7$ alkoxycarbonyl group; and X represents an oxygen atom or a sulfur atom;

D represents a $C_1$-$C_{10}$ alkylene group or a substituted $C_1$-$C_{10}$ alkylene group having one substituent selected from the group consisting of carboxy groups and $C_2$-$C_7$ alkoxycarbonyl groups;

Q represents a nitrogen-containing aromatic heterocyclic group having 5 or 6 ring atoms of which from 1 to 3 are hetero-atoms selected from the group consisting of nitrogen, oxygen and sulfur atoms, at least one of said hetero-atoms being a nitrogen atom and/or quaternary ring nitrogen atom, a substituted nitrogen-containing heterocyclic group containing at least one ring nitrogen atom and/or quaternary ring nitrogen atom, said substituted nitrogen-containing heterocyclic group having at least one substituent selected from the group consisting of substituents (b''), such a nitrogen-containing heterocyclic group having a phenyl group fused thereto, a group of formula —$NR^5R^6$ or a group of formula —$N^+R^5R^6R^7$.$Z^-$;

where $R^5$, $R^6$ and $R^7$ are independently selected from the group consisting of hydrogen atoms and $C_1$-$C_6$ alkyl,groups and $Z^-$ represents a pharmaceutically acceptable anion;

substituents (a''):

$C_1$-$C_6$ alkyl groups and aryl groups.

substituents (b''):

$C_1$-$C_6$ alkyl groups and $C_1$-$C_6$ hydroxyalkyl groups.

provided that, when $R^1$ represents said alkyl or alkylcarbamoyl group. $R^2$ represents said heterocyclic or substituted heterocyclic group; and pharmaceutically acceptable salts, esters and amides thereof.

Most preferred compounds of the invention are those compounds of formula (I) in which:

$R^1$ represents an alkylcarbamoyl group in which the alkyl part is $C_8$-$C_{22}$ or an aromatic heterocyclic group having 5 or 6 ring atoms and having one $C_8$-$C_{22}$ alkyl substituent;

$R^2$ represents an aromatic heterocyclic group or substituted heterocyclic group having 5 or 6 ring atoms, said substituted heterocyclic group having at least one substituent selected from the group consisting of substituents (a''). defined above;

Y represents an oxygen atom, a group of formula —X—CO—$R^4$—, or a group of formula —X—P(O)(OH)—O—, where:

$R^4$ represents a direct bond or a group of formula —$NR^3$ where $R^3$ represents a hydrogen atom, a $C_1$-$C_6$ alkyl group or a $C_1$-$C_6$ aliphatic acyl group; and X represents an oxygen atom;

D represents a $C_1$-$C_8$ alkylene group or a substituted $C_1$-$C_8$ alkylene group having one substituent selected from the group consisting of carboxy groups and $C_2$-$C_7$ alkoxycarbonyl groups;

Q represents a nitrogen-containing aromatic heterocyclic group having 5 or 6 ring atoms of which from 1 to 3 are hetero-atoms selected from the group consisting of nitrogen, oxygen and sulfur atoms, at least one of said hetero-atoms being a nitrogen atom and/or quaternary ring nitrogen atom, a substituted nitrogen-containing heterocyclic group containing at least one ring nitrogen atom and/or quaternary ring nitrogen atom, said substituted nitrogen-containing heterocyclic group having at least one substituent selected from the group consisting of substituents (b'''') such a nitrogen-containing heterocyclic group having a phenyl group fused thereto, a group of formula $-NR^5R^6$ or a group of formula $-N^+R^5R^6R^7 \cdot Z^-$;

where $R^5$, $R^6$ and $R^7$ are independently selected from the group consisting of $C_1-C_6$ alkyl groups and $Z^-$ represents a pharmaceutically acceptable anion; substituents (b''''):

$C_1-C_6$ alkyl groups, provided that, when $R^1$ represents said alkylcarbamoyl group, $R^2$ represents said heterocyclic or substituted heterocyclic group; and pharmaceutically acceptable salts, esters and amides thereof.

An alternative preferred class of compounds of the present invention are those compounds of formula (I) in which:

$R^1$ represents an aromatic heterocyclic group having 5 or 6 ring atoms and having one $C_8-C_{22}$ alkyl substituent;

$R^2$ represents an aromatic heterocyclic group or substituted aromatic heterocyclic group having 5 or 6 ring atoms, said substituted heterocyclic group having at least one substituent selected from the group consisting of substituents (a''), defined above;

Y represents an oxygen atom, a sulfur atom, a group of formula $-X-CO-R^4-$, a group of formula $-R^4-CO-X-$, a group of formula $-NR^3-CO-$, a group of formula $-CO-NR^3-$ or a group of formula $-X-P(O)(OH)-O-$, where:

$R^3$ represents a hydrogen atom, a $C_1-C_6$ alkyl group, a $C_1-C_6$ aliphatic acyl group or a $C_2-C_7$ alkoxycarbonyl group; and $R^4$ represents a direct bond or a group of formula $-NR^3$ where $R^3$ is as defined above; and X represents an oxygen atom or a sulfur atom;

D represents a $C_1-C_{14}$ alkylene group or a substituted $C_1-C_{14}$ alkylene group having one substituent selected from the group consisting of carboxy groups and $C_2-C_7$ alkoxycarbonyl groups;

Q represents a nitrogen-containing aromatic heterocyclic group having 5 or 6 ring atoms of which from 1 to 3 are hetero-atoms selected from the group consisting of nitrogen, oxygen and sulfur atoms, at least one of said hetero-atoms being a nitrogen atom and/or quaternary ring nitrogen atom, a substituted nitrogen-containing heterocyclic group containing at least one ring nitrogen atom and/or quaternary ring nitrogen atom, said substituted nitrogen-containing heterocyclic group having at least one substituent selected from the group consisting of substituents (b''), defined above, such a nitrogen-containing heterocyclic group having a phenyl group fused thereto, a group of formula $-NR^5R^6$ or a group of formula $-N^+R^5R^6R^7 \cdot Z^-$; where $R^5$, $R^6$ and $R^7$ are independently selected from the group consisting of hydrogen atoms and $C_1-C_6$ alkyl groups and $Z^-$ represents a pharmaceutically acceptable anion;

and pharmaceutically acceptable salts, esters and amides thereof.

The compounds of the invention may contain one carboxy group in the alkylene group represented by D. This carboxy group may form esters, amides and salts.

Where the carboxy group is esterified, the nature of the resulting ester is not critical to the present invention. In principle, such compounds of the invention, being carboxylic acids, will form esters with any ester-forming alcohol and all such esters form part of the present invention. However, where the esters are to be employed for therapeutic purposes, it is, of course, necessary that the resulting esters should be pharmaceutically acceptable, which, as is understood in the art, means that the esters should not have reduced activity (or unacceptably reduced activity) and should no have increased toxicity (or unacceptably increased toxicity) as compared with the free acid. However, where the ester is to be employed for other purposes, for example as an intermediate in the preparation of other compounds, even this criterion does not apply.

Examples of such esters include: $C_1-C_6$, more preferably $C_1-C_4$, alkyl esters, for example the methyl, ethyl, propyl, isopropyl, butyl, isobutyl, sec-butyl, t-butyl, pentyl and hexyl esters; aralkyl and diarylalkyl esters, such as the benzyl, p-nitrobenzyl and benzhydryl esters; alkoxycarbonylalkyl esters, in which the alkoxy and alkyl parts are both $C_1-C_4$, especially alkoxycarbonylmethyl esters, such as the ethoxycarbonylmethyl and t-butoxycarbonylmethyl esters; alkoxycarbonyloxyalkyl esters in which the alkoxy and alkyl parts are both $C_1-C_4$, especially 2-(alkoxycarbonyloxy)ethyl esters, such as the 2-methoxycarbonyloxyethyl, 2-ethoxycarbonyloxyethyl and 2-t-butoxycarbonyloxyethyl esters; and other specific esters, such as the phthalidyl, substituted phthalidyl, phenacyl, substituted phenacyl (e.g. p-nitrophenacyl) and (5-methyl-2-oxo-1,3-dioxolen-4-yl)methyl esters.

Likewise, where the carboxy group has formed an amide, the precise nature of the amide is not critical, provided that, where the amide is to be used for therapeutic purposes, the resulting amide is pharmaceutically acceptable. Accordingly, the carboxy group can be replaced by a carbamoyl group or a substituted carbamoyl group, preferably an alkylcarbamoyl or dialkylcarbamoyl group in which each alkyl group is a $C_1-C_4$ alkyl group [e.g. as defined above in relation to substituent (c)], for example a methylcarbamoyl, ethylcarbamoyl, dimethylcarbamoyl or diethylcarbamoyl group.

The carboxy group may also form salts with appropriate bases. The nature of such salts is likewise not critical, provided that, where they are to be used for therapeutic purposes, the salts are pharmaceutically acceptable. Examples of salts with bases include: salts with metals, especially alkali metals and alkaline earth metals, such as the lithium, sodium, potassium, calcium and magnesium salts; the ammonium salt; salts with organic amines, such as cyclohexylamine, diisopropylamine or triethylamine; and salts with basic amino acids, such as lysine or arginine.

The compounds of the invention may contain several asymmetric carbon atoms and, accordingly, optical isomers of the compounds are possible. Although the various optical isomers are all represented herein by a single formula, the present invention embraces both the individual isolated isomers and mixtures thereof.

Examples of specific compounds of the invention are given in the following formulae (I-1) to (I-5), in which the substituents are as defined in the corresponding one of Tables 1 to 5 [i.e. Table 1 relates to formula (I 1).

Table 2 relates to formula (I-2) and so on]. The compounds of the invention are hereinafter, where appropriate, identified by the numbers appended to them in these Tables. In the Tables, the following abbreviations are used:

| | |
|---|---|
| Ac | acetyl |
| Bz | benzyl |
| Et | ethyl |
| Hpd | heptadecyl |
| Hxd | hexadecyl |
| Imid | imidazolyl |
| Imid+ | imidazol-3-yl 3-cation |
| Imin+ | 2-imidazolinyl 1-cation |
| Isox | 3-isoxazolyl |
| Me | methyl |
| Mor | morpholino |
| Mor+ | morpholino 4-cation |
| Ocd | octadecyl |
| Ph | phenyl |
| Pip | piperidyl |
| Pip+ | piperidyl 1-cation |
| Pnd | pentadecyl |
| Pyr | pyridyl |
| Pyr+ | pyridyl 1-cation |
| Pyrd | pyrrolidinyl |
| Pyrd+ | pyrrolidine 1-cation |
| Quin+ | quinolyl 1-cation |
| i-Quin+ | isoquinolyl 2-cation |
| Tez | 1H-tetrazolyl |
| Thi | thiazolyl |
| Thi+ | thiazolyl 3-cation |

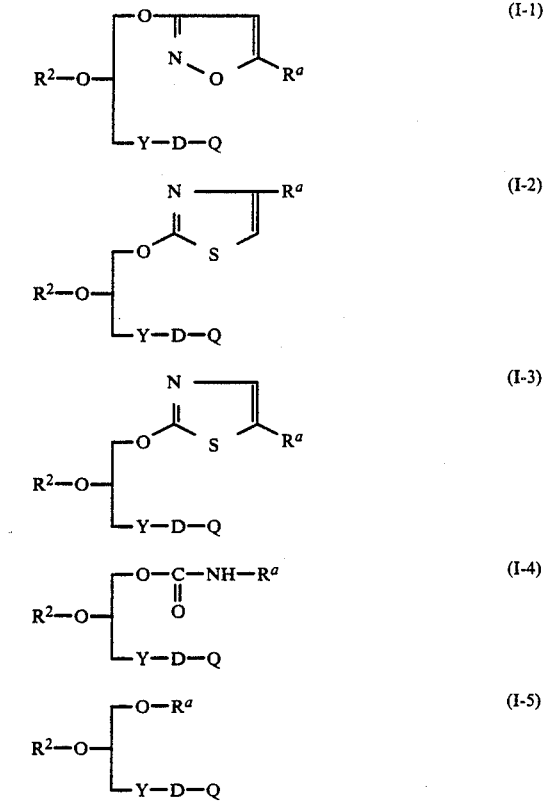

TABLE 1

| Cpd. No. | $R^a$ | $R^2$ | Y | D | Q |
|---|---|---|---|---|---|
| 1-1 | Pnd | Me | —O.CO.NH— | —(CH$_2$)$_5$— | 3-Thi+ |
| 1-2 | Pnd | Et | —O.CO.NH— | —(CH$_2$)$_5$— | 3-Thi+ |
| 1-3 | Hxd | Bz | —O.CO.NH— | —(CH$_2$)$_3$— | 1-Me-3-Imid+ |
| 1-4 | Hxd | Isox | —O.CO.NH— | —CH(COOEt)—(CH$_2$)$_5$— | 3-Thi+ |
| 1-5 | HPd | Ac | —O.CO.NH— | —CH$_2$CH(COOH)—CH$_2$— | —NMe$_2$ |
| 1-6 | Pnd | 5-MeIsox | —O.CO.NH— | —CH$_2$CH(COOMe)—(CH$_2$)$_4$— | 3-Thi+ |
| 1-7 | Pnd | Et | —O.CO.NH— | —CH$_2$CH(COOH)—CH$_2$— | —N+Me$_3$ |
| 1-8 | Pnd | Me | —O.CO.NH— | —(CH$_2$)$_5$ | —N+Me$_3$ |
| 1-9 | Pnd | 2-Thi | —O.CO.NH— | —(CH$_2$)$_5$ | 3-Thi+ |
| 1-10 | Pnd | Isox | —O.CO.NH— | —(CH$_2$)$_5$ | 3-Thi+ |
| 1-11 | Hxd | Isox | —O.CO.NH— | —(CH$_2$)$_5$ | 3-Thi+ |
| 1-12 | Pnd | 5-MeIsox | —O.CO.NH— | —(CH$_2$)$_5$ | 3-Thi+ |
| 1-13 | Pnd | 5-MeIsox | —O.CO.NH— | —(CH$_2$)$_5$ | —N+Me$_3$ |
| 1-14 | Ocd | 5-PhIsox | —O.CO.NH— | —(CH$_2$)$_4$— | 1-Pip |
| 1-15 | Pnd | Me | —O.CO.NAc— | —(CH$_2$)$_4$— | 1-Me-1-Pip+ |
| 1-16 | Hxd | Et | —O.CO.NAc— | —(CH$_2$)$_4$— | Mor |
| 1-17 | Hpd | 2-Thi | —O.CO.NAc— | —(CH$_2$)$_4$— | 4-MeMor+ |
| 1-18 | Ocd | Ac | —O.CO.NAc— | —(CH$_2$)$_5$— | 1-Me-2-Pyr+ |
| 1-19 | Pnd | Isox | —O.CO.NAc— | —(CH$_2$)$_5$— | 3-Pyr |
| 1-20 | Hxd | 5-MeIsox | —O.CO.NAc— | —(CH$_2$)$_5$— | 1-ME-3-Pyr+ |
| 1-21 | Hpd | 5-PhIsox | —O.CO.NAc— | —CH$_2$— | 2-Pyr |
| 1-22 | Hxd | Me | O | —(CH$_2$)$_7$— | 3-Thi+ |
| 1-23 | Pnd | Et | O | —(CH$_2$)$_7$— | 3-Thi+ |
| 1-24 | Hxd | Ac | O | —(CH$_2$)$_6$— | 4-Thi |
| 1-25 | Hpd | Isox | O | —(CH$_2$)$_6$— | 4-Me-5-Thi |
| 1-26 | Pnd | 5-MeIsox | O | —(CH$_2$)$_7$— | 3-Thi+ |
| 1-27 | Pnd | 5-MeIsox | O | —(CH$_2$)$_8$— | 1-Me-3-Pyr+ |
| 1-28 | Pnd | 5-PhIsox | S | —(CH$_2$)$_7$— | 1-Et-2-Pyrd |
| 1-29 | Hxd | Me | —NH.CO.O— | —(CH$_2$)$_7$— | 1,1-diEt-2-Pyrd+ |
| 1-30 | Hpd | Et | —NH.CO.O— | —(CH$_2$)$_7$— | 3-Thi+ |

TABLE 1-continued

| Cpd. No. | R$^a$ | R$^2$ | Y | D | Q |
|---|---|---|---|---|---|
| 1-31 | Ocd | Ac | —NH.CO.O— | —(CH$_2$)$_8$— | 1-Me-3-Imid$^+$ |
| 1-32 | Pnd | Isox | —NH.CO.O— | —(CH$_2$)$_8$— | 1-Me-1-Imid$^+$ |
| 1-33 | Hxd | 5-MeIsox | —NH.CO.O— | —(CH$_2$)$_8$— | 1-Me-1-Pyrd$^+$ |
| 1-34 | Hpd | 5-PhIsox | —NH.CO.O— | —(CH$_2$)$_8$— | 1-Me-1-Pip$^+$ |
| 1-35 | Ocd | Me | —CO.NH— | —(CH$_2$)$_9$— | 4-MeMor$^+$ |
| 1-36 | Pnd | Et | —CO.NH— | —(CH$_2$)$_9$— | 1-Me-2-Pyr$^+$ |
| 1-37 | Hxd | Ac | —CO.NH— | —(CH$_2$)$_9$— | 1-Me-3-Pyr$^+$ |
| 1-38 | Hpd | Isox | —CO.NH— | —(CH$_2$)$_9$— | 3-Et-2-Thi$^+$ |
| 1-39 | Ocd | 5-MeIsox | —CO.NH— | —(CH$_2$)$_{10}$— | 3,4-diMe-5-Thi$^+$ |
| 1-40 | Pnd | 5-PhIsox | —CO.NH— | —(CH$_2$)$_{10}$— | 3-Thi$^+$ |
| 1-41 | Hxd | Me | —NH.CO— | —(CH$_2$)$_{10}$— | 1-Me-3-Imid$^+$ |
| 1-42 | Hpd | Et | —NH.CO— | —(CH$_2$)$_{10}$— | 1-Me-1-Imid$^+$ |
| 1-43 | Ocd | Ac | —NH.CO— | —(CH$_2$)$_{11}$— | 1-Me-1-Pyrd$^+$ |
| 1-44 | Pnd | Isox | —NH.CO— | —(CH$_2$)$_{11}$— | 1-Me-1-Pip$^+$ |
| 1-45 | Hxd | 5-MeIsox | —NH.CO— | —(CH$_2$)$_{11}$— | 4-MeMor$^+$ |
| 1-46 | Hpd | 5-PhIsox | —NH.CO— | —(CH$_2$)$_{11}$— | 1-Me-2-Pyr$^+$ |
| 1-47 | Hxd | Isox | —OP(O)(OH)O— | —(CH$_2$)$_2$— | 3-Thi$^+$ |
| 1-48 | Hxd | Isox | —OP(O)(OH)O— | —(CH$_2$)$_2$— | 1-Me-3-Imid$^+$ |
| 1-49 | Hpd | Et | —OP(O)(OH)O— | —(CH$_2$)$_{14}$— | 3-Et-2-Thi$^+$ |
| 1-50 | Hxd | Ac | —OP(O)(OH)O— | —(CH$_2$)$_3$— | 3,4-diMe-5-Thi$^+$ |
| 1-51 | Pnd | Me | —OP(O)(OH)O— | —(CH$_2$)$_2$— | 3-Thi$^+$ |
| 1-52 | Ocd | 5-MeIsox | —OP(O)(OH)O— | —(CH$_2$)$_5$— | 3-Thi$^+$ |
| 1-53 | Pnd | 5-PhIsox | —SP(O)(OH)O— | —(CH$_2$)$_4$— | 1-Me-1-Imid$^+$ |
| 1-54 | Hxd | 2-Thi | —OP(O)(OH)O— | —(CH$_2$)$_4$— | 1-Me-1-Pyrd$^+$ |
| 1-55 | Hxd | Isox | —O.CO.NEt— | —CH$_2$— | 3-Thi$^+$ |
| 1-56 | Pnd | 5-MeIsox | —O.CO.NH— | —(CH$_2$)$_5$— | —NH$_2$ |
| 1-57 | Pnd | 5-MeIsox | —O.CO.NH— | —(CH$_2$)$_5$— | 1-Imid |
| 1-58 | Pnd | 5-MeIsox | —O.CO.NH— | —(CH$_2$)$_5$— | 1-Tez |
| 1-59 | Hxd | Isox | —O.CO.NH— | —CH$_2$— | 2-Pyr |
| 1-60 | Hxd | Isox | —O.CO.NAc— | —CH$_2$— | 1-Et-2-Pyr$^+$ |
| 1-61 | Hxd | Isox | —O.CO.NEt— | —CH$_2$— | 1-Et-2-Pyr$^+$ |
| 1-62 | Pnd | 5-MeIsox | O | —CH$_2$CH(COOH)—(CH$_2$)$_5$— | 3-Thi$^+$ |
| 1-63 | Pnd | 5-MeIsox | —O—P(O)—(OH)O— | —(CH$_2$)$_6$— | 3-Thi$^+$ |
| 1-64 | Hxd | Isox | —O.CO.NAc— | —CH$_2$— | 1-Et-2-Quin$^+$ |
| 1-65 | Hxd | Isox | —CO.NEt— | —CH$_2$— | 1-Et-2-Quin$^+$ |
| 1-66 | Hxd | Isox | —CO.NAc— | —CH$_2$— | 2-Et-1-iQuin$^+$ |
| 1-67 | Hxd | Isox | —CO.NAc— | —CH$_2$— | 2-Et-1-iQuin$^+$ |

TABLE 2

| Cpd No. | R$^a$ | R$^2$ | Y | D | Q |
|---|---|---|---|---|---|
| 2-1 | Pnd | Me | —O.CO.NH— | —(CH$_2$)$_5$— | 3-Thi$^+$ |
| 2-2 | Pnd | Et | —O.CO.NH— | —(CH$_2$)$_5$— | 3-Thi$^+$ |
| 2-3 | Hxd | Bz | —O.CO.NH— | —(CH$_2$)$_3$— | 1-Me-3-Imid$^+$ |
| 2-4 | Hxd | Me | —O.CO.NH— | —(CH$_2$)$_3$— | 1-Imin$^+$ |
| 2-5 | Hpd | Ac | —O.CO.NH— | —(CH$_2$)$_3$— | —NMe$_2$ |
| 2-6 | Pnd | Ac | —O.CO.NH— | —(CH$_2$)$_5$— | 3-Thi$^+$ |
| 2-7 | Pnd | Et | —O.CO.NH— | —(CH$_2$)$_3$— | —N$^+$Me$_3$ |
| 2-8 | Pnd | Me | —O.CO.NH— | —(CH$_2$)$_5$— | —N$^+$Me$_3$ |
| 2-9 | Pnd | 2-Thi | —O.CO.NH— | —(CH$_2$)$_5$— | 3-Thi$^+$ |
| 2-10 | Pnd | Isox | —O.CO.NH— | —(CH$_2$)$_5$— | 3-Thi$^+$ |
| 2-11 | Hxd | Isox | —O.CO.NH— | —(CH$_2$)$_5$— | 3-Thi$^+$ |
| 2-12 | Pnd | 5-MeIsox | —O.CO.NH— | —(CH$_2$)$_2$CH—(COOEt)(CH$_2$)$_2$— | 3-Thi$^+$ |
| 2-13 | Pnd | 5-MeIsox | —O.CO.NH— | —CH(COOMe)—(CH$_2$)$_4$— | —N$^+$Me$_3$ |
| 2-14 | Ocd | 5-PhIsox | —O.CO.NH— | —(CH$_2$)$_4$— | 1-Pip |
| 2-15 | Pnd | Me | —O.CO.NAc— | —(CH$_2$)$_4$— | 1-Me-1-Pip$^+$ |
| 2-16 | Hxd | Et | —O.CO.NAc— | —(CH$_2$)$_4$— | Mor |
| 2-17 | Hpd | 2-Thi | —O.CO.NAc— | —(CH$_2$)$_4$— | 4-MeMor$^+$ |
| 2-18 | Ocd | Ac | —O.CO.NAc— | —(CH$_2$)$_5$— | 1-Me-2-Pyr$^+$ |
| 2-19 | Pnd | Isox | —O.CO.NAc— | —(CH$_2$)$_5$— | 3-Pyr |
| 2-20 | Hxd | 5-MeIsox | —O.CO.NAc— | —(CH$_2$)$_5$— | 1-ME-3-Pyr$^+$ |
| 2-21 | Hpd | 5-PhIsox | —O.CO.NAc— | —(CH$_2$)$_2$— | 2-Pyr |
| 2-22 | Hxd | Me | O | —(CH$_2$)$_7$— | 3-Thi$^+$ |
| 2-23 | Pnd | Et | O | —(CH$_2$)$_7$— | 3-Thi$^+$ |
| 2-24 | Hxd | Ac | O | —(CH$_2$)$_6$— | 4-Thi |
| 2-25 | Hpd | Isox | O | —(CH$_2$)$_6$— | 4-ME-5-Thi |
| 2-26 | Ocd | 5-MeIsox | O | —(CH$_2$)$_7$— | 3,4-diMe-5-Thi$^+$ |
| 2-27 | Pnd | 5-PhIsox | O | —(CH$_2$)$_7$— | 1-Et-2-Pyrd |
| 2-28 | Hxd | Me | —NH.CO.O— | —(CH$_2$)$_7$— | 1,1-diEt-2-Pyrd$^+$ |
| 2-29 | Hpd | Et | —NH.CO.O— | —(CH$_2$)$_7$— | 3-Thi$^+$ |

TABLE 3

| Cpd No. | R$^a$ | R$^2$ | Y | D | Q |
|---|---|---|---|---|---|
| 3-1 | Ocd | Ac | —NH.CO.O— | —(CH$_2$)$_8$— | 1-Me-3-Imid$^+$ |
| 3-2 | Pnd | Isox | —NH.CO.O— | —(CH$_2$)$_8$— | 1-Me-1-Imid$^+$ |
| 3-3 | Hxd | 5-MeIsox | —NH.CO.O— | —(CH$_2$)$_8$— | 1-Me-1-Pyrd$^+$ |
| 3-4 | Hpd | 5-PhIsox | —NH.CO.O— | —(CH$_2$)$_8$— | 1-Me-1-Pip$^+$ |
| 3-5 | Ocd | Me | —CO.NH— | —(CH$_2$)$_9$— | 4-MeMor$^+$ |
| 3-6 | Pnd | Et | —CO.NH— | —(CH$_2$)$_9$— | 1-Me-2-Pyr$^+$ |
| 3-7 | Hxd | Ac | —CO.NH— | —(CH$_2$)$_9$— | 1-Me-3-Pyr$^+$ |
| 3-8 | Hpd | Isoz | —CO.NH— | —(CH$_2$)$_9$— | 3-Et-2-Thi$^+$ |
| 3-9 | Ocd | 5-MeIsox | —CO.NH— | —(CH$_2$)$_{10}$— | 3,4-diMe-5-Thi$^+$ |
| 3-10 | Pnd | 5-PhIsox | —CO.NH— | —(CH$_2$)$_{10}$— | 3-Thi$^+$ |
| 3-11 | Hxd | Me | —NH.CO— | —(CH$_2$)$_{11}$— | 1-Me-3-Imid$^+$ |
| 3-12 | Hpd | Et | —NH.CO— | —(CH$_2$)$_{12}$— | 1-Me-1-Imid$^+$ |
| 3-13 | Ocd | Ac | —NH.CO— | —(CH$_2$)$_{13}$— | 1-Me-1-Pyrd$^+$ |
| 3-14 | Pnd | Isox | —NH.CO— | —(CH$_2$)$_{14}$— | 1-Me-1-Pip$^+$ |
| 3-15 | Hxd | 5-MeIsox | —NH.CO— | —(CH$_2$)$_{11}$— | 4-MeMor$^+$ |
| 3-16 | Hpd | 5-PhIsox | —NH.CO— | —(CH$_2$)$_{11}$— | 1-Me-2-Pyr$^+$ |
| 3-17 | Hxd | Isox | —OP(O)(OH)O— | —(CH$_2$)$_3$— | 3-Thi$^+$ |
| 3-18 | Hxd | Isox | —OP(O)(OH)O— | —(CH$_2$)$_3$— | 1-Me-3-Imid$^+$ |
| 3-19 | Hpd | Et | —OP(O)(OH)O— | —(CH$_2$)$_2$— | 3-Et-2-Thi$^+$ |
| 3-20 | Hxd | Ac | —OP(O)(OH)O— | —(CH$_2$)$_3$— | 3,4-diMe-5-Thi$^+$ |
| 3-21 | Pnd | Me | —OP(O)(OH)O— | —(CH$_2$)$_3$— | 3-Thi$^+$ |
| 3-22 | Ocd | 5-MeIsox | —OP(O)(OH)O— | —(CH$_2$)$_3$— | 1-Me-3-Imid$^+$ |
| 3-23 | Pnd | 5-PhIsox | —OP(O)(OH)O— | —(CH$_2$)$_4$— | 1-Me-1-Imid$^+$ |
| 3-24 | Hxd | 2-Thi | —OP(O)(OH)O— | —(CH$_2$)$_4$— | 1-Me-1-Pyrd$^+$ |

TABLE 4

| Cpd No | R$^a$ | R$^2$ | Y | D | Q |
|---|---|---|---|---|---|
| 4-1 | Hpd | 2-Thi | —O.CO.NH— | —(CH$_2$)$_4$— | 3-Thi$^+$ |
| 4-2 | Ocd | Isox | —O.CO.NH— | —(CH$_2$)$_4$— | 1-Me-3-Imid$^+$ |
| 4-3 | Hpd | 5-MeIsox | —O.CO.NH— | —(CH$_2$)$_5$— | 3-Thi$^+$ |
| 4-4 | Hxd | 5-PhIsox | —O.CO.NH— | —(CH$_2$)$_5$— | 1-Me-1-Pyrd$^+$ |
| 4-5 | Hpd | 2-Thi | —O.CO.NAc— | —(CH$_2$)$_5$— | 1-Me-1-Pip$^+$ |
| 4-6 | Ocd | Isox | —O.CO.NAc— | —(CH$_2$)$_5$— | 4-MeMor$^+$ |
| 4-7 | Pnd | 5-MeIsox | —O.CO.NAc— | —(CH$_2$)$_6$— | 1-Me-2-Pyr$^+$ |
| 4-8 | Hxd | 5-PhIsox | —O.CO.NAc— | —(CH$_2$)$_6$— | 1-Me-3-Pyr$^+$ |
| 4-9 | Hpd | 2-Thi | O | —(CH$_2$)$_6$— | 1-Et-2-Thi$^+$ |
| 4-10 | Ocd | Isox | O | —(CH$_2$)$_7$— | 3,4-diMe-5-Thi$^+$ |
| 4-11 | Pnd | 5-MeIsox | O | —(CH$_2$)$_7$— | 3-Thi$^+$ |
| 4-12 | Hxd | 5-PhIsox | O | —(CH$_2$)$_7$— | 1-Me-3-Imid$^+$ |
| 4-13 | Hpd | 2-Thi | —OP(O)(OH)O— | —(CH$_2$)$_7$— | 1-Me-1-Imin$^+$ |
| 4-14 | Ocd | Isox | —OP(O)(OH)O— | —(CH$_2$)$_7$— | 1-Me-1-Pyrd$^+$ |
| 4-15 | Hpd | 5-MeIsox | —OP(O)(OH)O— | —(CH$_2$)$_2$— | 3-Thi$^+$ |
| 4-16 | Hpd | 5-PhIsox | —OP(O)(OH)O— | —(CH$_2$)$_2$— | 3-Thi$^+$ |
| 4-17 | Hpd | 2-Thi | —NH.CO.O— | —(CH$_2$)$_8$— | 1-Me-2-Pyr$^+$ |
| 4-18 | Ocd | Isox | —CO.NH— | —(CH$_2$)$_7$— | 1-Me-3-Pyr$^+$ |
| 4-19 | Pnd | 5-MeIsox | —NH.CO— | —(CH$_2$)$_7$— | 3-Et-2-Thi$^+$ |
| 4-20 | Hpd | Isox | —OP(O)(OH)O— | —(CH$_2$)$_2$— | —N$^+$Me$_3$ |
| 4-21 | Hpd | Isox | —OP(O)(OH)O— | —(CH$_2$)$_2$— | 1-Pyr$^+$ |
| 4-22 | Hpd | Isox | —OP(O)(OH)O— | —(CH$_2$)$_2$— | 3-Thi$^+$ |
| 4-23 | Hpd | Isox | —OP(O)(OH)O— | —(CH$_2$)$_2$— | 1-Me-3-Imid$^+$ |
| 4-24 | Hpd | Isox | —O.CO.NAc— | —CH$_2$— | 1-Et-2-Quin$^+$ |
| 4-25 | Hpd | Isox | —O.CO.NEt— | —CH$_2$— | 1-Et-2-Quin$^+$ |
| 4-26 | Hpd | Isox | —O.CO.NH— | —CH$_2$— | 2-Pyr |
| 4-27 | Hpd | Isox | —O.CO.NAc— | —CH$_2$— | 2-Pyr |
| 4-28 | Hpd | Isox | —O.CO.NAc— | —CH$_2$— | 1-Et-2-Pyr$^+$ |
| 4-29 | Hpd | Isox | —O.CO.NEt— | —CH$_2$— | 2-Et-2-Pyr$^+$ |
| 4-30 | Hpd | Isox | —OP(O)(OH)O— | —(CH$_2$)$_5$— | 3-Thi$^+$ |
| 4-31 | Hpd | Isox | —OP(O)(OH)O— | —(CH$_2$)$_6$— | 3-Thi$^+$ |

TABLE 5

| Cpd No. | R$^a$ | R$^2$ | Y | D | Q |
|---|---|---|---|---|---|
| 5-1 | Hpd | 2-Thi | —O.CO.NH— | —(CH$_2$)$_4$— | 3-Thi$^+$ |
| 5-2 | Ocd | Isox | —O.CO.NH— | —(CH$_2$)$_4$— | 1-Me-3-Imid$^+$ |
| 5-3 | Pnd | 5-MeIsox | —O.CO.NH— | —(CH$_2$)$_5$— | 1-Me-1-Imid$^+$ |
| 5-4 | Hxd | 5-PhIsox | —O.CO.NH— | —(CH$_2$)$_5$— | 1-Me-1-Pyrd$^+$ |
| 5-5 | Hpd | 2-Thi | —O.CO.NAc— | —(CH$_2$)$_5$— | 1-Me-1-Pip$^+$ |
| 5-6 | Ocd | Isox | —O.CO.NAc— | —(CH$_2$)$_5$— | 4-MeMor$^+$ |
| 5-7 | Pnd | 5-MeIsox | —O.CO.NAc— | —(CH$_2$)$_6$— | 1-Me-2-Pyr$^+$ |
| 5-8 | Hxd | 5-PhIsox | —O.CO.NAc— | —(CH$_2$)$_6$— | 1-Me-3-Pyr$^+$ |
| 5-9 | Hpd | 2-Thi | O | —(CH$_2$)$_6$— | 3-Et-2-Thi$^+$ |
| 5-10 | Ocd | Isox | O | —(CH$_2$)$_7$— | 3,4-diMe-5-Thi$^+$ |
| 5-11 | Pnd | 5-MeIsox | O | —(CH$_2$)$_7$— | 3-Thi$^+$ |
| 5-12 | Hxd | 5-PhIsox | O | —(CH$_2$)$_7$— | 1-Me-3-Imid$^+$ |
| 5-13 | Ocd | 2-Thi | —OP(O)(OH)O— | —(CH$_2$)$_2$— | —N$^+$Me$_3$ |
| 5-14 | Ocd | Isox | —OP(O)(OH)O— | —(CH$_2$)$_2$— | —N$^+$Me$_3$ |
| 5-15 | Ocd | Isox | —OP(O)(OH)O— | —(CH$_2$)$_2$— | 1-Pyr$^+$ |

TABLE 5-continued

| Cpd No. | R$^a$ | R$^2$ | Y | D | Q |
|---|---|---|---|---|---|
| 5-16 | Pnd | 5-MeIsox | —OP(O)(OH)O— | —(CH$_2$)$_8$— | 1-Me-1-Pip$^+$ |
| 5-17 | Hxd | 5-PhIsox | —OP(O)(OH)O— | —(CH$_2$)$_2$— | —N$^+$Me$_3$ |
| 5-18 | Hxd | 5-PhIsox | —OP(O)(OH)O— | —(CH$_2$)$_2$— | 1-Pyr$^+$ |
| 5-19 | Hpd | 2-Thi | —NH.CO.O— | —(CH$_2$)$_8$— | 1-Me-2-Pyr$^+$ |
| 5-20 | Ocd | Isox | —CO.NH— | —(CH$_2$)$_7$— | 1-Me-3-Pyr$^+$ |
| 5-21 | Pnd | 5-MeIsox | —NH.CO— | —(CH$_2$)$_9$— | 3-Et-2-Thi$^+$ |
| 5-22 | Hxd | 5-PhIsox | —OP(O)(OH)O— | —(CH$_2$)$_2$— | 3-Thi$^+$ |
| 5-23 | Hxd | Isox | —O.OC— | —(CH$_2$)$_2$— | —N$^+$Me$_3$ |
| 5-24 | Hxd | Isox | —OP(O)(OH)O— | —(CH$_2$)$_2$ | —N$^+$Me$_3$ |

In the compounds listed above, where the compound is shown as containing a quaternary nitrogen atom, then, except where a phosphate group is also present in the same compound, the compound must also contain an anion to balance the positive charge. Such an anion is not critical and may be chosen from any of the anions exemplified above in relation to Z$^-$.

Of the compounds listed above, preferred compounds are Compounds No. 1–4, 1–12, 1–13, 1–26, 1–47, 1–48, 1–51, 1–55, 1–56, 1–57, 1–58, 1–59, 1–60, 1–61, 1–62, 1–63, 1–64, 1–65, 1–66, 1–67, 4–3, 4–15, 4–16, 4–20, 4–21, 4–22, 4–23, 4–24, 4–25, 4–26, 4–27, 4–28, 4–29, 4–30, 4–31, 5–13, 5–14, 5–15, 5–17, 5–18, 5–22, 5–23 and 5–24, of which Compounds No. 1–4, 1–12, 1–60, 1–61, 1–63, 1–64, 4–3, 4–15, 4–22, 4–27 and 4–28 are most preferred.

The compounds of the present invention may be prepared by a variety of processes, for example by any of the following Methods A to G.

Method A

This method is for preparing a compound of general formula (I) in which Y is an oxygen atom, a sulfur atom or an optionally protected imino group, —NR$^3$, or for preparing its synthetic intermediate, the compound of formula (VI), as shown in the following reaction scheme:

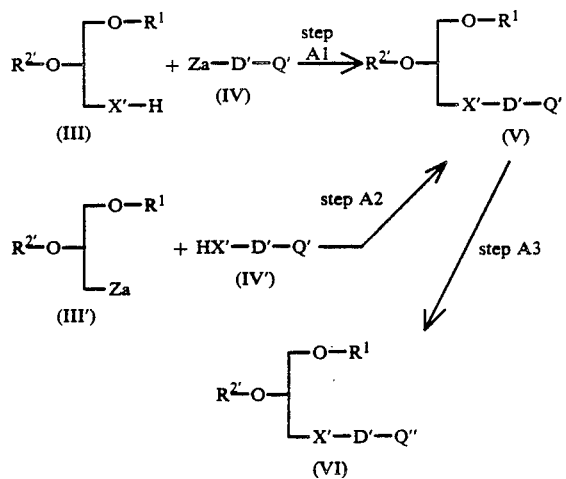

In the above formulae, R$^1$ is as defined above. R$^{2'}$ and D' represent any one of the groups represented by R$^2$ and D, respectively, but in which any reactive groups have been protected. X' represents an oxygen atom, a sulfur atom or an optionally protected imino group. Q' represents a group having the formula —O—R$^9$ [in which R$^9$ represents a hydroxy-Protecting group, for example: a tetrahydropyranyl or tetrahydrothiopyranyl group such as the tetrahydropyran-2-yl, 3-bromotetrahydropyran-2-yl, 4-methoxytetrahydropyran-4-yl, tetrahydrothiopyran-2-yl or 4-methoxytetrahydrothiopyran-4-yl groups; a lower alkoxymethyl group such as the methoxymethyl, t-butoxymethyl, 2-methoxyethoxymethyl, 2,2,2-trichloro- ethyoxymethyl or bis(2-chloroethoxy)methyl groups; or an aralkyl group such as the benzyl, p-methoxybenzyl, o-nitrobenzyl, p-nitrobenzyl, p-halobenzyl (e.g. p-chlorobenzyl or p-bromobenzyl group), p-cyanobenzyl, diphenylmethyl, triphenylmethyl, α-naphthyldiphenylmethyl, or p-methoxyphenyldiphenylmethyl groups, of which, we prefer the tetrahydropyranyl, lower alkoxymethyl and aralkyl groups] or any one of the heterocyclic groups defined above for Q in which, if neccesary, any reactive group is protected. Q" represents a group of formula Za or any one of heterocyclic groups defined for Q, in which Q is as defined above, and Za represents a halogen atom, a lower alkylsulfonyloxy group or an arylsulfonyloxy group.

In Steps A1 and A2, an ether, thioether or amino compound (V) is prepared by reaction of a compound of formula (III) or (IV') having a hydroxy group, a mercapto group or an optionally protected amino group at a terminal Position with an alkylating agent (IV) or (III') in the presence of a base.

The reaction is preferably effected in the presence of a solvent, the nature of which is not critical, provided that it does not interfere with the reaction. Examples of suitable solvents include: ethers, such as diethyl ether, tetrahydrofuran, or dioxane; aromatic hydrocarbons, such as benzene or toluene; amides, such as dimethylformamide or dimethylacetamide; dimethyl sulfoxide; or hexamethylphosphoric triamide; preferably benzene, dimethylformamide or hexamethylphosphoric triamide.

There is also no particular restriction on the nature of the base to be employed, provided that it does not affect other parts of the compounds. The base functions as an acid-binding agent and any base capable of fulfilling this function may be employed in the present invention, for example: organic bases, such as triethylamine, 1,5-diazabicyclo[5.4.0]undec-5-ene, pyridine, 2.6-lutidine, dimethylaniline or 4-(N,N-dimethylamino)Pyridine; alkali metal hydroxides, such as sodium hydroxide or potassium hydroxide; and alkali metal hydrides, such as sodium hydride or potassium hydride; of these, the alkali metal hydroxides are preferred.

The reaction will take place over a wide range of temperatures and the precise temperature chosen is not particularly critical. We generally find it convenient to conduct the reaction at a temperature from 0° C. to 150° C., more preferably at from 60° C. to 90° C. The time required for the reaction may vary widely, depending on many factors, notably the reaction temperature and the nature of the starting materials, but a period of from 1 hour to 3 days, more preferably from 4 to 16 hours, will normally suffice.

After completion of the reaction, the compound of formula (V) can be collected from the reaction mixture by conventional means. For instance, one suitable recovery technique comprises: adding an organic solvent immiscible with water to the reaction mixture; washing with water; and evaporating off the solvent. The desired compound thus obtained can be further purified, if necessary, by such conventional techniques as recrystallization, reprecipitation and the various chromatography techniques, notably column chromatography.

In Step A3, the desired compound of formula (VI) is prepared by converting the group of formula —O—$R^9$, when the compound of formula (V) contains this group as Q', into a group of formula Q''.

First, the hydroxy-protecting group, $R^9$, is removed. The nature of the reaction employed to remove this group will, of course, depend on the nature of the group to be removed. When the hydroxy protecting group is a tetrahydropyranyl group or a lower alkoxymethyl group, it can be removed by treatment with an acid in a solvent. Examples of suitable acids include, for example, acetic acid, p-toluenesulfonic acid, hydrochloric acid or a mixture of acetic acid and sulfuric acid. The reaction is preferably effected in the presence of a solvent, the nature of which is not critical, provided that it does not interfere with the reaction. Examples of suitable solvents include: alcohols, such as methanol or ethanol; ethers, such as tetrahydrofuran or dioxane; and mixtures of one or more of these organic solvents with water.

The reaction will take place over a wide range of temperatures and the precise temperature chosen is not particularly critical. We generally find it convenient to conduct the reaction at a temperature from 0° C. to 100° C., more preferably at from 20° C. to 60° C. The time required for the reaction may vary widely, depending on many factors, notably the reaction temperature and the nature of the starting materials, but a period of from 1 hour to 24 hours will normally suffice.

When the hydroxy-protecting group is an aralkyl group, it can be removed by contact with a reducing agent. For example, the reduction can be carried out by catalytic reduction at room temperature by using such a catalyst as palladium-on-carbon or platinum in the presence of hydrogen gas. This reaction is preferably effected in the presence of a solvent, the nature of which is not critical, provided that it does not interfere with the reaction. Examples of suitable solvents include: alcohols, such as methanol or ethanol; ethers, such as tetrahydrofuran or dioxane; fatty acids, such as acetic acid; and mixtures of one or more of these organic solvents with water.

The reaction will take place over a wide range of temperatures and the precise temperature chosen is not particularly critical. We generally find it convenient to conduct the reaction at a temperature from 0° C. to about room temperature. The time required for the reaction may vary widely, depending on many factors, notably the reaction temperature and the nature of the starting materials, especially the reducing agent, but a period of from 5 minutes to 12 hours will normally suffice.

After completion of the reaction, the desired compound can be isolated from the reaction mixture by to conventional means. The product may then, if desired, be further purified by such conventional techniques as recrystallization, preparative thin layer chromatography or column chromatography.

Next, the deprotected hydroxy group is subjected to acylation, for example, methanesulfonylation, toluenesulfonylation, trifluoromethanesulfonylation or trifluoroacetylation, to convert into an ester, or it is halogenated.

The ester synthesis is preferably effected in the presence of a solvent, the nature of which is not critical, provided that it does not interfere with the reaction. Examples of suitable solvents include: halogenated hydrocarbons, particularly halogenated aliphatic hydrocarbons, such as chloroform, methylene chloride, or dichloroethane; ethers, such as diethyl ether, tetrahydrofuran or dioxane; and aromatic hydrocarbons, such as benzene or toluene. Of these, methylene chloride or benzene are preferred.

The reaction is preferably effected in the presence of a base, the nature of which is not critical, provided that it does not affect other Parts of the compounds. The base functions as an acid-binding agent and any base capable of fulfilling this function ma be employed in the present invention, for example: organic bases, such as triethylamine, pyridine, 2,6-lutidine or dimethylaniline.

The reaction will take place over a wide range of temperatures and the precise temperature chosen is not particularly critical. We generally find it convenient to conduct the reaction at a temperature from 0° C. to 25° C. The time required for the reaction may vary widely, depending on many factors, notably the reaction temperature and the nature of the starting materials, but a period of from 30 minutes to 24 hours will normally suffice.

The nature of the halogenation reaction is not critical, provided that it can replace a hydroxy group by a halogen atom. In general, it is preferably carried out using a carbon tetrahalide and triphenylphosphine, or a phosphorus trihalide.

The reaction is preferably effected in the presence of a solvent, the nature of which is not critical, provided that it does not interfere with the reaction. Examples of suitable solvents include: halogenated hydrocarbons, particularly halogenated aliphatic hydrocarbons, such as chloroform, methylene chloride or dichloroethane; and nitriles, such as acetonitrile.

The reaction will take place over a wide range of temperatures and the precise temperature chosen is not particularly critical. We generally find it convenient to conduct the reaction at a temperature from −25° C. to room temperature. The time required for the reaction may vary widely, depending on many factors, notably the reaction temperature and the nature of the starting materials, but a period of from .1 to 60 minutes will normally suffice.

The halogen-substituted compound can be also synthesized by reaction of the ester synthesized as described above with an alkali metal halide, such as sodium iodide, sodium bromide or Potassium chloride. The reaction is preferably effected in the presence of a solvent, the nature of which is not critical, provided that it does not interfere with the reaction. It is preferably a polar solvent capable of dissolving an alkali metal halide. Examples include: ketones, such as acetone; sulfoxides, such as dimethyl sulfoxide; amides, such as dimethylformamide; and phosphorus triamides, such as hexamethylphosphoric triamide. Of these, we prefer dimethylformamide.

The reaction will take place over a wide range of temperatures and the precise temperature chosen is not particularly critical. We generally find it convenient to conduct the reaction at a temperature from 20° C. to 80° C. The time required for the reaction may vary widely, depending on many factors, notably the reaction temperature and the nature of the starting materials, but a period of from 1 to 24 hours will normally suffice.

After completion of the reaction, the desired compound can be isolated from the reaction mixture by conventional means. The product may then, if desired, be further purified by such conventional techniques as recrystallization, preparative thin layer chromatography and column chromatography.

Method B

Compounds of the invention and their synthetic intermediates containing a phosphoric acid group, i.e. compounds of formula (IX), can be prepared as illustrated by the following reaction scheme:

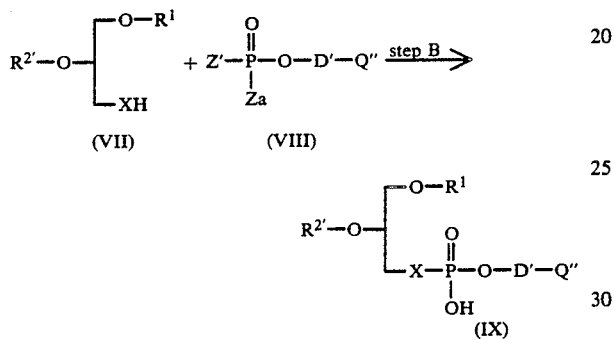

(VII)    (VIII)

(IX)

In the above formulae, $R^1$, $R^{2'}$ X, D', Za and Q" are as defined above. Z' represents a halogen atom.

In this method, a phosphate ester or a phosphate thioester compound of formula (IX) is prepared by condensation of compound of formula (VII) having a terminal hydroxy group or a mercapto group with a phosphoric acid dihalide (VIII) in a solvent in the presence of a base followed by treatment with water.

There is no particular restriction on the nature of the solvent to be employed, provided that it does not interfere with the reaction and that it can dissolve the starting materials at least to some extent. Examples of preferred solvents include halogenated hydrocarbons, particularly halogenated aliphatic hydrocarbons, such as methylene chloride, chloroform or 1,2-dichloroethane; ethers, such as diethyl ether, tetrahydrofuran or dioxane; and aromatic hydrocarbons, such as benzene or toluene.

There is also no particular restriction on theature of the base to be employed, provided that it does not interfere with other parts of the molecule. It is preferably an amine, for example, triethylamine, diethylamine or pyridine.

The reaction will take place over a wide range of temperatures and the precise temperature chosen is not particularly critical. We generally find it convenient to conduct the reaction at a temperature from 0° C. to 120° C. The time required for the reaction may vary widely, depending on many factors, notably the reaction temperature and the nature of the starting materials and base employed, but a period of from 2 to 24 hours will normally suffice.

After completion of the reaction, the desired compound of formula (IX) can be isolated from the reaction mixture by conventional means. For example, after condensation of the reaction mixture, the purified compound can be obtained from the residue by such well known purification methods as silica gel chromatography and recrystallization.

Method C

In this method, there is prepared a compound of the invention and its synthetic intermediate in which Y represents a group of formula —X'—CO—, that is to say a compound of formula (XI), as illustrated in the following reaction scheme:

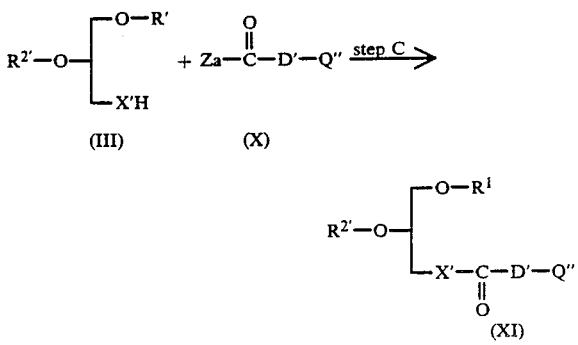

(III)    (X)

(XI)

In the above formulae, $R^1$, $R^{2'}$, X', Za, D' and Q" are as defined above.

In this reaction, there is prepared a compound of formula (XI), which is an ester, a thioester or an optionally protected amide, by reaction of compound of formula (III), which has a terminal hydroxy, mercapto or optionally protected amino group with a reactive derivative of a carboxylic acid of formula (X), in the presence or absence of a base.

When Za represents a halogen atom, the reaction can be conducted in a similar manner to that described in Method B.

When Za represents a lower alkylsulfonyloxy group or an arylsulfonyloxy group, the reaction does not always require a base to proceed immediately but the use of a base accelerates the reaction rate.

There is no particular restriction on the nature of the solvent to be employed, provided that it does not interfere with the reaction and that it can dissolve the starting materials at least to some extent. Examples of preferred solvents include: halogenated hydrocarbons, particularly halogenated aliphatic hydrocarbons, such as chloroform, methylene chloride or dichloroethane; and ethers, such as diethyl ether, tetrahydrofuran or dioxane. Of these, methylene chloride or tetrahydrofuran is preferred.

The reaction will take place over a wide range of temperatures and the precise temperature chosen is not particularly critical We generally find it convenient to conduct the reaction at a temperature from 0° C. to 50° C., preferably from 0° to 20° C. The time required for the reaction may vary widely, depending on many factors notably the reaction temperature and the nature of the starting materials and base employed, but a period of from 30 minutes to 24 hours will normally suffice.

After completion of the reaction, the desired compound can be separated from the reaction mixture by conventional means. For example, the purified compound can be obtained by such well known purification methods such as recrystallization, preparative thin layer chromatography and column chromatography.

Method D

In this method there are prepared compounds of the present invention and their synthetic intermediates in which Y represents a group of formula —X—CO—R$^{4'}$, that is to say a compound of formula (XIII), as illustrated by the following reaction scheme:

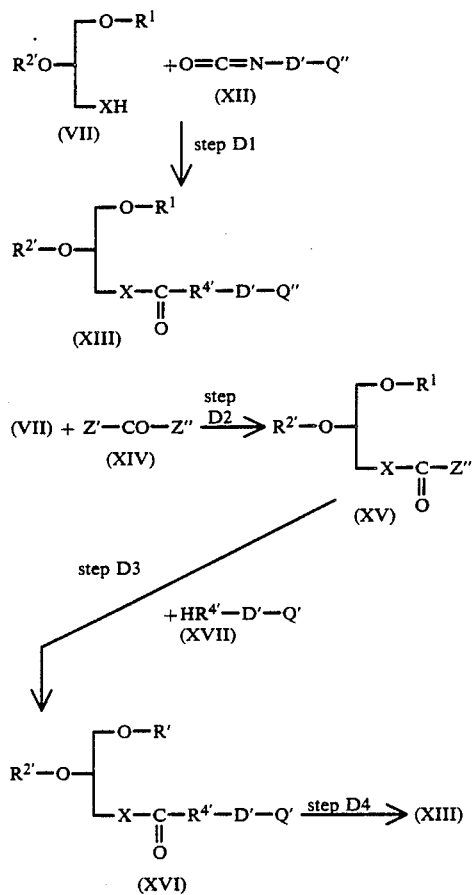

In the above formulae, R$^1$, R$^{2'}$, X, D', Z' and Q'' are as defined above. R$^{4'}$ represents an optionally substituted imino group. Z'' represents a leaving group, such as a halogen atom, a benzyloxy group or a trihalomethoxy group (e.g. trichloromethoxy).

In Step D1, a carbamate or thiocarbamate is prepared by reaction of a compound of formula (VII), which has a terminal hydroxy or mercapto group, with an isocyanate compound of formula (XII), followed, if desired, by substitution of the imino group to prepare a compound of formula (XIII) from the resulting carbamate or thiocarbamate.

The isocyanate compound of formula (XII) can be synthesized without difficulty, for example, by allowing a compound having the formula HOOC—D'—Q'' (in which D' and Q'' are as defined above) to react with DPPA (diphenylphosphoryl azide) in an inert solvent, such as chloroform, toluene, benzene, methylene chloride or tetrahydrofuran, preferably toluene or benzene, and in the presence of an organic base, such as triethylamine or tributylamine at from 0° C. to 150° C. The desired compound of formula (XIII) can be prepared directly by adding the compound of formula (VII) to a solution of the compound of formula (XII) obtained as described above and then heating for 2 to 24 hours at 60° C. to 150° to react further. Preferably, the compound of formula (XII) at the time of its synthesis is washed with a saturated aqueous solution of sodium bicarbonate and with water in order to remove the phosphorus compound then, after removal of the solvent, dried, dissolved in any desired one of the solvents mentioned above (preferably toluene) and mixed with the compound of formula (VII) to react.

The imino-substitution reaction can be achieved by reaction with, for example, an alkyl halide, a carboxylic acid halide or a carboxylic acid anhydride in the presence of a base.

The reaction is preferably effected in the presence of a solvent, the nature of which is not critical, provided that it does not interfere with the reaction. Examples of suitable solvents include: aromatic hydrocarbons, such as benzene or toluene; and pyridine.

There is also no particular restriction on the nature of the base to be employed, provided that it does not interfere with other parts of the molecule. It is preferably: an organic base, e.g. an amine, for example, triethylamine, diisopropylethylamine, 4-(N,N-dimethylaminopyridine or pyridine; or an inorganic base, e.g. an alkali metal hydride, for example sodium hydride or potassium hydride.

The reaction will take place over a wide range of temperatures and the precise temperature chosen is not particularly critical. We generally find it convenient to conduct the reaction at a temperature from 20° C. to 120° C. The time required for the reaction may vary widely, depending on many factors, notably the reaction temperature and the nature of the starting materials and base employed, but a Period of from 1 to 24 hours will normally suffice.

After completion of the reaction, the desired compound can be isolated from the reaction mixture by conventional means. For example, the purified compound can be obtained by such purification methods as recrystallization, preparative thin layer chromatography and column chromatography.

Alternatively, a compound of formula (XV) may be prepared by reacting a compound of formula (VII), which has a terminal hydroxy or mercapto group, with a compound of formula (XIV) in the presence of an organic base; a carbamate or thiocarbamate compound of formula (XVI) may be prepared by reaction of the resulting compound of formula (XV), after isolation or without isolation, with an amine compound (XVII) in the presence of an organic base.

There is no particular restriction on the nature of the solvent to be employed, provided that it does not interfere with the reaction and that it can dissolve the starting materials at least to some extent. Examples of preferred solvents include: halogenated hydrocarbons, such as methylene chloride or chloroform; aromatic hydrocarbons, such as benzene, toluene or xylene; and ethers, such as tetrahydrofuran or dioxane.

There is also no particular restriction on the nature of the base to be employed, provided that it does not interfere with other parts of the molecule. It is preferably an organic base, e.g. an amine, for example, triethylamine, 1,5-diazabicyclo[5.4.0]undec-5-ene, pyridine 2 6-lutidine, dimethylaniline or 4-(N,N-dimethylamino)pyridine.

The reaction will take place over a wide range of temperatures and the precise temperature chosen is not particularly critical. We generally find it convenient to conduct the reaction at a temperature from 0° C. to 100° C., preferably from 0° C. to 50° C. The time required for the reaction may vary widely, depending on many factors, notably the reaction temperature and the nature of the starting materials and base employed, but a period of from 30 minutes to 24 hours will normally suffice for both Steps D2 and D3.

After completion of the reaction, the desired compound can be isolated from the reaction mixture by conventional means. For example, the purified compound can be obtained by such purification methods as recrystallization, preparative thin layer chromatography and column chromatography.

In Step D4, a carbamate or thiocarbamate compound of formula (XIII), is prepared when the compound of formula (XVI) contains a group having the formula —O—$R^9$ (in which $R^9$ is as defined above) represented by Q' in its molecule, by converting the —O—$R^9$ group into a group of formula Za. The reaction can be carried out in a similar manner to those in Step A3.

Method E

Compounds of formulae (XIX) and (XX) may be prepared as illustrated by the following reaction scheme:

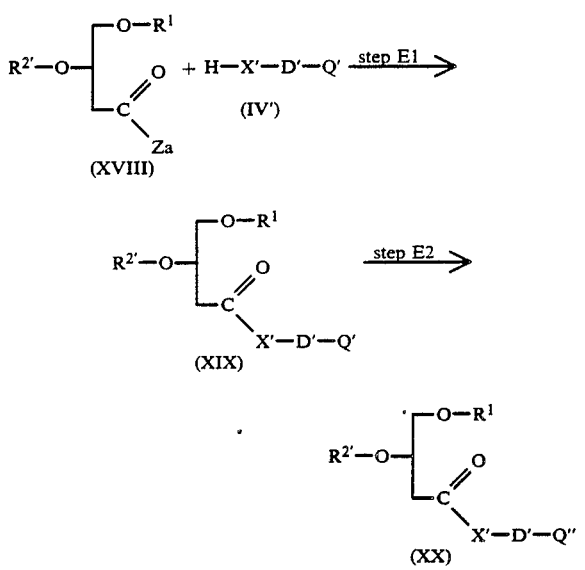

In this method, an ester, a thioester or an optionally substituted amide compound (XIX) is prepared by reacting a reactive derivative of a carboxylic acid of formula (XVIII) to react with a compound of formula (IV') having a terminal hydroxy, mercapto or optionally substituted amino group, in the presence of a base. The reaction is conducted in a similar manner to that described in Step C (Method C).

In Step E2, a compound of formula (XX) is prepared, when the compound of formula (XIX) contains a group having the formula —O—$R^9$ (in which $R^9$ is as defined above) represented by Q' in its molecule, by converting the —O—$R^9$ group into a group of formula Za. The reaction can be carried out in a similar manner to that described in Step A3.

Method F

Compounds of formulae (XXIII) and (XXIV) may be prepared as illustrated by the following reaction scheme:

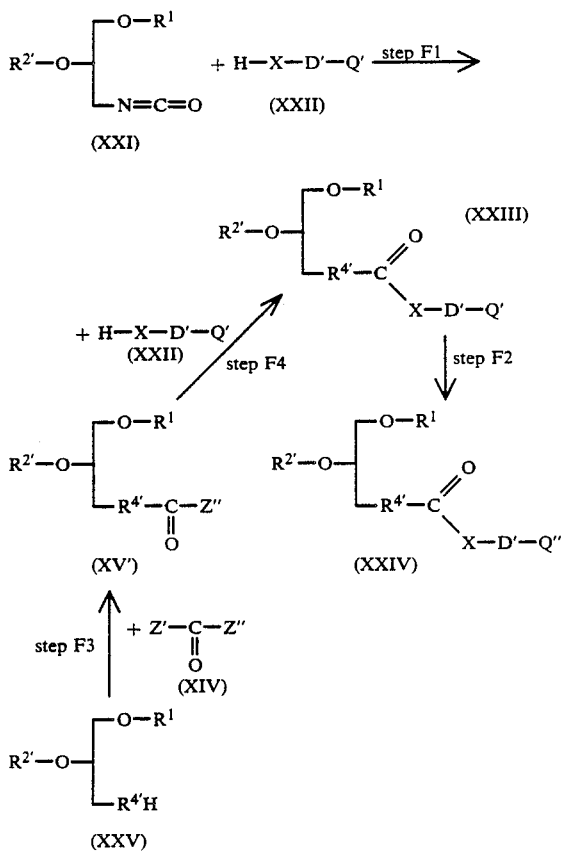

In this method, a carbamate or thiocarbamate compound of formula (XXIII) is prepared in Step F1 by reaction of an isocyanate compound (XXI) with a compound of formula (XXII) which has a terminal hydroxy group or mercapto group in its molecule, followed by, if desired, substituting the imino group. The reaction can be carried out in a similar manner to that described in Step D1.

In Step F2, a carbamate or thiocarbamate compound of formula (XXIV) is prepared, when the compound of formula (XXIII) contains a group having the formula —O—$R^9$ (in which $R^9$ is as defined above) represented by Q' in its molecule, by converting the —O—$R^9$ group into a group of formula Za followed by, if desired, substituting the imino group, as described in Step D1. The reaction can be carried out in a similar manner to that described in Step D4.

In Steps F3 and F4, a compound of formula (XV') is prepared by reaction of an amine compound of formula (XXV) with a compound of formula (XIV) in the presence of an organic base; subsequently, a carbamate or thiocarbamate compound of formula (XXIII) is prepared by reaction of this compound of formula (XV'), after isolation or without isolation, with a compound of formula (XXII) which has a terminal hydroxy group or mercapto group in its molecule, in the presence of an organic base. The reactions can be carried out in a similar manner to those described in Step D2 and Step D3.

Method G

In this method, a compound of formula (I) of this invention is prepared by reacting a compound of formula (VI), (IX), (XI), (XIII), (XX) or (XXIV), which may have been prepared as described above, when Q" represents a group having the formula Za (in which Za is as defined above), with an amine compound of formula (XXVI) or (XXVI'), and then, if desired, by deprotection of the protecting group of $R^{2'}$, deprotection of the carboxy-protecting group in the group D and/or deprotection of the imino-protecting group, for example as illustrated by the following reaction:

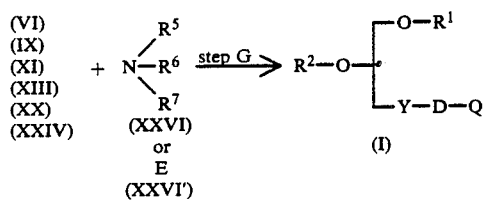

In the above formulae, $R^1$, $R^2$, $R^5$, $R^6$, $R^7$, Y, D and Q are as defined above and E represents a heterocyclic compound corresponding to the definition of Q.

The reaction is preferably effected in the presence of a solvent. There is no particular restriction on the nature of the solvent to be employed, provided that it does not interfere with the reaction and that it can dissolve the starting materials at least to some extent. Examples of preferred solvents include: aromatic hydrocarbons, such as benzene, toluene or xylene; halogenated hydrocarbons, particularly halogenated aliphatic hydrocarbons, such as methylene chloride or chloroform; lower alcohols, such as methanol, ethanol or isopropanol; amides, such as dimethylformamide; ethers, such as diethyl ether, tetrahydrofuran or dioxane; acetonitrile; water; or a mixture of any 2 or more, e.g. 2 to 3, of these solvents such as a mixture of chloroform, dimethylformamide and isopropanol, e.g. in a volume ratio of about 3:5:5. Of these, a mixture of chloroform, dimethylformamide and isopropanol or an aromatic hydrocarbon are preferred.

The reaction will take place over a wide range of temperatures and the precise temperature chosen is not particularly critical. We generally find it convenient to conduct the reaction at a temperature from 20° C. to 80° C. The time required for the reaction may vary widely, depending on many factors, notably the reaction temperature and the nature of the starting materials and base employed, but a period of from 1 to 48 hours will normally suffice. The reaction is preferably carried out in a nitrogen atmosphere and in a sealed reactor (e.g. a sealed tube), when gaseous amines are employed.

Removal of the protecting groups can be carried out by conventional means, the precise reaction chosen depending upon the nature of the protecting group to be removed.

When a hydroxy-protecting group is an aralkyl group, it can be removed by contact with a reducing agent. For example, the deprotection may be performed by catalytic reduction using a catalyst such as palladium-on-carbon or platinum at room temperature in the presence of hydrogen. The reaction is normally carried out in the presence of a solvent. There is no particular restriction on the nature of the solvent to be employed, provided that it does not interfere with the reaction and that it can dissolve the starting materials at least to some extent. Examples of preferred solvents include: alcohols, such as methanol or ethanol; ethers, such as tetrahydrofuran or dioxane; fatty acids, such as acetic acid; or a mixture of any one or more thereof with water.

The reaction will take place over a wide range of temperatures and the precise temperature chosen is not particularly critical. We generally find it convenient to conduct the reaction at a temperature from 0° C. to about room temperature. The time required for the reaction may vary widely, depending on many factors, notably the reaction temperature and the nature of the starting materials and base employed, but a period of from 5 minutes to 12 hours will normally suffice.

When the hydroxy-protecting group is a lower aliphatic acyl group or an aromatic acyl group, it can be removed by treatment with a base in the presence of an aqueous solvent. There is no particular limitation on the solvent to be employed, provided that it may be used in hydrolysis and preferred examples include: water and mixtures of water and an organic solvent, for example, an alcohol such as methanol or ethanol, or an ether such as tetrahydrofuran or dioxane. There is no particular restriction on the base to be employed, provided that it does not affect any other part of the compound, and the reaction is preferably carried out by using an alkali metal carbonate (such as sodium carbonate or potassium carbonate) or ammonia. The reaction temperature is not particularly critical, but in order to control side reactions, the reaction is preferably carried out from 0° C. to about room temperature. The time required for the reaction may vary widely, depending on many factors, notably the reaction temperature and the nature of the starting materials and base employed, but a period of from 1 to 6 hours will normally suffice.

Occasionally, the procedure used for removing the hydroxy-protecting groups mentioned above may also removed the imino-protecting and/or carboxy protecting groups at the same time.

After completion of the reaction, the desired compound can be isolated from the reaction mixture by conventional means. For example, the purified compound can be obtained by such well known purification methods as recrystallization, preparative thin layer chromatography and column chromatography.

When the carboxy-protecting group is a lower alkyl group, it can be removed by treatment with a base. The reaction conditions are the same as for the removal of the hydroxy protecting group when it is a lower aliphatic acyl group or an aromatic acyl group as described above.

When the carboxy-protecting group is an aralkyl group or a halogenated lower alkyl group, it can be removed by contact with a reducing agent. The preferred reducing agent is: zinc-acetic acid if the carboxyl group is protected by a halogenated lower alkyl group; and catalytic reduction using a catalyst such as palladium-on-carbon or platinum in the presence of hydrogen, if it is protected by an aralkyl group. These reactions are normally carried out in the presence of a solvent. There is no particular restriction on the nature of the solvent to be employed, provided that it does not interfere with the reaction and that it can dissolve the starting materials at least to some extent. Examples of preferred solvents include: alcohols, such as methanol or ethanol; ethers, such as tetrahydrofuran or dioxane; fatty acids, such as acetic acid; and mixtures of any one or more thereof with water.

These reactions will take place over a wide range of temperatures and the precise temperature chosen is not particularly critical. We generally find it convenient to conduct the reactions at a temperature from 0° C. to about room temperature. The time required for the reaction may vary widely, depending on many factors, notably the reaction temperature and the nature of the starting materials and base employed, but a period of from 5 minutes to 12 hours will normally suffice.

When the carboxy-protecting group is an alkyloxymethyl group, it can be removed by treatment with an acid. Preferred acids include: hydrochloric acid; and mixtures of acetic acid with sulfuric acid. The reaction is normally carried out in the presence of a solvent. There is no particular restriction on the nature of the solvent to be employed, provided that it does not interfere with the reaction and that it can dissolve the starting materials at least to some extent. Examples of preferred solvents include: alcohols, such as methanol or ethanol; ethers, such as tetrahydrofuran or dioxane; and mixtures of any one or more thereof with water.

The reaction will take place over a wide range of temperatures and the precise temperature chosen is not particularly critical. We generally find it convenient to conduct the reaction at a temperature from 0° C. to 50° C. The time required for the reaction may vary widely, depending on many factors, notably the reaction temperature and the nature of the starting materials and base employed, but a period of from 10 minutes to 18 hours will normally suffice.

Occasionally, the procedure for removing the carboxy-protecting group mentioned above may also remove the hydroxy-protecting and/or imino-protecting groups at the same time.

After completion of the reaction, the desired compound can be separated from the reaction mixture by conventional means. For example, one suitable recovery technique comprises: after filtering off the insoluble material which separates from the reaction mixture, the organic layer is washed with water; it is then dried; and the organic solvent is distilled off. The compound can, if desired, be further purified by such conventional purification methods as recrystallization, preparative thin layer chromatography and column chromatography.

When the imino-protecting group is a lower aliphatic acyl group, an aromatic acyl group or an alkyloxycarbonyl group, it can be removed by treatment with a base. The reaction conditions are the same as for the removal of the hydroxy-protecting group when it is a lower aliphatic acyl group or an an aromatic acyl group as described above.

When the imino-protecting group is an alkenyloxycarbonyl group, it can be removed by treatment with a base in a similar manner to the deprotection of the hydroxy-protecting group when it is a lower aliphatic acyl group or an aromatic acyl group. However, particularly when the imino-protecting group is an allyloxycarbonyl group, deprotection using palladium and triphenylphosphine or nickeltetracarbonyl is more convenient and takes place with fewer side reactions.

Occasionally, the procedures for removing the imino-protecting group mentioned above may also remove the carboxy-protecting and/or hydroxy-protecting groups at the same time.

After completion of the reaction, the desired compound can be separated from the reaction mixture by conventional means. For example, the purified compound can be obtained by such well known purification methods as recrystallization, preparative thin layer chromatography and column chromatography.

The order of the deprotection reactions of the hydroxy-protecting and imino-protecting groups is not necessarily fixed and can be carried out in a desired order.

When Y represents a group having the formula —X—P(O)(OH)—O— (in which X is as defined above) and Q represents a group containing an ammonio moiety, for example —$N^+R^5R^6R^7 \cdot Z^-$ (in which $Z^-$, $R^5$, $R^6$ and $R^7$ are as defined above) in the compounds of general formula (I), the compound in which 13 Y—D—Q represents the group of formula (IIa) can be obtained as its pure inner salt by condensation of the reaction mixture and then purification of the residue by silica gel chromatography followed finally by treatment with an ion exchange resin (e.g. MB-3 of Rohm & Haas Co.) or with a silver salt (e.g. silver carbonate or silver acetate). When pyridine is employed as a reagent or solvent, the inner salt may be obtained directly.

In addition, the inner salt can be converted easily into a salt with another ion by known methods.

If desired, the hydroxy group and/or carboxyl group can be protected again by any one of the protecting groups capable of being hydrolyzed in vivo and referred to above. This reaction may be carried out by conventional means well known in this field. For example, an ester derivative in which the carboxyl group is protected by a protecting group capable of being hydrolyzed in vivo can be prepared by reaction with an aliphatic acyloxymethyl halide such as acetoxymethyl chloride, propionyloxymethyl bromide or pivaloyloxymethyl chloride; a lower alkyloxycarbonyloxyethyl halide such as 1-methoxycarbonyloxyethyl chloride or 1-ethoxycarbonyloxyethyl iodide; a phthalidyl halide; or a (2-oxo-5-methyl-1,3-dioxolen-4-yl)methyl halide at 0° C. to 50° C. The reaction is normally carried out in the presence of a solvent. There is no particular restriction on the nature of the solvent to be employed, provided that it does not interfere with the reaction and that it can dissolve the starting materials at least to some extent. Examples of preferred solvents include polar solvents, such as dimethylformamide.

The reaction will take place over a wide range of temperatures and the precise temperature chosen is not particularly critical. We generally find it convenient to conduct the reaction at a temperature from 0° C. to 100° C. The time required for the reaction may vary widely, depending on many factors, notably the reaction temperature and the nature of the starting materials and base employed, but a period of from 30 minutes to 10 hours will normally suffice.

When Q' or Q" represents a heterocyclic group as defined for Q, each of compounds (VI), (IX), (XI), (XIII), (XVI), (XX) and (XXIII) represents a compound of formula (I) of this invention. However, if desired, the protecting groups may be removed in a similar manner to that described in Step G, and, if desired, the deprotected groups may be protected again by protecting groups capable of being hydrolyzed in vivo in order to prepare corresponding compounds of formula (I).

Compounds of formulae (III), (VII), (XVIII), (XXI) and (XXV) employed in the above methods as starting materials are novel compounds, and each of them can be prepared as racemates or as single enantiomers from known racemic mixtures (XXVII) and known optically active compounds (XXVII) or its antipode, respectively, for example by the reaction steps shown below:
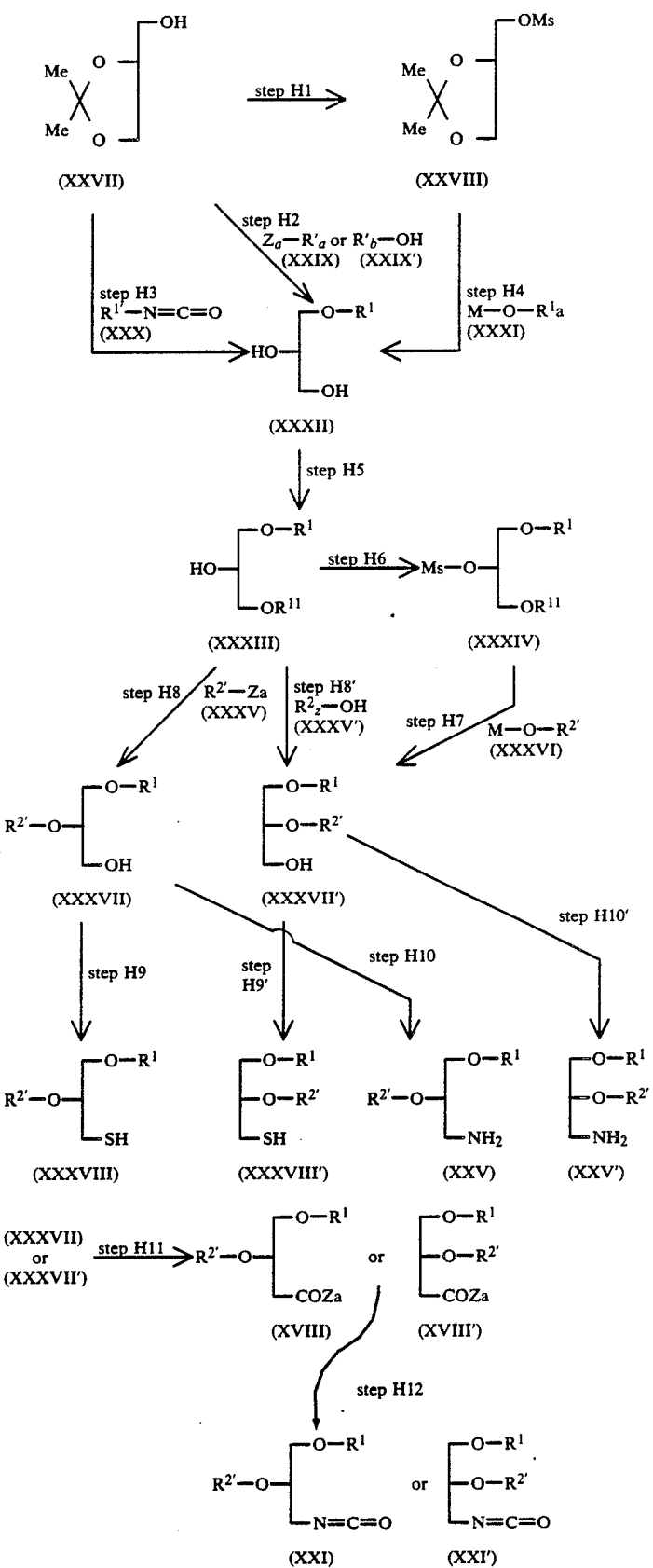

In these formulae, $R^1$, $R^{2'}$, Za and M are as defined above. $R^{1'}$ represents any one of the $C_8$–$C_{22}$ alkyl groups defined above in relation to $R^1$. R'a represents a $C_8$–$C_{22}$ alkyl group or a heterocyclic group as defined for $R^1$, R'b represents a heterocyclic group as defined for $R^1$ and $R^2$a represents a heterocyclic group as defined for $R^2$. Me represents a methyl group. Ms indicates a mesyl group and $R^{11}$ represents a hydroxy-protecting group which is not particularly critical provided that it may be used as hydroxy-protecting group and preferably is a triphenylmethyl group or a silyl group such as t-butyldimethylsilyl or t-butyldiphenylsilyl.

In Step H2, a compound of formula (XXXII) is prepared by reacting a glycerol derivative of formula (XXVII) with a compound of formula (XXIX) or (XXIX') in order to modify the hydroxy group at position 1 of glycerol with a group $R^1$, followed by removal of the protecting groups at position 2 and position 3.

The reaction with the compound of formula (XXIX) is carried out in the same manner as described above in relation to Step A1, and the reaction with the compound of formula (XXIX') is carried out in an inert solvent in the presence of a di($C_1$–$C_6$ alkyl) azodicarboxylate (e.g. dimethyl azodicarboxylate or diethyl azodicarboxylate) and a triaryl phosphine (e.g. triphenylphosphine or tritolylphosphine). There is no particular restriction on the nature of the solvent to be employed, provided that it does not interfere with the reaction, and examples of suitable solvents include: aromatic hydrocarbons, such as benzene, toluene and xylene; and ethers, such as diethyl ether or tetrahydrofuran.

The reaction will take place over a wide range of temperatures and the precise temperature chosen is not particularly critical. We generally find it convenient to conduct the reaction at a temperature from 0° C. to 100° C. The time required for the reaction may vary widely, depending on many factors, notably the reaction temperature and the nature of the starting materials and base employed, but a period of from 15 minutes to 5 hours will normally suffice.

The removal of the protecting group may be carried out in the same manner as in the removal of $R^9$ in Step A2 when $R^9$ is a tetrahydropyranyl group or a lower alkyloxymethyl group. Step H8 is also a similar one, when the compound of formula (XXIX) is employed as a reagent.

In Step H3, a compound of formula (XXXII) is prepared by reacting a glycerol derivative of formula (XXVII) with an isocyanate compound of formula (XXX) in order to convert the hydroxyl group at position 1 of glycerol into a carbamate group, followed by removal of the protecting groups at position 2 and position 3. The former reaction is carried out in a similar manner to that in Step D1 and the latter reaction is carried out in a similar manner to the removal of the protecting group in Step H2.

In Step H4, a compound of formula (XXXII) is prepared by reacting a 1-mesyl derivative of glycerol (XXVIII) with a metal alkoxide compound (XXXI), followed by removal of the protecting groups at position 2 and position 3. The reaction is preferably effected in the presence of a solvent, the nature of which is not critical, provided that it does not participate in the reaction, and examples include: aromatic hydrocarbons, such as benzene or toluene; amides, such as dimethylformamide or dimethylacetamide; and dimethyl sulfoxide; preferably benzene or dimethylformamide. The reaction temperature is not particularly critical and, for instance, the reaction may be carried out at from 0° C. to 120° C., preferably at from 70° C. to 120° C. Though it may vary, depending on the reaction temperature and starting compounds, the reaction normally requires from 1 to 24 hours.

Deprotection of the protecting group can be performed in the same way as that described in Step H2.

In Step H5, a compound of formula (XXXIII) is prepared by selective protection of the primary hydroxyl group at position 3 of compound (XXXI) by using a triphenylmethyl halide or a silyl halide such as a t-butyldimethylsilyl halide or a t-butyldiphenylsilyl halide in the presence of a base.

When a triphenylmethyl halide is used for protection, the solvent employed is not particularly critical and is preferably a halogenated hydrocarbon such as chloroform, methylene chloride or dichloroethane or an aromatic hydrocarbon such as benzene or toluene. As the base employed, although not particularly critical, provided it is an organic base, triethylamine or pyridine are preferred. The reaction is carried out at from 0° C. to 130° C. requiring from 1 to 24 hours.

When a silyl halide is used for protection, the solvent employed is not particularly critical and is preferably an ether such as diethyl ether, tetrahydrofuran or dioxane or an amide such as dimethylformamide. As the base employed, although not particularly critical, provided it is an organic base, imidazole is preferred. The reaction is carried out at from 0° C. to 50° C., requiring from 1 to 24 hours.

In Step H6, a compound of formula (XXXIV) is prepared by mesylation of the secondary hydroxy group at position 2 of the compound of formula (XXXIII) and this can be carried out in the same manner as mentioned in the latter reaction of Step A2. Step H1 is similar.

In Step H7, a compound having an inverted configuration at position 2 is prepared by reacting a 2-mesyl derivative of glycerol (XXXIV) with a metal alkoxide compound (XXXVI), and then the hydroxy-protecting group at position 3 is removed. The former reaction is carried out in a similar manner to Step H4, and the latter deprotection is achieved by any conventional method.

In Step H8', compound of formula (XXXVII') having an inverted configuration is prepared by reacting a compound of formula (XXXIII) with a compound of formula (XXXV'). This reaction may be carried out in a similar manner to that described in relation to Step H2 when a compound of formula (XXIX') is employed as a reagent.

Steps H9 and H9' are for preparing a compound of formula (XXXVIII) from a compound of formula (XXXVII) and compound (XXXVIII') from a compound of formula (XXXVII'), respectively, by acylation, for example methanesulfonylation, toluenesulfonylation, trifluoromethanesulfonylation or trifluoroacetylation, to prepare an ester, and then allowing the resulting ester to react with an alkali metal thioacetate (e.g. sodium thioacetate) to convert the acyloxy group into a protected mercapto group; and finally by removing the mercapto-protecting group by using a base such as an alkali metal alkoxide. The reaction is carried out at −30° C. to 25° C., requiring from 0.5 to 24 hours.

In Steps H10 and H10', an amino compound of formula (XXV) is prepared from a compound of formula (XXXVII) and an amino compound of formula (XXV')

is prepared from a compound of formula (XXXVII'), respectively by acylation, for example methanesulfonylation, toluenesulfonylation, trifluoromethanesulfonylation or trifluoroacetylation, to prepare an ester; then allowing the resulting ester to react with an alkali metal azide (e.g. sodium azide) in dimethylformamide at 0° C. to 80° C. for 1 to 24 hours to introduce an azido group into position 3; and then reducing the introduced azide group by catalytic reduction or by using an aluminum hydride such as lithium aluminum hydride.

In Step H11, a compound of formula (XVIII) is prepared from a compound of formula (XXXVII) or a compound of formula (XVIII') is prepared from a compound of formula (XXXVII') by acylation, for example methanesulfonylation, toluenesulfonylation, trifluoromethanesulfonylation or trifluoroacetylation to prepare an ester; then allowing the resulting ester to react with an alkali metal cyanide (e.g. sodium cyanide) in dimethylformamide, dimethyl sulfoxide or hexamethylphosphoric triamide to introduce a nitrile group into position 3; then hydrolysis with ethanol-aqueous sodium hydroxide at 20° C. to 80° C. for 1 to 24 hours to prepare a carboxylic acid; and then allowing the resulting carboxylic acid to react with an acyl halide-forming agent such as a phosphorus pentahalide or a thionyl halide.

In Step H12, an isocyanate compound of formula (XXI) is prepared from an acyl halide compound of formula (XVIII) or an isocyanate compound of formula (XXI') is prepared from an acyl halide compound of formula (XVIII') by reaction with an alkali metal azide to prepare an acyl azide followed by heating the resulting acyl azide to result in a Curtius rearrangement. The isocyanate compound can also be prepared from the carboxylic acid obtained in the middle stage of Step H11 in a similar manner to Step D1.

After completion of each of the reactions, the desired compound can be separated from the reaction mixture by conventional means. For example, after condensation of the reaction mixture, the residue may be purified by silica gel column chromatography to afford the purified compound.

The compounds of the present invention have shown excellent PAF antagonistic activity and anti-inflammatory activity, in terms of the duration of the effect and/or biological utilization. They are, accordingly, useful as a new type of anti-shock agent, anti-thrombotic agent, anti-asthmatic agent, anti-allergic agent and anti-inflammatory agent.

The compounds of the invention may be administered orally or parenterally as required and may, if desired, be formulated into appropriate pharmaceutical formulations, depending upon the desired route of administration. For example, for oral administration, the compounds may be formulated as tablets, capsules, granules, powders or syrups. For parenteral administration, they may be formulated as injectible solutions or suspensions or as suppositories. Although the preferred dose will vary, depending upon the nature of the disorder, the symptoms, age, condition and body weight of the patient and the route of administration, a preferred dose for an adult human patient would normally be expected to be from 0.1 to 200 mg/kg body weight per day, and this could be administered in a single dose or in divided doses.

The invention is further illustrated by the following non-limiting Examples. Preparation of certain of the starting materials employed in these Examples is illustrated by the subsequent Preparations. The biological activities of certain of the compounds of the invention are then illustrated in the subsequent Experiments. In the Examples and Preparations, all Infrared Spectra were measured in $CHCl_3$, if not otherwise mentioned, and all values of optical rotation were measured using the sodium D-line, i.e. all are $[\alpha]_D$.

EXAMPLE 1

(2RS)-3-Octadecyloxy-2-(2-thiazolyloxy)propyl 2-(tri-methylammonio)ethyl phosphate (inner salt)

1(a) A solution of 0.760 g of 2-bromoethyl phosphorodichloridate in 5 ml of methylene chloride was added to a solution of 0.896 g of (2RS)-1-O-octadecyl-2-O-(2-thiazolyl)glycerol (prepared as described in Preparation 1) and 0.5 ml of triethylamine in 15 ml of methylene chloride, whilst ice-cooling. The mixture was stirred at room temperature for 6 hours, after which 2 ml of pyridine and 1 ml of water were added to the mixture, and stirring was continued for a further 50 minutes. At the end of this time, the solvent was removed by evaporation under reduced pressure, and the residue was diluted with cold water and adjusted to a pH value of 1 by the addition of 10% w/v aqueous hydrochloric acid. The mixture was then extracted twice with diethyl ether, and the combined extracts were washed with water, dried and concentrated by evaporation under reduced pressure. The residue (1.36 g) was subjected to column chromatography through 35 g of silica gel. 1.69 g of crude (2RS)-3-octadecyloxy-2-(2-thiazolyloxy)propyl 2-bromoethyl phosphate was obtained from the fractions eluted with mixtures of methanol and methylene chloride ranging from 3:100 to 1:10.

Nuclear Magnetic Resonance Spectrum ($CDCl_3$) δ ppm:

0.8–1.7 (35H, multiplet);
3.2–4.4 (10H, multiplet);
5.25 (1H, multiplet);
6.65 (1H, doublet, J=4.5 Hz);
7.17 (1H, doublet, J=4.5 Hz).

1(b) 1.056 g of the crude (2RS)-3-octadecyloxy-2-(2-thiazolyloxy)propyl 2-bromoethyl phosphate [prepared as described in step (a) above] was dissolved in 26 ml of a 3:5:5 by volume mixture of chloroform, isopropanol and dimethylformamide, and about 10 g of gaseous trimethylamine was introduced into the solution. The reaction mixture was then warmed, whilst stirring, for 5.5 hours on an oil bath kept at 50° C. in a reaction flask fitted with a reflux condenser cooled with dry ice and acetone. At the end of this time, the reaction mixture was cooled, and 0.355 g of silver carbonate was added. The mixture was then heated under reflux on an oil bath for 1 hour. The mixture was then cooled and concentrated by evaporation under reduced pressure. Methanol was added to the residue, and an insoluble material was filtered off. The solvent was stripped off from the filtrate, and the residue (1.07 g) was subjected to column chromatography through 25 g of silica gel. 0.690 g of the title compound was obtained as a white powder melting at 140° to 160° C. (with decomposition) from the fractions eluted with mixtures of methylene chloride and methanol ranging from 3:10 to 2:1 by volume and with methanol.

Nuclear Magnetic Resonance Spectrum ($CDCl_3$) δ ppm:

0.7–1.7 (35H, multiplet):
3.33 (9H, singlet);
3.43 (2H, triplet. J=7 Hz);
3.65–4.45 (8H, multiplet);
5.27 (1H, multiplet);
6.69 (1 H, doublet. J=4 Hz);
7.11 (1 H, doublet, J=4 Hz).
Elemental analysis:
Calculated for $C_{29}H_{57}N_2O_6PS$: C, 58.76%; H, 9.70%; N, 4.73%; P, 5.22%; S, 5.41%. Found: C, 58.37%; H, 9.57%; N, 4.86%; P, 5.23%; S. 5.29%.

EXAMPLE 2

(2RS)-3-Octadecyloxy-2-(3-isoxazolyloxy)propyl 2-(trimethylammonio)ethyl phosphate (inner salt)

Using a similar phosphorylation reaction to that described in Example 1(a), 1.359 g of crude (2RS)-3-ootadecyloxy-2-(3-isoxazolyloxy)propyl 2-bromoethyl phosphate was obtained from 1.000 g of (2RS)-1-O-octadecyl-2-O-(3-isoxazolyl)glycerol (prepared as described in Preparation 2). In a similar manner to that described in Example 1(b), 0.650 g of this crude product was reacted with trimethylamine to give 0.386 g of the title compound as a white powder, melting at 115°–125° C.

Nuclear Magnetic Resonance Spectrum (CD$_3$OD) δ ppm:
0.7–1.7 (35H, multiplet);
3.20 (9H, singlet);
3.3–3.9 (6H, multiplet);
4.05–4.50 (4H, multiplet);
4.92 (1H, quintet, J=5 Hz);
6.15 (1H, doublet, J=2 Hz);
8.38 (1H, doublet, J=2 Hz).
Elemental analysis:
Calculated for $C_{29}H_{57}N_2O_7P \cdot \frac{1}{2}H_2O$: C, 59.46%; H, 9.98%; N, 4.78%; P, 5.29%. Found: C, 59.44%; H, 9.57%; N, 4.71%; P, 5.04%.

EXAMPLE 3

(2RS)-3-Octadecyloxy-2-(3-isoxazolyloxy)propyl 2-pyridinioethyl phosphate (inner salt)

A solution of 0.663 g of crude (2RS)-3-octadecyloxy-2-(3-isoxazolyloxy)propyl 2-bromoethyl phosphate (prepared as described in the first part of Example 2) in 4.5 ml of pyridine was heated on an oil bath kept at 60° C. for 11 hours. After allowing the mixture to cool, excess pyridine was distilled off. The residue was dissolved in 10 ml of chloroform, and the solution was heated under reflux for 1 hour. The mixture was then cooled, and the solvent was evaporated off under reduced pressure. Methanol was then added to the residue, and the resulting insoluble material was filtered off. The filtrate was concentrated by evaporation under reduced pressure, and the residue was subjected to column chromatography through 15 g of silica gel. 0.305 g of the title compound was obtained as a hygroscopic powder, melting at 49°–52° C., from the fractions eluted with a 2:1 by volume mixture of methylene chloride and methanol.

Nuclear Magnetic Resonance Spectrum (CD$_3$OD) δ ppm:
0.7–1.8 (35H, multiplet);
3.3–4.6 (10H, multiplet);
4.78 (1H, multiplet);
6.13 (1H, doublet, J=2 Hz);
8.35 (1H, doublet, J=2 Hz);
8.10 (2H, multiplet);
8.60 (1H, triplet, J=7.5 Hz);
9.00 (2H, doublet, J=6 Hz).
Elemental analysis:
Calculated for $C_{31}H_{53}N_2O_7P \cdot 3/2H_2O$: C, 59.69%; H, 9.05%; N, 4.49%; P, 4.97%. Found: C, 59.91%; H, 9.11%; N. 4.34%; P, 4.87%.

EXAMPLE 4

(2RS)-3-Hexadecyloxy-2-(3-isoxazolyloxy)propyl 2-(trimethylammonio)ethyl phosphate (inner salt)

1.373 g of (2RS)-1-O-hexadecyl-2-O-(3-isoxazolyl)-glycerol (prepared as described in Preparation 3) was phosphorylated and trimethylaminated and then treated with silver carbonate in a similar manner to that described in Example 1, to give a crude product. 2.35 g of which were purified by column chromatography through 90 g of silica gel. 1.313 g of the title compound was obtained from the fractions eluted with a 60:35:5 by volume mixture of methylene chloride, methanol and water, in the form of a white powder melting at 128°–135° C.

Nuclear Magnetic Resonance Spectrum (CD$_3$OD) δ ppm:
0.8–1.8 (31H, multiplet);
3.21 (9H, singlet);
3.47 (2H, triplet. J=6 Hz);
3.5–4.0 (4H, multiplet);
4.0–4.45 (4H, multiplet);
4.93 (1H, multiplet);
6.17 (1H, doublet, J=2 Hz);
8.39 (1H, doublet, J=2 Hz).
Elemental analysis:
Calculated for $C_{27}H_{53}N_2O_7P \cdot 1.5H_2O$: C, 56.32%; H. 9.80%; N, 4.87%; P, 5.38%.
Found: C, 56.22%; H. 9.69%; N, 4.70%; P, 5.88%.

EXAMPLE 5

(2R)-3-Hexadecyloxy-2-(3-isoxazolyloxy)propyl 2-(trimethylammonio)ethyl phosphate (inner salt)

1.661 g of the title compound was obtained as a white powder melting at 130°–135° C. from 2.111 g of 1-O-hexadecyl-2-O-(3-isoxazolyl)-sn-glycerol (prepared as described in Preparation 4) by following a procedure similar to that described in Example 4.
$[\alpha]^{26}$ −3.50° (c=1.00, CH$_3$OH).
Elemental analysis:
Calculated for $C_{27}H_{53}N_2O_7P \cdot H_2O$: C, 57.22%; H, 9.78%; N, 4.94%; P, 5.47%. Found: C. 57.22%; H, 9.67%; N, 4.98%; P, 5.94%.

EXAMPLE 6

(2S)-3-Hexadecyloxy-2-(3-isoxazolyloxy)propyl 2-(trimethylammonio)ethyl phosphate (inner salt)

1.261 g of the title compound was obtained as a white powder melting at 130°–135° C. from 1.574 g of 3-O-hexadecyl-2-O-(3-isoxazolyl)-sn-glycerol (prepared as described in Preparation 5) by following a procedure similar to that described in Example 4.
$[\alpha]^{26}$ +3.50° (c=1.00, CH$_3$OH).

EXAMPLE 7

(2RS)-3-Hexadecyloxy-2-(5-phenyl-3-isoxazolyloxy)-propyl 2-(trimethylammonio)ethyl phosphate (inner salt)

Using a similar phosphorylation reaction to that described in Example 1(a), 2.73 g of crude (2RS)-3-hexadecyloxy-2-(5-phenyl-3-isoxazolyloxy)propyl 2-bromoethyl phosphate were obtained from 2.00 g of (2RS)-1-O-hexadecyl-2-O-(5-phenyl-3-isoxazolyl)-glycerol (prepared as described in Preparation 6). In a similar manner to that described in Example 1(b), 0.854 g of this crude product was reacted with trimethylamine to give 0.661 g of the title compound as a hygroscopic white powder.

Nuclear Magnetic Resonance Spectrum ($CD_3OD$) δ ppm:
0 7–1.8 (31H, multiplet);
3.20 (9H, singlet);
3.50 (2H, triplet, J=6 Hz);
3.5–3.75 (2H, multiplet);
3.78 (2H, doublet, J=4.5 Hz);
4.2–4.5 (4H, multiplet);
4.99 (1H, multiplet);
6.53 (1H, singlet);
7.4–7.9 (5H, multiplet).

Elemental analysis:
Calculated for $C_{33}H_{57}N_2O_7P.\frac{1}{2}H_2O$: C, 62.54%; H, 9.22%; N, 4.42%; P, 4.89%. Found: C, 62.14%; H, 9.20%; N, 4.28%; P, 4.51%.

EXAMPLE 8

(2RS)-3-Hexadecyloxy-2-(5-phenyl-3-isoxazolyloxy)-propyl 2-pyridinioethyl phosphate (inner salt)

0.875 g of the crude (2RS)-3-hexadecyloxy-2-(5-phenyl-3-isoxazolyloxy)propyl 2-bromoethyl phosphate obtained as described in the first part of Example 7 was reacted with pyridine in a similar manner to that described in Example 3 to afford 0.507 g of the title compound as a colorless oil.

Nuclear Magnetic Resonance Spectrum ($CD_3OD$) δ ppm:
0 7–1.8 (31H, multiplet); 3.50 (2H, triplet, J=6 Hz); 3.74 (2H, doublet, J=5 Hz); 3.9–4.5 (4H, multiplet); 4.75–5.0 (3H, multiplet); 6.51 (1H, singlet); 7.4–7.9 (5H, multiplet); 8.0–9.15 (5H, multiplet).

Elemental analysis:
Calculated for $C_{35}H_{53}N_2O_7P.H_2O$: C, 63.43%; H, 8.36%; N, 4.23%; P, 4.67%. Found: C, 63.11%; H, 8.08%; N, 4.22%; P, 4.77%.

EXAMPLE 9

(2RS)-3-Hexadecyloxy-2-(5-phenyl-3-isoxazolyloxy)-propyl 2-thiazolioethyl phosphate (inner salt)

A mixture of 0.925 g of the crude (2RS)-3-hexadecyloxy-2-(5-phenyl-3-isoxazolyloxy)propyl 2-bromoethyl phosphate obtained as described in the first part of Example 7 and 0.51 ml of thiazole in 0.8 ml of toluene was heated on an oil bath kept at 70° C. for 5 days, whilst stirring. The mixture was then cooled and freed from toluene by evaporation under reduced pressure. 15 ml of chloroform were then added to the residue, followed by 0.296 g of silver carbonate. The mixture was then heated under reflux for 1 hour. At the end of this time, the mixture was cooled, an insoluble material was filtered off and the solvent was stripped off from the filtrate by evaporation under reduced pressure. The residue was subjected to column chromatography through 20 g of silica gel. 0.117 g of the title compound was obtained as a viscous oil from the fractions eluted with a 1:1 by volume mixture of methanol and methylene chloride and with a 35:60:5 by volume mixture of methanol, methylene chloride and water.

Nuclear Magnetic Resonance Spectrum ($CD_3OD$) δ ppm:
0.7–1.8 (31H, multiplet);
3.50 (2H, triplet, J=6 Hz);
3.77 (2H, doublet, J=4,5 Hz);
3.9–4.4 (4H, multiplet);
4.6–5.2 (3H, multiplet);
6.50 (1H, singlet);
7.4–7.9 (5H, multiplet);
8.25 (1H, doublet, J=4 Hz);
8.51 (1H, doublet, J=4 Hz);
10.20 (1H, multiplet).

Elemental analysis:
Calculated for $C_{33}H_{51}N_2O_7PS.H_2O$: C, 59.26%; H, 7.99%; N, 4.19%; P, 4.63%; S, 4.79%. Found: C, 59.19%; H, 7.83%; N, 4.11%; P, 4.36%; S, 4.48%.

EXAMPLE 10

(2RS)-3-Hexadecyloxy-2-(3-isoxazolyloxy)propyl 4-(trimethylammonio)butyrate bromide 10(a) A solution of 0.725 g of 4-bromobutyryl chloride in 5 ml of methylene chloride was added dropwise to a solution of 1.000 g of (2RS)-1-O-hexadecyl-2-O-(3-isoxazolyl)glycerol [prepared as described in Preparation 3(a)] and 0.55 ml of triethylamine in 15 ml of methylene chloride, whilst ice cooling. The mixture was stirred for 1.5 hours at room temperature, after which it was poured into water and the methylene chloride was distilled off under reduced pressure. The aqueous residue was extracted twice with ethyl acetate. The combined extracts were washed with water, dried and concentrated by evaporation under reduced pressure. The residue was subjected to column chromatography through 30 g of silica gel. 1.016 g of (2RS)-3-hexadecyloxy-2-(3-isoxazolyloxy)propyl 4-bromoethylbutyrate was obtained as an oil from the fractions eluted with a 1:9 by volume mixture of diethyl ether and hexane.

Nuclear Magnetic Resonance Spectrum ($CD_3OD$) δ ppm:
0.7–1.8 (31H, multiplet); 1.95–2.70 (4H, multiplet); 3.3–3.6 (4H, multiplet); 3.72 (2H, doublet, J=5 Hz); 4.43 (AB doublet of quartets; $δ_A$4.33, doublet of doublets, $J_1$12, $J_2$=6 Hz; $δ_B$4.53; doublet of doublets, $J_1$=12, $J_2$=4.5 Hz);
5.08 (1H, multiplet);
5.97 (1H, doublet, J=2 Hz); 8.11 (1H, doublet, J=2 Hz).

Infrared Absorption Spectrum $ν_{max}cm^{-1}$:
1740 (—CO—).

Elemental analysis:
Calculated for $C_{26}H_{46}BrNO_5$: C, 58.64%; H, 8.71%; Br, 15.00%; N, 2.63%. Found: C, 58.75%; H, 8.64%; Br, 14.73%; N, 2.69%.

10(b) 0.471 g of (2RS)-3-hexadecyloxy-2-(3-isoxazolyloxy)propyl 4-bromoethylbutyrate [prepared as described in step (a) above] was dissolved in 8 ml of a 3:5:5 by volume mixture of chloroform, isopropanol and dimethylformamide. 2.44 g of trimethylamine were then introduced into the solution, whilst ice cooling. The reaction mixture was then heated on a oil bath kept at 50° C. for 4 hours, after which it was cooled and evaporated to dryness under reduced pressure. The residue was subjected to column chromatography through 10 g of silica gel Those fractions eluted with mixtures of methanol and methylene chloride ranging from 1:10 to 1.5 by volume were collected and purified by chromatography through a Lobar Column B, to obtain 0.363 g of the title compound as a white powder melting at 74°–76° C.

Nuclear Magnetic Resonance Spectrum (CD$_3$OD) δ ppm:
0 7–1.8 (31H, multiplet);
1.85–2.30 (2H, multiplet);
2.48 (2H, triplet, J=6 Hz);
3.17 (9H, singlet);
3.48 (2H, triplet);
3.71 (2H, doublet, J=5 Hz);
4.43 (2H, AB doublet of quartets; δ$_A$4.31, J$_1$=12, J$_2$=7 Hz; δ$_B$4.55, J$_1$=12. J$_2$=4.5 Hz);
5.01 (1H, multiplet);
6.15 (1H, doublet, J=2 Hz);
8.41 (1H, doublet, J=2 Hz).

Infrared Absorption Spectrum ν$_{max}$cm$^{-1}$: 1740 (—O—CO—).

Elemental analysis:
Calculated for C$_{29}$H$_{55}$BrN$_2$O$_5$.½H$_2$O: C, 57.99%; H, 9.40%; N. 4.66%; Br, 13.30%. Found: C, 57.96%; H, 9.36%; N, 4.49%; Br, 13.77%.

EXAMPLE 11

(2RS)-3-(N-Heptadecylcarbamoyloxy)-2-(3-isoxazolyloxy)propyl 2-(trimethylammonio)ethyl phosphate (inner salt)

11(a) 2.000 g of (2RS)-1-O-(N-heptadecylcarbamoyl)-2-O-(3-isoxazolyl)glycerol (prepared as described in Preparation 13) were reacted with 1.647 g of 2-bromoethyl phosphorodichloridate in a similar manner to that described in Example 1(a), to give 2.501 g of (2RS)-3-(N-heptadecylcarbamoyloxy)-2-(3-isoxazolyloxy)propyl 2-bromoethyl phosphate as a glassy solid.

Nuclear Magnetic Resonance Spectrum (CDCl$_3$) δ ppm:
0.7–1.8 (33H, multiplet);
2.8–3.7 (5H, multiplet);
8–4.8 (6H, multiplet);
5.03 (1H, multiplet);
5.80 (1H, multiplet);
6.07 (1H, doublet, J=2 Hz);
8.13 (1H, doublet, J=2 Hz).

Infrared Absorption Spectrum ν$_{max}$cm$^{-1}$: 3480 (—NH—) and 1720 (—O—CO—N).

11(b) 0.800 g of (2RS)-3-(N-heptadecylcarbamoyloxy)-2-(3-isoxazolyloxy)propyl 2-bromoethyl phosphate [prepared as described in step (a) above] was reacted with trimethylamine in a similar manner to that described in Example 1(b), to give 0.640 g of the title compound as viscous oil.

Nuclear Magnetic Resonance Spectrum (CD$_3$OD) δ ppm:
0.7–1.7 (33H, multiplet);
3.05 (2H, triplet, J=7 Hz);
3.22 (9H, singlet);
3.61 (2H, triplet, J=4.5 Hz);
4.00–4.60 (6H, multiplet);
5.01 (1H, multiplet);
6.17 (1H, doublet, J=2 Hz);
8.40 (1H, doublet, J=2 Hz).

Infrared Absorption Spectrum ν$_{max}$cm$^{-1}$: 3460 (—NH—) and 1720 (—CO—N).

Elemental analysis:
Calculated for C$_{29}$H$_{56}$N$_3$O$_8$P.H$_2$O: C, 55.84%; H, 9.37%; N, 6.74%; P, 4.97%. Found: C, 55.59%; H, 9.10%; N, 6.66%; P, 5.11%.

EXAMPLE 12

(2RS)-3-(N-Heptadecylcarbamoyloxy)-2-(3-isoxazolyloxy)propyl 2-pyridinioethyl phosphate (inner salt)

0.800 g of (2RS)-3-(N-heptadecylcarbamoyloxy)-2-(3-isoxazolyloxy)propyl 2-bromoethyl phosphate [prepared as described in Example 11(a)] was reacted with pyridine in a similar manner to that described in Example 3, to afford 0.549 g of the title compound as a viscous resinous material.

Nuclear Magnetic Resonance Spectrum (CD$_3$OD) δ ppm:
1 0.7–1.7 (33H, multiplet);
3.05 (2H, triplet, J=7 Hz);
4.03 (2H, triplet, J=6 Hz):
4.2–4.6 (4H, multiplet):
4.70–5.15 (3H, multiplet):
6.13 (1H, doublet, J=2 Hz):
8.13 (2H, triplet, J=7.5 Hz);
8.38 (1H, doublet. J=2 Hz);
8.63 (1H, triplet, J=7.5 Hz);
9.03 (2H, multiplet).

Elemental analysis:
Calculated for C$_{31}$H$_{52}$N$_3$O$_8$P.H$_2$O: C, 57.84%; H, 8.45%; N, 6.53%; P, 4.81%. Found: C, 57.70%; H, 8.46%; N, 6.34%; P, 5.08%.

EXAMPLE 13

(2RS)-3-(N-Heptadecylcarbamoyloxy)-2-(3-isoxazolyloxy)propyl 2-thiazolioethyl phosphate (inner salt)

A solution of 0.940 g of (2RS)-3-(N-heptadecylcarbamoyloxy)-2-(3-isoxazolyloxy)propyl 2-bromoethyl phosphate [prepared as described in Example 11(a)] and 1.06 ml of thiazole in toluene was heated on an oil bath kept at 70° C. for 4 days, whilst stirring. The solvent was then distilled off, and the resulting residue was dissolved in 10 ml of a 95:5 by volume mixture of tetrahydrofuran and water. The solution thus obtained was passed over 11 ml of Amberlite (trade mark) MB 3 resin. The eluate was repeatedly passed six times through the same column, and the column was finally washed with a 95:5 by volume mixture of tetrahydrofuran and water. The eluates and the washings were combined and concentrated by evaporation under reduced pressure. The residue was purified by medium pressure liquid chromatography using a Lobar B column. 0.312 g of the title compound was obtained as a resinous material from the fractions eluted with a 60:35:5 by volume mixture of methylene chloride, methanol and water.

Nuclear Magnetic Resonance Spectrum (CD$_3$OD) δ ppm:
0.7–1.7 (33H, multiplet);
3.05 (2H, multiplet);
3.8–4.6 (6H, multiplet);
4.8–5.2 (3H, multiplet);
6.15 (1H, doublet, J=2 Hz);
6.93 (1H, multiplet);
8.28 (1H, doublet. J=4.5 Hz);
8.38 (1H, doublet, J=2 Hz);
8.51 (1H, doublet, J=4.5 Hz).

Elemental analysis:
Calculated for $C_{29}H_{50}N_3O_8PS \cdot \frac{1}{2}H_2O$: C, 54.36%; H, 8.02%; N. 6.54%; P, 4.83%; S, 5.00%. Found: C, 54.30%; H, 7.85%; N. 6.54%; P, 4.86%; S, 5.25%.

EXAMPLE 14

(2R)-3-(N-Heptadecylcarbamoyloxy)-2-(3-isoxazolyloxy)propyl 2-thiazolioethyl phosphate (inner salt)

1.500 g of 1-O-(N-heptadecylcarbamoyl)-2-O-(3-isoxazolyl)-sn-glycerol (prepared as described in Preparation 18) was reacted with 1.235 g of 2-bromoethyl phosphorodichloridate, following a procedure similar to that described in Example 1(a). 3.0 ml of pyridine and 1.5 ml of water were then added to the reaction mixture. The mixture was then stirred for 15 hours at room temperature, after which it was worked up in a similar manner to that described in Example 1(b), to afford a residue (2.15 g). Without purification, this residue was immediately treated in a similar manner to that described in Example 13, to give 1.107 g of the title compound as a white powder melting at 50°-52° C.

$[\alpha]^{26} + 3.27°$ (c=1.01, $CH_3OH$).

EXAMPLE 15

(2RS)-3-(N-Heptadecylcarbamoyloxy)-2-(3-isoxazolyloxy)propyl 5-thiazoliopentyl phosphate (inner salt)

A solution of 0.644 g of 5-bromopentyl phosphorodichloridate in 2 ml of methylene chloride was added, whilst ice cooling, to a solution of 0.500 g of (2RS)-1-O-(N-heptadecylcarbamoyl)-2-O-(3-isoxazolyl)glycerol (prepared as described in preparation 13) and 0.47 ml of triethylamine dissolved in 8 ml of methylene chloride. The mixture was stirred for 3 hours at room temperature, and then 1.0 ml of pyridine and 0.5 ml of water were added and it was stirred for 18 hours. The solvent was stripped from the reaction mixture by evaporation under reduced pressure, and the residue was mixed with water and ethyl acetate. The aqueous layer was adjusted to a pH value of 1 by adding 10% w/v aqueous hydrochloric acid. The aqueous layer was separated from the organic layer, and was then extracted three times with ethyl acetate. The combined extracts and organic layer were washed with water, dried and concentrated by evaporation under reduced pressure. The residue (0.83 g) and 0.81 ml of thiazole were dissolved in 1 ml of toluene, and the mixture was heated on an oil bath kept at 80° C. for 67 hours. The mixture was cooled, the solvent was removed by evaporation under reduced pressure, and the residue was subjected to column chromatography through 15 g of silica gel. An oily substance (0.72 g) was obtained from the fractions eluted with mixtures of methylene chloride and methanol ranging from 17:3 to 4:1 by volume and with a 60:35:5 by volume mixture of methylene chloride, methanol and water.

The whole of this oil was dissolved in 5 ml of a 60:35:5 by volume mixture of methylene chloride, methanol and water, and the solution was passed through a column packed with 5 ml of Amberlite (trade mark) MB-3 resin. The mixture on the column was eluted with a 60:35:5 by volume mixture of methylene chloride, methanol and water. The eluent was passed through this column five times. Lastly, the resin was washed with a 60:35:5 by volume mixture of methylene chloride, methanol and water. The eluates and the washings were combined and concentrated by evaporation under reduced pressure. The residue was purified by medium pressure liquid chromatography using a Lobar B column. 0.440 g of the title compound was obtained from the fractions eluted with a 160:35:5 by volume mixture of methylene chloride, methanol and water, in the form of a powder melting at about 120° C.

Nuclear Magnetic Resonance Spectrum ($CD_3OD$) δ ppm: 0.75–1.85 (37H, multiplet);
2.06 (2H, multiplet);
3.05 (2H, triplet, J=7 Hz);
3.7–4.5 (6H, multiplet); 4.62 (2H, triplet. J=7.5 Hz); 4.98 (1H, multiplet); 6.12 (1H, doublet. J=2 Hz) 8.28 (1H, doublet, J=4 Hz); 8.35 (1H, doublet. J=2 Hz); 8.53 (1H, doublet, J=4 Hz).

Infrared Absorption Spectrum ($CHCl_3$) $\nu_{max} cm^{-1}$: 3560, 1720.

Elemental analysis:
Calculated for $C_{32}H_{56}N_3O_7PS \cdot H_2O$: C, 55.55%; H, 8.45%; N, 6.07%; p, 4.48%; S, 4.63%. Found: C. 55.59%; H, 8.42%; N, 5.87%; p, 4.21%; S, 4.96%.

EXAMPLE 16

(2RS)-3-(N-Heptadecylcarbamoyloxy)-2-(3-isoxazolyloxy)propyl 6-thiazoliohexyl phosphate (inner salt)

0.438 g of the title compound was obtained from 0.500 g of (2RS)-1-O-(N-heptadecylcarbamoyl)-2-O-(3-isoxazolyl)glycerol (prepared as described in Preparation 13) and 0.676 g of 6-bromohexyl phosphorodichloridate by following a similar procedure to that described in Example 15. It was a powder melting at about 140° C.

Nuclear Magnetic Resonance Spectrum ($CD_3OD$) δ ppm:
0.75–1.80 (39H, multiplet);
2.00 (2H, multiplet);
3.05 (2H, triplet, J=7 Hz);
3.70–4.50 (6H, multiplet);
4.62 (2H, triplet. J=7.5 Hz);
4.98 (1H, multiplet);
6.12 (1H, doublet, J=2 Hz);
8.30 (1H, doublet, J=4 Hz);
8.35 (1H, doublet, J=2 Hz);
8.53 (1H, doublet, J=4 Hz).

Elemental analysis:
Calculated for $C_{33}H_{58}N_3O_8PS \cdot H_2O$: C, 56.15%; H, 8.57%; N, 5.95%; p, 4.38%; S, 4.54%. Found: C, 56.56%; H, 8.62%; N. 5.53%; p, 4.24%; S,4.83%.

EXAMPLE 17

(2RS)-3-(N-Heptadecylcarbamoyloxy)-2-(3-isoxazolyloxy)propyl 2-(3-methyl-1-imidazolio)ethyl phosphate (inner salt)

A mixture of 0.900 g of (2RS)-3-(N-heptadecylcarbamoyloxy)-2-(3-isoxazolyloxy)propyl 2-bromoethyl phosphate [prepared as described in Example 11(a)], 1.14 ml of N-methylimidazole and 1.0 ml of toluene was heated on an oil bath kept at 80° C. for 15 hours, whilst stirring. The toluene was then distilled off, and the resulting residue was dissolved in 10 ml of a 95:5 by volume mixture of tetrahydrofuran and water. The resulting solution was passed through a column of 14 ml of Amberlite MB-3 resin. The eluate wa repeatedly passed two times through the same column and the column was finally washed with a 95:5 by volume mixture of tetrahydrofuran and water. The eluates and the washings were combined and concentrated by evaporation under reduced pressure. The residue was purified by medium pressure liquid chromatography using a Lobar B column. 0.656 g of the title compound was obtained as a white powder melting at 45°–46° C. from the fractions eluted with a 160:35:5 by volume mixture of methylene chloride, methanol and water.

Nuclear Magnetic Resonance Spectrum (CD$_3$OD) δ ppm: 0.7–1.8 (33H, multiplet); 3.07 (2H, triplet, J=7 Hz); 3.95 (3H, singlet); 4.00–4.55 (8H, multiplet); 4.95 (1H, multiplet); 6.13 (1H, doublet, J=2 Hz); 7.53 (1H, doublet, J=2 Hz); 7.63 (1H, doublet, J=2 Hz); 8.38 (1H, doublet, J=2 Hz).

Elemental analysis: Calculated for C$_{30}$H$_{55}$N$_4$O$_8$P.·H$_2$O: C, 55.71%; H, 8.57%; N, 8.66%. Found: C, 55.82%; H, 8.43%; N, 8.73%.

EXAMPLE 18

(2RS)-3-(N-Heptadecylcarbamoyloxy)-2-(5-methyl-3-isoxazolyloxy)propyl 2-thiazolioethyl phosphate (inner salt)

To a solution of 1.900 g of (2RS)-1-O-(N-heptadecylcarbamoyl)-2-O-(5-methyl-3-isoxazolyl)glycerol (prepared as described in Preparation 21) and 0.99 ml of triethylamine in 10 ml of methylene chloride was added dropwise a solution of 1.516 g of 2-bromoethyl phosphorodichloridate in 10 ml of methylene chloride, and the mixture was stirred at room temperature for 7 hours. At the end of this time, 4 ml of pyridine and 2 ml of water were added, and the mixture was stirred at room temperature for 17 hours. The methylene chloride of the solvent was then distilled off. The residue was diluted with water and adjusted to a PH value of 1 by the addition of a 10% w/v aqueous solution of hydrochloric acid; the solution was then extracted twice with ethyl acetate. The combined extracts were washed with water, dried and concentrated by evaporation under reduced pressure. The residue and 2.96 ml of thiazole were dissolved in 3 ml of toluene, and the solution was heated on an oil bath kept at 80° C. for 4 days, whilst stirring. The reaction mixture was then evaporated to dryness under reduced pressure. The residue was subjected to column chromatography through 40 g of silica gel. An oily material (1.80 g) obtained from the fractions eluted with a 1:9 by volume mixture of methylene chloride and methanol and with methanol was dissolved in a 95:5 by volume mixture of tetrahydrofuran and water. The solution was passed through a column containing 14 ml of Amberlite MB-3 resin. The eluate was repeatedly passed five times through the same column, and the column was finally washed with a 95:5 by volume mixture of tetrahydrofuran and water. The eluate and the washings were combined and concentrated by evaporation under reduced pressure, to give a residue, which was purified by medium pressure liquid chromatography using a Lobar B column. 1.340 g of the title compound was obtained as a white resinous material from the fractions eluted with a 160:35:5 by volume mixture of methylene chloride, methanol and water.

Nuclear Magnetic Resonance Spectrum (CD$_3$OD) δ ppm: 0.8–1.70 (33H, multiplet); 2.32 (3H, singlet); 3.06 (2H, triplet, J=7 Hz); 3.90–4.60 (6H, multiplet); 4.65–5.10 (3H, multiplet); 5.83 (1H, singlet); 8.29 (1H, doublet, J=4 Hz); 8.52 (1H, doublet, J=4 Hz).

Elemental analysis: Calculated for C$_{30}$H$_{52}$N$_3$O$_8$PS.·H$_2$O: C, 54.28%; H, 8.20%; N, 6.51%; P, 4.80%; S, 4.83%. Found: C, 54.00%; H, 7.75%; N, 6.26%; P, 4.45%; S, 4.41%.

EXAMPLE 19

(2RS)-3-(N-Heptadecylcarbamoyloxy)-2-(5-phenyl-3-isoxazolyloxy)propyl 2-thiazolioethyl phosphate (inner salt)

0.976 g of the title compound was obtained as a resinous material from 1.500 g of (2RS)-1-O-(N-heptadecylcarbamoyl)-2-O-(5-phenyl-3-isoxazolyl)glycerol (prepared as described in Preparation 24) in a similar manner to that described in Example 18.

Nuclear Magnetic Resonance Spectrum (CD$_3$OD) δ ppm: 0.7–1.6 (33H, multiplet); 3.07 (2H, triplet, J=7 Hz); 3.9–4.6 (6H, multiplet); 4.6–5.3 (3H, multiplet); 6.50 (1H, singlet); 7.4–7.9 (5H, multiplet); 8.27 (1H, doublet, J=4 Hz); 8.51 (1H, doublet, J=4 Hz).

Elemental analysis: Calculated for C$_{35}$H$_{54}$N$_3$O$_8$PS.3/2H$_2$O: C, 57.20%; H, 7.82%; N, 5.72%; P, 4.21%; S, 4.36%. Found: C, 57.34%; H, 7.59%; N, 5.76%; P, 3.99%; S, 4.02%.

EXAMPLE 20

(2RS)-3-(5-Pentadecyl-3-isoxazolyloxy)-2-methoxypropyl 2-thiazolioethyl phosphate (inner salt)

0.465 g of the title compound was obtained as a white powder melting at 92°–97° C. from 0.750 g of (2RS)-1-O-(5-pentadecyl-3-isoxazolyl)-2-O-methylglycerol (prepared as described in Preparation 29) in a similar manner to that described in Example 18.

Nuclear Magnetic Resonance Spectrum (CD$_3$OD) δ ppm: 0.7–1.9 (29H, multiplet); 2.65 (2H, triplet, J=7 Hz); 3.47 (3H, singlet); 3.6–4.5 (7H, multiplet); 4.7–4.95 (2H, multiplet); 5.82 (1H, singlet); 8.29 (1H, doublet, J=4 Hz); 8.52 (1H, doublet, J=4 Hz).

Elemental analysis: Calculated for C$_{27}$H$_{47}$N$_2$O$_7$PS.·H$_2$O: C, 54.71%; H, 8.33%; N, 4.73%; P, 5.23%; S, 5.41%. Found: C, 55.07%; H, 8.20%; N, 4.71%; P, 4.92%; S, 5.64%.

EXAMPLE 21

(2RS)-3-(5-Hexadecyl-3-isoxazolyloxy)-2-(3-isoxazolyloxy)propyl 2-(3-methyl-1-imidazolio)ethyl phosphate (inner salt)

21(a) 1.828 g of (2RS)-1-O-(5-hexadecyl-3-isoxazolyl)-2-O-(3-isoxazolyl)glycerol (prepared as described in Preparation 33) was reacted with 1.451 g of 2-bromoethyl phosphorodichloridate in a similar manner to that described in Example 1(a), to afford 1.509 g of (2RS)-3-(5-hexadecyl-3-isoxazolyloxy)-2-(3-isoxazolyloxy)-propyl 2-bromoethyl phosphate.

Nuclear Magnetic Resonance Spectrum (CD$_3$OD-CDCl$_3$, 1:1) δ ppm: 0.7–2.0 (31H, multiplet); 2.65 (2H, broad triplet, J=7 Hz); 3.50 (2H, triplet, J=6 Hz); 3.9–4.7 (6H, multiplet); 5.15 (1H, multiplet); 5.70 (1H, singlet); 6.08 (1H, doublet, J=2 Hz); 8.26 (1H, doublet, J=2 Hz).

21(b) Following the procedure described in Example 17, 0.730 g of (2RS)-3-(5-hexadecyl-3-isoxazolyloxy)-2-(3-isoxazolyloxy)propyl 2-bromoethyl phosphate [prepared as described in step (a) above] was reacted with 0.91 ml of N-methylimidazole, to give 0.477 g of the title compound as a pale-yellow resinous material.

Nuclear Magnetic Resonance Spectrum (CD$_3$OD) δ ppm: 0.7–1.9 (31H, multiplet); 2.65 (2H, triplet, J=7 Hz); 3.95 (3H, singlet); 4.0–4.6 (8H, multiplet); 5.10 (1H, quintet, J=4.5 Hz); 5.82 (1H, singlet); 6.17 (1H, doublet, J=2 Hz); 7.55 (1H, broad singlet); 7.65 (1H, broad singlet); 8.40 (1H, doublet, J=2 Hz); 8.97 (1H, broad singlet).

Elemental analysis: Calculated for $C_{31}H_{51}N_4O_8P \cdot {}^5/_2 H_2O$: C, 54.45%; H, 8.25%; N, 8.19%. Found: C, 54.23%; H, 7.99%; N, 8.12%.

EXAMPLE 22

(2RS)-3-(5-Hexadecyl-3-isoxazolyloxy)-2-(3-isoxazolyloxy)propyl 2-thiazolioethyl phosphate (inner salt)

0.779 g of (2RS)-3-(5-hexadecyl-3-isoxazolyloxy)-2-(3-isoxazolyloxy)propyl 2-bromoethyl phosphate [prepared as described in Example 21(a)] was reacted with 0.86 ml of thiazole in a similar manner to that described in Example 13, to give 0.288 g of the title compound as a white powder melting at 94°–100° C.

Nuclear Magnetic Resonance Spectrum (CD$_3$OD) δ ppm: 0.8–1.9 (31H, multiplet); 2.63 (1H, triplet, J=7 Hz); 4.05–4.60 (6H, multiplet); 4.7–4.90 (2H, multiplet); 5.10 (1H, quintet, J=4.5 Hz); 5.80 (1H, singlet); 6.15 (1H, doublet, J=2 Hz); 8.27 (1H, multiplet); 8.39 (1H, doublet, J=2 Hz); 8.51 (1H, doublet, J=4 Hz); 10.20 (1H, multiplet).

Elemental analysis: Calculated for $C_{30}H_{49}N_3O_8PS \cdot H_2O$: C, 54.52%; H, 7.77%; N, 6.35%; P, 4.69%. Found: C, 54.25%; H, 7.38%; N, 6.31%; P, 4.83%.

EXAMPLE 23

(2RS)-3-(5-Pentadecyl-3-isoxazolyloxy)-2-(5-methyl-3-isoxazolyloxy)propyl 6-thiazoliohexyl phosphate (inner salt)

0.387 g of the title compound was obtained as a powder from 0.500 g of (2RS)-1-O-(5-pentadecyl-3-isoxazolyl)-2-O-(5-methyl-3-isoxazolyl)glycerol (prepared as described in Preparation 35) and 0.661 g of 6-bromohexyl phosphorodichloridate in a similar manner to that described in Example 15.

Nuclear Magnetic Resonance Spectrum (CD$_3$OD) δ ppm: 0.75–1.80 (35H, multiplet); 2.02 (2H, multiplet); 2.30 (3H, singlet); 2.63 (2H, triplet, J=7 Hz); 3.85 (2H, multiplet); 4.16 (2H, triplet, J=6 Hz); 4.4–4.8 (4H, multiplet); 5.06 (1H, multiplet); 5.80 (2H, singlet); 8.29 (1H, doublet, J=4 Hz); 8.52 (1H, doublet, J=4 Hz).

Elemental analysis: Calculated for $C_{34}H_{56}N_3O_8PS \cdot H_2O$: C, 57.04%; H, 8.17%; N, 5.87%; P, 4.33%; S, 4.48%. Found: C, 57.19%; H, 8.30%; N, 5.58%; P, 4.30%; S, 4.73%.

EXAMPLE 24

(2RS)-1-O-(5-Pentadecyl-3-isoxazolyl)-2-O-(5-methyl-3-isoxazolyl)-3-(7-thiazolioheptyl)glycerol methanesulfonate 0.15 ml of methanesulfonyl chloride was added to a solution of 0.708 g of (2RS)-1-O-(5-pentadecyl-3-isoxazolyl)-2-O-(5-methyl-3-isoxazolyl)-3-O-(7-hydroxyheptyl)glycerol (prepared as described in Preparation 37) and 0.35 ml of triethylamine in 15 ml of benzene, whilst ice-cooling. The mixture was then stirred at room temperature for 1 hour after which it was washed with water, dried and concentrated by evaporation under reduced pressure. The residue was dissolved in 1 ml of toluene, and 0.89 ml of thiazole was added to the solution, which was then heated at 80° C. for 4 days, whilst stirring. The toluene was distilled off, and the residue was subjected to column chromatography through 20 g of silica gel. 0.697 g of the title compound was obtained as a viscous oil from the fractions eluted with mixtures of methanol and methylene chloride ranging from 1:9 to 1:4 by volume.

Nuclear Magnetic Resonance Spectrum (CD$_3$OD) δ ppm: 0.7–2.2 (39H, multiplet); 2.31 (3H, singlet); 2.63 (2H, triplet, J=7 Hz); 2.66 (3H, singlet); 3.49 (2H, triplet, J=6 Hz); 3.75 (2H, doublet, J=4.5 Hz); 4.3–4.7 (4H, multiplet); 5.02 (1H, multiplet); 5.80 (2H, singlet); 8.31 (1H, doublet, J=4 Hz); 8.51 (1H, doublet, J=4 Hz).

Elemental analysis: Calculated for $C_{36}H_{61}N_3O_8S_2 \cdot H_2O$: C, 57.96%; H, 8.51%; N, 5.63%; S, 8.60%. Found: C, 57.73%; H, 8.48%; N, 5.68%; S, 8.53%.

EXAMPLE 25

(2RS)-1-O-(5-Pentadecyl-3-isoxazolyl)-2-O-(5-methyl-3-isoxazolyl)-3-O-{N-(5-thiazoliopentyl)carbamoyl} glycerol bromide 25(a) A solution of 0.976 g of 6-bromohexanoic acid, 1.08 ml of diphenylphosphoryl azide and 0.70 ml of triethylamine in 15 ml of benzene was heated under reflux for 3 hours. At the end of this time, the reaction mixture was cooled, washed with a saturated aqueous solution of sodium bicarbonate and with water, dried and evaporated to dryness under reduced pressure. The residue was dissolved in 30 ml of toluene, and 0.900 g of (2RS)-1-O-(5-pentadecyl-3-isoxazolyl)-2-O-(5-methyl-3-isoxazolyl)glycerol (prepared as described in Preparation 35) and 0.70 ml of triethylamine were added to the resulting solution. The mixture was then heated at 85° C. for 18 hours, whilst stirring. The mixture was allowed to cool, and the solvent was distilling off. The residue was subjected to column chromatography through 30 g of silica gel. 1.043 g of (2RS)-1-O-(5-pentadecyl-3-isoxazolyl)-2-O-(5-methyl-3-isoxazolyl)-3-O-{N-(5-bromopentyl)carbamoyl}glycerol was obtained from the fractions eluted with mixtures of hexane and diethyl ether ranging from 3:1 to 2:1. It yielded white needles melting at 46°–48° C. on recrystallization from hexane.

Nuclear Magnetic Resonance Spectrum (CDCl$_3$) δ ppm: 0.7–2.1 (35H, multiplet); 2.33 (3H, singlet); 2.61 (2H, triplet, J=7 Hz); 3.18 (2H, multiplet); 3.39 (2H, triplet, J=7 Hz); 4.2–4.6 (4H, multiplet); 4.78 (1H, multiplet); 5.20 (1H, multiplet); 5.63 (1H, singlet); 5.67 (1H, singlet).

Infrared Absorption Spectrum $\nu_{max}$cm$^{-1}$: 3460 (—NH—) and 1725 (—O—CO—N—).

Mass spectrum (m/e): 643, 641 (M$^+$) and 562 (M$^+$ − Br).

Elemental analysis: Calculated for $C_{31}H_{52}BrN_3O_6$: C, 57.93%; H, 8.15%; Br, 12.43%; N, 6.54%. Found: C, 58.16%; H, 7.78%; Br, 12.17%; N, 6.71%.

25(b) 0.643 g of (2RS)-1-O-(5-pentadecyl-3-isoxazolyl)-2-O-(5-methyl-3-isoxazolyl)-3-O-{N-(5-bromopentyl)carbamoyl}glycerol [prepared as described in step (a) above] and 0.71 ml of thiazole were dissolved in 2 ml of toluene, and the mixture was stirred at 75° C. for 4 days. At the end of this time, the reaction mixture was cooled and subjected to column chromatography through 25 g of silica gel. 0.425 g of the title compound was isolated as a resinous material from the fractions eluted with a 5:1 by volume mixture of methylene chloride and methanol.

Nuclear Magnetic Resonance Spectrum (CD$_3$OD) δ ppm: 0.7–2.2 (35H, multiplet); 2.31 (3H, singlet); 2.65 (2H, triplet, J=7 Hz); 3.10 (2H, triplet. J=6 Hz); 4.2–4.7 (6H, multiplet); 5.02 (1H, multiplet); 5.82 (2H, singlet); 8.33 (1H, doublet, J=4 Hz); 8.55 (1H, doublet, J=4 Hz).

Elemental analysis: Calculated for $C_{34}H_{55}BrN_4O_6S \cdot 3/2H_2O$: C, 54.10%; H, 7.34%; N, 7.42%; S, 4.25%. Found: C, 54.10%; H, 7.59%; N, 7.27%; S, 4.17%.

EXAMPLE 26

(2RS)-1-O-(5-pentadecyl-3-isoxazolyl)-2-O-(5-methyl-3-isoxazolyl)-3-O-{N-(5-trimethylammoniopentyl)carbamoyl}glycerol bromide 3 g of gaseous trimethylamine was introduced into a solution of 0.510 g of (2RS)-1-O-(5-pentadecyl-3-isoxazolyl)-2-O-(5-methyl-3-isoxazolyl)-3-O-{N-(5-bromopentyl)carbamoyl}glycerol [obtained as described in Example 25(a)] dissolved in 13 ml of a 5:5:3 by volume mixture of dimethylformamide, isopropanol and chloroform. The reaction mixture was then heated at 50° C. for 6 hours in an atmosphere of nitrogen, after which it was cooled and the solvent was distilled off. The residue was subjected to column chromatography through 20 g of silica gel. 0.425 g of the title compound was isolated as a resinous material from the fractions eluted with a 5:1 by volume mixture of methylene chloride and methanol.

Nuclear Magnetic Resonance Spectrum (CD$_3$OD) δ ppm: 0.7–2.1 (35H, multiplet); 2.33 (3H, singlet); 2.65 (2H, triplet, J=7 Hz); 3.17 (9H, singlet); 2.8–3.6 (4H, multiplet); 4.1–4.7 (4H, multiplet); 5.13 (1H, multiplet); 5.82 (2H, singlet).

Elemental analysis: Calculated for $C_{34}H_{61}BrN_4O_6 \cdot 2H_2O$: C, 55.42%; H, 8.89%; N, 7.60%. Found: C, 55.72%; H, 8.61%; N, 7.43%.

EXAMPLE 27

(2RS)-2-(5-Methyl-3-isoxazolyloxy)-3-(5-pentadecyl-3-isoxazolyloxy)propyl N-(5-aminopentyl)carbamate 1.423 g of (2RS)-(5-methyl-3-isoxazolyloxy)-3-(5-pentadecyl-3-isoxazolyloxy)propyl N-[5-(t-butoxycarbonylamino)pentyl]carbamate (prepared as described in Preparation 38) was dissolved in 10 ml of trifluoroacetic acid, whilst ice-cooling, and the mixture was stirred for 30 minutes at 2°–3° C. The solvent was removed by evaporation under reduced pressure, and then 15 ml of a saturated aqueous solution of sodium bicarbonate were added to the residue. The mixture was then extracted three times with ethyl acetate. The combined extracts were washed with water, dried and concentrated by evaporation under reduced pressure to give 1.110 g of the title compound as a powder.

Nuclear Magnetic Resonance Spectrum (CDCl$_3$) δ ppm: 0.75–2.0 (35H, multiplet); 2.29 (3H, singlet); 2.60 (2H, triplet, J=7 Hz); 2.8–3.4 (4H, multiplet); 4.2–4.7 (4H, multiplet); 4.9–5.5 (2H multiplet); 5.61 (1H, singlet); 5.67 (1H, singlet); 6.2–7.2 (2H, multiplet).

Mass Spectrum (m/e): 578 (M+) and 550 (M+ −CO).

EXAMPLE 28

(2RS)-2-(5-Methyl-3-isoxazolyloxy)-3-(5-pentadecyl-3-isoxazolyloxy)propyl N-[5-(1-imidazolyl)pentyl]carbamate 0.043 g of sodium hydride (as a 55% w/w suspension in mineral oil) was added to a solution of 0.068 g of imidazole dissolved in 2 ml of dimethylformamide, and the mixture was stirred at room temperature for 1 hour. A solution of 0.347 g of (2RS)-1-O-(5-pentadecyl-3-isoxazolyl)-2-O-(5-methyl-3-isoxazolyl)-3-O-[N-(5-bromopentyl)carbamoyl]glycerol [prepared as described in Example 25(a)] dissolved in 3 ml of dimethylformamide was then added to the resulting mixture. The mixture was then stirred at room temperature for 16 hours, after which it was poured into 20 ml of water and then extracted twice with ethyl acetate. The combined extracts were washed with water, dried and concentrated by evaporation under reduced pressure. The residue was subjected to column chromatography through 20 g of silica gel. 0.150 g of the title compound was obtained as an oil from the fractions eluted with mixtures of methylene chloride and methanol ranging from 20:1 to 10:1 by volume.

Nuclear Magnetic Resonance Spectrum (CDCl$_3$) δ ppm: 0.75–2.1 (35H, multiplet); 2.30 (3H, singlet); 2.60 (2H, triplet, J=7 Hz); 2.85–3.50 (2H, multiplet); 3.90 (2H, triplet, J=7 Hz); 4.2–4.7 (4H, multiplet); 4.8–5.4 (2H, multiplet); 5.58 (1H, singlet); 5.62 (1H, singlet); 6.88 (1H, singlet); 7.00 (1H, singlet); 7.42 (1H, singlet).

Infrared Absorption Spectrum $\nu_{max}$cm$^{-1}$: 3460, 1725.

EXAMPLE 29

(2RS)-2-(5-Methyl-3-isoxazolyloxy)-3-(5-pentadecyl-3-isoxazolyloxy)propyl N-[5-(1-tetrazolyl)pentyl]carbamate A mixture of 0.230 g of (2RS)-2-(5-methyl-3-isoxazolyloxy)-3-(5-pentadecyl-3-isoxazolyloxy)propyl N-(5-aminopentyl)carbamate (prepared as described in Example 27), 0.067 g of sodium azide, 0.30 ml of ethyl orthoformate and 0.45 ml of acetic acid was heated on an oil bath kept at 115° C. for 3 hours. The solvent was removed by evaporation under reduced pressure, and then the residue was subjected to column chromatography through 10 g of silica gel. 0.152 g of the title compound was obtained as a powder from the fractions eluted with mixtures of methylene chloride and methanol ranging from 5:1 to 2:1 by volume. It melted at 82°–84° C. (after reprecipitation from a mixture of methylene chloride and diethyl ether).

Nuclear Magnetic Resonance Spectrum (CDCl$_3$) δ ppm: 0.75–1.9 (35H, multiplet); 1.99 (2H, multiplet); 2.32 (3H, singlet); 2.60 (2H, triplet, J=7.5 Hz); 3.17 (2H, doublet of triplets, $J_1=J_2=6$ Hz); 4.15–4.70 (4H, multiplet); 4.93 (1H, multiplet); 5.20 (1H, multiplet); 5.62 (1H, singlet); 5.67 (1H, singlet); 8.67 (1H, singlet).

Mass Spectrum (m/e): 631 (M+), 450.

Elemental analysis: Calculated for $C_{32}H_{53}N_7O_6$: C, 60.83%; H, 8.46%; N, 15.60%. Found: C, 60.86%; H, 8.63%; N, 15.51%.

EXAMPLE 30

(2RS)-3-(5-Hexadecyl-3-isoxazolyloxy)-2-(3-isoxazolyloxy)propyl N-(2-oyridylmethyl)carbamate A solution of 0.387 g of phenyl chloroformate dissolved in 5 ml of methylene chloride was added dropwise to a solution of 0.743 g of (2RS)-1-O-(5-hexadecyl-3-isoxazolyl)-2-O-(3-isoxazolyl)glycerol (prepared as described in Preparation 33) and 0.27 ml of pyridine dissolved in 10 ml of methylene chloride, whilst ice-cooling. The mixture was stirred at room temperature for 40 minutes, after which it was washed with 10% w/v aqueous hydrochloric acid (twice), a 5% w/v aqueous solution of sodium bicarbonate and with water. After the mixture had been dried, it was evaporated to dryness under reduced pressure. The solid residue (1.048 g) was dissolved in 15 ml of chloroform, and 0.357 g of 2-aminomethylpyridine was added thereto. The mixture was then heated under reflux for 24 hours. The mixture was allowed to cool, and then the solvent was removed by evaporation under reduced pressure. The residue was subjected to column chromatography through 30 g of silica gel. 0.898 g of the title compound was obtained from the fractions eluted with a 10:1 by volume mixture of methylene chloride and diethyl ether. It was a white powder melting at 83°–85° C. (after reprecipitation from a mixture of methylene chloride and diethyl ether).

Nuclear Magnetic Resonance Spectrum (CDCl$_3$) δ ppm: 0.75–1.90 (31H, multiplet); 2.63 (2H, triplet J=7.5 Hz); 4.2–4.8 (6H, multiplet); 5.28 (1H, multiplet); 5.63 (1H, singlet); 5.91 (1H, multiplet); 6.03 (1H, doublet, J=2 Hz); 7.1–7.4 (2H, multiplet); 7.69 (1H, multiplet); 8.15 (1H, doublet, J=2 Hz); 8.57 (1H, doublet, J=4.5 Hz).

Mass Spectrum (m/e): 584 (M+), 500 and 450.

Elemental analysis: Calculated for $C_{32}H_{48}N_4O_6$: C, 65.72%; H, 8.27%; N, 9.58%. Found: C, 65.83%; H, 8.29%; N, 9.50%.

EXAMPLE 31

(2RS)-3-(5-Hexadecyl-3-isoxazolyloxy)-2-(3-isoxazolyloxy)propyl N-acetyl-N-(2-pyridylmethyl)carbamate 0.370 g of (2RS)-3-(5-hexadecyl-3-isoxazolyloxy)-2-(3-isoxazolyloxy)propyl N-(2-pyridylmethyl)carbamate (prepared as described in Example 30), 0.60 ml of acetic anhydride and 0.733 g of 4-(N,N-dimethylamino)pyridine were dissolved in 10 ml of toluene, and the mixture was stirred on an oil bath kept at 90° C. for 48 hours. The solvent was distilled off, and the residue was purified by column chromatography through 15 g of silica gel and by medium pressure liquid chromatography using a Lobar B column, 0.308 g of the title compound was obtained, as an oil, from the fractions eluted with methylene chloride.

Nuclear Magnetic Resonance Spectrum (CDCl$_3$) δ ppm: 0.75–1.90 (31H, multiplet); 2.53 (2H, triplet, J=7.5 Hz); 2.60 (3H, singlet); 4.38 (2H, doublet, J=4.5 Hz); 4.4–4.8 (2H, multiplet); 5.08 (2H, singlet); 5.20 (1H, multiplet); 5.58 (1H, singlet); 5.90 (1H, doublet, J=2 Hz); 7.10 (2H, multiplet); 7.60 (1H, multiplet); 8.11 (1H, doublet, J=2 Hz); 8.49 (1H, multiplet).

Infrared Absorption Spectrum $\nu_{max}$cm$^{-1}$: 1745 and 1700.

Mass Spectrum (m/e): 626 (M+) 584, 542 and 499.

Elemental analysis: Calculated for $C_{34}H_{50}N_4O_7$: C, 65.15%; H, 8.04%; N, 8.94%. Found: C, 64.94%; H, 8.05%; N, 8.89%.

EXAMPLE 32

2-{N-Acetyl-N-[(2RS)-3-(5-hexadecyl-3-isoxazolyloxy)-2-(3-isoxazolyloxy)propoxycarbonyl]aminomethyl}-1-ethylpyridinium chloride 0.270 g of (2RS)-3-(5-hexadecyl-3-isoxazolyloxy)-2-(3-isoxazolyloxy)propyl N-acetyl-N-(2-pyridylmethyl)-carbamate (prepared as described in Example 31) was dissolved in 6 ml of ethyl iodide, and the mixture was heated on an oil bath kept at 75° C. for 48 hours. The ethyl iodide was distilled off, and the oily residue (0.308 g) was dissolved in a 7:3 by volume mixture of methanol and water and the solution was passed through a column containing 30 ml of IRA-410 resin (Cl type, Rhom & Haas Co.). The resin in the column was washed with a 7:3 by volume mixture of methanol and water. A mixture of the eluate and the washings was evaporated to dryness. The residue was subjected to column chromatography through 15 g of silica gel. 0.188 g of the title compound was obtained from the fractions eluted with mixtures of methylene chloride and methanol ranging from 10:1 to 9:1 by volume, as a powder melting at 36°–41° C.

Nuclear Magnetic Resonance Spectrum (CD$_3$OD) δ ppm: 0.75–1.80 (31H, multiplet); 1.65 (2H, triplet, J=7 Hz); 2.61 (3H, singlet); 2.63 (2H, triplet, J=7.5 Hz); 4.2–5.0 (6H, multiplet); 5.25 (1H, multiplet); 5.32 (2H, singlet); 5.80 (1H, singlet); 6.10 (1H, doublet, J=2 Hz); 7.98 (2H, multiplet); 8.40 (1H, doublet, J=2 Hz); 8.48 (1H, multiplet); 9.03 (1H, d, J=6 Hz).

Infrared Absorption Spectrum $\nu_{max}$cm$^{-1}$: 1760 and 1720.

Elemental analysis: Calculated for $C_{36}H_{55}ClN_4O_7 \cdot 1.5H_2O$: C, 61.04%; H, 8.25%; Cl, 5.01%; N, 7.80%. Found: C, 60.77%; H, 8.34%; Cl, 5.44%; N, 7.80%.

EXAMPLE 33

3-{5-[(2RS)-3-(N-Heptadecylcarbamoyloxy)-2-(5-methyl-3-isoxazolyloxy)propoxycarbonylamino]pentyl} thiazolium bromide 33(a) 1.212 g of (2RS)-3-(N-heptadecylcarbamoyloxy)-2-(5-methyl-3-isoxazolyloxy)propyl N-(5-bromopentyl)carbamate was obtained from 1.000 g of (2RS)-1-O-(N-heptadecylcarbamoyl)-2-O-(5-methyl-3-isoxazolyl)-glycerol (prepared as described in Preparation 21) by a similar procedure to that described in Example 25(a), as a white solid melting at 78°–80° C.

Nuclear Magnetic Resonance Spectrum (CDCl$_3$) δ ppm: 0.75–1.80 (37H, multiplet); 1.87 (2H, multiplet); 2.31 (3H, singlet); 3.15 (4H, multiplet); 3.38 (2H, triplet, J=7 Hz); 4.1–4.6 (4H, multiplet); 4.77 (2H, multiplet); 5.07 (1H, multiplet); 5.65 (1H, singlet).

Infrared Absorption Spectrum $\nu_{max}$cm$^{-1}$: 3460 and 1725.

Mass Spectrum (m/e): 647, 645 (M+), 549 and 547.

Elemental analysis: Calculated for $C_{31}H_{56}BrN_3O_6$: C, 57.57%; H, 8.73%; N, 6.50%; Br, 12.36%. Found: C. 57.63%; H, 8.50%; N, 6.39%; Br, 12.29%.

33(b) 0.388 g of the title compound was prepared, as a powder, by reacting 0.600 g of (2RS)-3-(N-heptadecylcarbamoyloxy)-2-(5-methyl-3-isoxazolyloxy)-propyl N-(5-bromopentyl)carbamate [prepared as described in step (a) above] with 0.66 ml of thiazole by a similar procedure to that described in Example 25(b).

Nuclear Magnetic Resonance Spectrum (CD$_3$OD) δ ppm: 0.75–1.80 (37H, multiplet); 2.02 (2H, multiplet); 2.31 (3H, singlet); 3.08 (4H, multiplet); 4.1–4.6 (4H, multiplet); 4.63 (2H, triplet J=7 Hz); 4.97 (1H, multiplet); 5.81 (1H, singlet); 8.32 (1H, doublet, J=4 Hz); 8.54 (1H, doublet, J=4 Hz).

EXAMPLE 34

(2RS)-3-(N-Heptadecylcarbamoyloxy)-2-(3-isoxazolyloxy)propyl N-(2-pyridylmethyl)carbamate 1.230 g of the title compound was obtained from 1.000 g of (2RS)-1-O-(N-heptadecylcarbamoyl)-2-O-(3-isoxazolyl)glycerol (prepared as described in Preparation 13) by a similar procedure to that described in Example 30, as a powder melting at 84°–85° C. (on reprecipitation from a mixture of hexane and methylene chloride).

Nuclear Magnetic Resonance Spectrum (CDCl$_3$) δ ppm: 0.75–2.15 (33H, multiplet); 3.13 (2H, doublet of triplets, J$_1$=J$_2$=7 Hz); 4.2–4.65 (6H, multiplet); 4.77 (1H, multiplet); 5.12 (1H, multiplet); 5.92 (1H, multiplet); 5.96 (1H, doublet, J=2 Hz); 7.05–7.4 (2H, multiplet); 7.65 (1H, multiplet); 8.10 (1H, doublet, J=2 Hz); 8.53 (1H, multiplet).

Infrared Absorption Spectrum ν$_{max}$cm$^{-1}$: 3460 and 1725.

Mass Spectrum (m/e): 574 (M+) and 490.

Elemental analysis: Calculated for C$_{31}$H$_{50}$N$_4$O$_6$: C, 64.78%; H, 8.77%; N, 9.75%. Found: C, 64.73%; H, 8.85%; N, 9.75%.

EXAMPLE 35

(2R)-3-(N-Heptadecylcarbamoyloxy)-2-(3-isoxazolyloxy)propyl N-(2-pyridylmethyl)carbamate 1.764 g of the title compound was prepared from 1.500 g of 1-O-(N-heptadecylcarbamoyl)-2-O-(3-isoxazolyl)-sn-glycerol (prepared as described in Preparation 18) by a similar procedure to that described in Example 30, as a powder melting at 89°–90° C. (on reprecipitation from a mixture of hexane and methylene chloride).

[α]$^{26}$+0.79° (c=1.01, CHCl$_3$).

Elemental analysis: Calculated for C$_{31}$H$_{50}$N$_4$O$_6$: C, 64.78%; H, 8.77%; N, 9.75%. Found: C, 64.50%; H, 8.94%; N, 9.66%.

EXAMPLE 36

(2RS)-3-(n-Heptadecylcarbamoyloxy)-2-(3-isoxazolyloxy)propyl [N-acetyl-N-(2-pyridylmethyl)]carbamate 0.665 g of the title compound was obtained by acetylation of 1.205 g of (2RS)-3-(N-heptadecylcarbamoyloxy)- 2-(3-isoxazolyloxy)propyl N-(2-pyridylmethyl)carbamate (prepared as described in Example 34) by a similar procedure to that described in Example 31, as a waxy material.

Nuclear Magnetic Resonance Spectrum (CDCl$_3$) δ ppm: 0.75–2.20 (33H, multiplet); 2.60 (3H, singlet); 3.26 (2H, doublet of triplets, J$_1$=J$_2$=7 Hz); 4.0–4.7 (4H, multiplet); 4.75–5.1 (2H, multiplet); 5.07 (2H, singlet); 5.87 (1H, doublet, J=2 Hz); 7.0–7.2 (2H, multiplet); 7.60 (1H, multiplet); 8.10 (1H, doublet, J=2 Hz); 8.50 (1H, multiplet).

Mass Spectrum (m/e): 616 (M+), 574, 573 and 532.

Elemental analysis: Calculated for C$_{33}$H$_{52}$N$_4$O$_7$: C, 64.26%; H, 8.50%; N, 9.08%. Found: C, 64.10%; H, 8.65%; N, 8.81%.

EXAMPLE 37

(2R)-3-(N-Heptadecylcarbamoyloxy)-2-(3-isoxazolyloxy)propyl [N-acetyl-N-(2-pyridylmethyl)]carbamate 0.737 g of the title compound was prepared from 1.534 g of (2R)-3-(N-heptadecylcarbamoyloxy)-2-(3-isoxazolyloxy)propyl N-(2-pyridylmethyl)carbamate (prepared as described in Example 35) by a similar procedure to that described in Example 31, as a powder melting at 62°–63° C.

[α]$^{26}$ −1.78° (c=1.01, CHCl$_3$).

Elemental analysis:
Calculated for C$_{33}$H$_{52}$N$_4$O$_7$: C, 64.26%; H, 8.50%; N, 9.08%.
Found: C, 64.18%; H, 8.52%; N, 9.13%.

EXAMPLE 38

2-{N-Acetyl-N-[(2RS)-3-(N-Heptadecylcarbamoyloxy)-2-(3-isoxazolyloxy)propoxycarbonyl]aminomethyl}-1-ethylpyridinium chloride 0.364 g of the title compound was obtained from 0.633 g of (2RS)-3-(N-heptadecylcarbamoyloxy)-2-(3-isoxazolyloxy)propyl [N-acetyl-N-(2-pyridylmethyl)-]carbamate (prepared as described in Example 36), as a powder, by following a procedure similar to that described in Example 32.

Nuclear Magnetic Resonance Spectrum (CD$_3$OD) δ ppm: 0.75–1.80 (33H, multiplet); 1.66 (2H, triplet, J=7 Hz); 2.62 (3H, singlet); 3.05 (2H, triplet, J=7.5 Hz); 4.0–4.8 (4H, multiplet); 4.75 (2H, quartet, J=7 Hz); 5.12 (1H, multiplet); 5.41 (2H, singlet); 6.06 (1H, doublet, J=2 Hz); 7.8–8.15 (2H, doublet); 8.37 (1H, doublet, J=2 Hz); 8.47 (1H, multiplet); 9.01 (1H, doublet, J=6 Hz).

Elemental analysis: Calculated for C$_{35}$H$_{57}$ClN$_4$O$_7$·H$_2$O: C, 60.11%; H, 8.50%; N, 8.01%. Found: C, 60.14%; H, 8.21%; N, 7.73%.

EXAMPLE 39

2-{N-Acetyl-N-[(2R)-3-(N-heotadecylcarbamoyloxy)-2-(3-isoxazolyloxy)propoxycarbonyl]aminomethyl}-1-ethylpyridinium chloride 0.488 g of the title compound was obtained from 0.639 g of (2R)-3-(N-heptadecylcarbamoyloxy)-2-(3-isoxazolyloxy)propyl [N-acetyl-N-(2-pyridylmethyl)-]carbamate (prepared as described in Example 37), as a powder, by following a procedure similar to that described in Example 32.

[α]$^{26}$−6.10° (c=1.03, CH$_3$OH).

Elemental Analysis: Calculated for C$_{35}$H$_{57}$ClN$_4$O$_7$·H$_2$O: C, 60.11%; H, 8.50%; N, 8.01%. Found: C, 60.11%; H, 8.21%; N, 7.96%.

EXAMPLE 40

3-{(6RS)-6-Carboxy-7-[(2RS)-2-(5-methyl-3-isoxazolyloxy)-3-(5-pentadecyl-3-isoxazolyloxy)propoxy]-heptyl}thiazolium iodide A solution of 0.105 g of (2RS)-7-iodo-2-[(2RS)-2-(5-methyl- 3-isoxazolyloxy)-3-(5-pentadecyl-3-isoxazolyloxy)propoxy]methylheptanoic acid (prepared as described in Preparation 47) and 0.21 ml of thiazole dissolved in 1 ml of toluene was heated on an oil bath kept at 80° C. for 90 hours. The solvent was distilled off, and the residue was subjected to column chromatography through 2 g of silica gel. 0.036 g of the title compound was obtained from the fractions eluted with mixtures of methylene chloride and methanol ranging from 49:1 to 19:1 by volume, as a viscous oil.

Nuclear Magnetic Resonance Spectrum (CD$_3$OD) δ ppm: 0.8–1.8 (39H, multiplet); 2.01 (2H, multiplet); 2.32 (3H, singlet); 2.45–2.7 (1H, multiplet); 2.64 (2H, triplet, J=7.5 Hz); 3.4–4.2 (4H, multiplet); 4.2–4.6 (2H, multiplet); 4.63 (2H, triplet, J=7.5 Hz); 5.02 (1H, multiplet); 5.81 (2H, singlet); 8.32 (2H, doublet, J=4 Hz); 8.55 (2H, doublet, J=4 Hz).

EXAMPLE 41

3-{(6RS)-6-Ethoxycarbonyl-6-[(2RS)-3-(5-hexadecyl-3-isoxazolyloxy)-2-(3-isoxazolyloxy)propoxy]carbonylaminohexyl}thiazolium methanesulfonate 0.229 g of the corresponding crude methanesulfonate was obtained from 0.211 g of (2RS)-3-(5-hexadecyl-3-isoxazolyloxy)-2-(3-isoxazolyloxy)propyl N-[(1RS)-1-ethoxycarbonyl-6-hydroxyhexyl]carbamate (prepared as described in Preparation 50) in a similar manner to that described in Preparation 2(a). The methanesulfonate and 0.24 ml of thiazole were dissolved in 2 ml toluene, and the mixture was heated on an oil bath kept at 85° C. for 4 days. The solvent was distilled off, and the residue was subjected to column chromatography through 8 g of silica gel. 0.114 g of the title compound was obtained from the fractions eluted with a 2:1 by volume mixture of methylene chloride and methanol as a viscous oil.

Nuclear Magnetic Resonance Spectrum (CDCl$_3$) δ ppm: 0.7-2.2 (42H, multiplet); 2.60 (3H, triplet, J=7 Hz); 2.75 (3H, singlet); 4.14 (2H, quartet, J=7 Hz); 3.8-4.9 (7H, multiplet); 5.18 (1H, multiplet); 5.61 (1H, singlet); 6.00 (1H, doublet, J=2 Hz); 6.15 (1H, multiplet); 8.15 (1H, doublet, J=2 Hz); 8.34 (1H, multiplet); 8.57 (1H, multiplet); 10.85 (1H, multiplet).

PREPARATION 1

(2RS)-1-O-Octadecyl-2-O-(2-thiazolyl)glycerol

A solution of 3.865 g of RS-1-O-octadecyl-3-O-triphenylmethylglycerol in 25 ml of dimethylformamide was added dropwise to a suspension of 0.287 g of sodium hydride (as a 55% w/w dispersion in mineral oil) in 15 ml of dimethylformamide over a period of 10 minutes, whilst ice-cooling. The mixture was stirred at 60° C. for 45 minutes, after which it was allowed to cool to room temperature, and a solution of 1.080 g of 2-bromothiazole in 5 ml of dimethylformamide was added. The reaction mixture was then stirred at 60° C. for 5.5 hours and poured into water. The aqueous mixture was extracted three times with ethyl acetate. The combined extracts were washed with water, dried and concentrated by evaporation under reduced pressure. The residue (5.1 g) was subjected to column chromatography through 150 g of silica gel. 1.212 g of crude RS-1-O-octadecyl-2-O-(2-thiazolyl)-3-O-triphenylmethylglycerol was isolated from the fractions eluted with a 3:100 by volume mixture of diethyl ether and petroleum ether.

The whole of this compound was dissolved in 20 ml of methylene chloride. 5 ml of trifluoroacetic acid were added to the solution, and the mixture was stirred at room temperature for 1 hour and then poured into a cooled aqueous solution of sodium bicarbonate. The aqueous mixture was extracted twice with methylene chloride. The combined extracts were washed with water, dried and concentrated by evaporation under reduced pressure. The residue (2.2 g) was subjected to column chromatography through 40 g of silica gel. 1.087 g of the title compound was obtained as white needles from the fractions eluted with a 9:1:3 by volume mixture of hexane, methylene chloride and ethyl acetate. It melted at 65°-67° C. after recrystallization from a mixture of diethyl ether and hexane.

Nuclear Magnetic Resonance Spectrum (CDCl$_3$) δ ppm: 0.7-1.8 (35H, multiplet); 1.53 (1H, singlet); 3.47 (2H, triplet, J=7 Hz); 3.74 (2H, doublet, J=5 Hz); 3.93 (2H, doublet, J=5 Hz); 5.10 (1H, quintet, J=5 Hz); 6.68 (1H, doublet, J=4.5 Hz); 7.07 (1H, doublet, J=4.5 Hz).

Mass spectrum (m/e): 428 (M$^+$).

Elemental analysis: Calculated for C$_{24}$H$_{45}$NO$_3$S: C, 67.40%; H, 10.61%; N, 3.27%; S, 7.50%.

Found: C, 67.49%; H, 10.63%; N, 3.33%; S, 7.66%.

PREPARATION 2

(2RS)-1O-Octadecyl-2O-(3-isoxazolyl)glycerol

2(a) A solution of 0.58 ml of methanesulfonyl chloride in 30 ml of benzene was added dropwise to a solution of 3.696 g of RS-1-O-octadecyl-3-O-triphenylmethylglycerol and 1.23 ml of triethylamine in 40 ml of benzene over a period of 5 minutes, whilst ice-cooling. The mixture was then stirred at room temperature for 1 hour, after which it was washed with water, dried and concentrated by evaporation under reduced pressure to give 4.18 g of a crude mesylate as a solid.

Nuclear Magnetic Resonance Spectrum (CDCl$_3$) δ ppm: 0.7-1.7 (35H, multiplet); 3.02 (3H, singlet); 3.25-3.80 (6H, multiplet); 4.83 (1H, multiplet); 7.2-7.8 (15H, multiplet).

2(b) A solution of 0.711 g of 3-hydroxyisoxazole in 20 ml of dimethylformamide was added dropwise, whilst ice-cooling, to a suspension of 0.365 g of sodium hydride (as a 55% w/w dispersion in mineral oil) in 20 ml of dimethylformamide over a period of 10 minutes. The mixture was stirred at room temperature for 1 hour, after which a solution of 3.704 g of the crude mesylate [prepared as described in step (a) above] dissolved in 30 ml of dimethylformamide was added to it, and then the mixture was heated on an oil bath kept at 100° C. for 65 hours. The reaction mixture was allowed to cool, poured into water and extracted twice with ethyl acetate. The combined extracts were washed with water, dried and concentrated by evaporation under reduced pressure. The residue (4.61 g) was subjected to column chromatography through 120 g of silica gel. 2.120 g of RS-1-O-octadecyl-2-O-(3-isoxazolyl)-3-O-triphenylmethylglycerol was isolated as a solid from the fractions eluted with mixtures of hexane and diethyl ether ranging from 9:1 to 8:1 by volume.

Nuclear Magnetic Resonance Spectrum (CDCl$_3$) δ ppm: 0.7-1.8 (35H, multiplet); 3.15-3.65 (4H, multiplet); 3.75 (2H, doublet, J=5 Hz); 5.00 (1H, multiplet); 5.98 (1H, doublet, J=2 Hz); 7.1-7.6 (15H, multiplet); 8.10 (1H, doublet, J=2 Hz).

2(c) 0.185 g of p-toluenesulfonic acid was added to a solution of 2.120 g of RS-1-O-octadecyl-2-O-(3-isoxazolyl)-3-O-triphenylmethylglycerol [prepared as described in step (b) above] in 95% v/v aqueous methanol, and the mixture was heated under reflux for 2 hours. After cooling, the mixture was mixed with 20 ml of a saturated aqueous solution of sodium bicarbonate, and then the methanol of the solvent was stripped off under reduced pressure. The aqueous residue was extracted with ethyl acetate, and the extract was washed with water, dried and concentrated by evaporation under reduced pressure. The oily residue was subjected to column chromatography through 70 g of silica gel. 1.313 g of the title compound was isolated as white crystals melting at 52°-53° C. from the fractions eluted with mixtures of diethyl ether and hexane ranging from 1:3 to 1:2 by volume.

Nuclear Magnetic Resonance Spectrum (CDCl$_3$) δ ppm: 0.7-1.8 (35H, multiplet); 2.30 (1H, multiplet); 3.52 (2H, triplet, J=6 Hz); 3.78 (2H, doublet, J=5 Hz); 3.95

(2H, doublet, J=5 Hz); 4.86 (1H, quintet, J=5 Hz); 6.00 (1H, doublet, J=2 Hz); 8.12 (1H, doublet, J=2 Hz).

Mass spectrum (m/e): 412 (M$^+$+1).

Elemental analysis: Calculated for $C_{24}H_{45}NO_4$: C, 70.03%; H, 11.02%; N, 3.40%. Found: C, 69.80%; H, 11.19%; N, 3.19%.

PREPARATION 3

(2RS)-1-O-Hexadecyl-2-O-(3-isoxazolyl)glycerol

3(a) Following a similar procedure to that described in Preparation 2, 2.283 g of the title compound were prepared as white needles melting at 49°–50° C. (on recrystallization from hexane) from 8.20 g of RS-1-O-hexadecyl-3-O-triphenylmethylglycerol.

Nuclear Magnetic Resonance Spectrum (CDCl$_3$) δ ppm: 0.7–1.8 (31H, multiplet); 2.58 (1H, triplet, J=7 Hz); 3.47 (2H, triplet, J=6 Hz); 3.77 (2H, doublet, J=5 Hz); 3.95 (2H, doublet of doublets, J$_1$=5, J$_2$=7 Hz); 4.87 (1H, quintet, J=5 Hz); 6.00 (1H, doublet, J=2 Hz); 8.13 (1H, doublet, J=2 Hz).

Mass spectrum (m/e): 384 (M$^+$+1) and 383 (M$^+$).

Elemental analysis: Calculated for $C_{22}H_{41}NO_4$: C, 68.89%; H, 10.77%; N, 3.65%. Found: C, 68.71%; H, 10.78%; N, 3.62%.

3(b) To a solution of 2.482 g of (2RS)-1-O-hexadecyl-3-O-triphenylmethylglycerol, 0.453 g of 3-hydroxyisoxazole and 2.330 g of triphenylphosphine dissolved in 18 ml of tetrahydrofuran was added all at once a solution of 1.289 g of dimethyl azodicarboxylate dissolved in 2 ml of tetrahydrofuran. The temperature of the reaction mixture rose from 20° C. to 34° C. The mixture was stirred at 20° C. to 24° C. for 30 minutes, after which the solvent was removed by evaporation under reduced pressure, and the residue was subjected to column chromatography through 130 g of silica gel. 2.669 g of (2RS)-1-O-hexadecyl-2-O-(3-isoxazolyl)-3-O-triphenylmethylglycerol were obtained from the fractions eluted with mixtures of hexane and diethyl ether ranging from 100:7 to 10:1 by volume, as white crystals melting at 67°–68° C. (from hexane).

Nuclear Magnetic Resonance Spectrum (CDCl$_3$) δ ppm: 0.7–1.8 (31H, multiplet); 3.15–3.65 (2H, multiplet); 3.41 (2H, triplet, J=6 Hz); 3.77 (2H, doublet, J=5 Hz); 5.00 (1H, multiplet); 5.98 (1H, doublet, J=1.5 Hz); 7.1–7.7 (15H, multiplet); 8.10 (1H, doublet, J=1.5 Hz).

Mass Spectrum (m/e): 625 (M$^+$), 548, 382 and 366.

Elemental analysis: Calculated for $C_{41}H_{55}NO_4$: C, 78.68%; H, 8.86%; N, 2.24%. Found: C, 78.44%; H, 8.91%; N, 2.40%.

A mixture of 2.404 g of (2RS)-1-O-hexadecyl-2-O-(3-isoxazolyl)-3-O-triphenylmethylglycerol, prepared as described above, 0.20 g of p-toluenesulfonic acid, 45 ml of methanol and 5 ml of water was heated under reflux for one hour. After cooling the mixture, a saturated aqueous solution (about 30 ml) of sodium bicarbonate was added to it, and the methanol was removed by evaporation under reduced pressure. The residual mixture was extracted three times with methylene chloride. The combined extracts were washed with water, dried and concentrated by evaporation under reduced pressure. The residue (2.50 g) was subjected to column chromatography through 75 g of silica gel, and 1.459 g of the title compound was obtained from the fractions eluted with mixtures of hexane and diethyl ether ranging from 2:1 to 1:1. Its properties were the same as those of the product obtained as described in (a) above.

PREPARATION 4

1-O-Hexadecyl-2-O-(3-isoxazolyl)-sn-glycerol

1-O-Hexadecyl-2-O-(3-isoxazolyl)-3-O-triphenylmethyl-sn-glycerol (8.751 g) was obtained from 9.021 g of 3-O-hexadecyl-1-O-triphenylmethyl-sn-glycerol {[α]$^{26}$−2.25° (C=1.02, CHCl$_3$)} by a similar procedure to that described in the first half of Preparation 3(b), as crystals melting at 67°–68° C. (from hexane).

[α]$^{26}$+13.6° (C=1.02, CHCl$_3$).

Elemental analysis: Calculated for $C_{41}H_{55}NO_4$: C, 78.68%; H, 8.86%; N, 2.24%. Found C: 78.61%; H, 8.80%; N, 2.21%.

The triphenylmethyl group was removed from 4.271 g of the compound described above by a similar procedure to that described in the latter half of Preparation 3(b), to give 2.560 g of the title compound as crystals melting at 50°–51° C. (from hexane).

[α]$^{26}$−6.24° (c=1.01, CHCl$_3$).

Elemental analysis: Calculated for $C_{22}H_{41}NO_4$: C, 68.89%; H, 10.77%; N, 3.65%. Found C, 68.69%; H, 10.74%; N, 3.69%.

PREPARATION 5

3-O-Hexadecyl-2-O-(3-isoxazolyl)-sn-glycerol 4.400 g of 1-O-hexadecyl-2-O-(3-isoxazolyl)-3-O-triphenylmethyl-sn-glycerol described in Preparation 4 was dissolved in a mixture of 10 ml of tetrahydrofuran and 90 ml of ethanol and the solution was placed in a Paar apparatus and then shaken in the presence of 4.40 g of 10% w/w palladium-on-carbon in an atmosphere of hydrogen at 4 times atmospheric pressure for 49 hours. After removing the catalyst by filtration, 0.635 g of potassium carbonate was added to the reaction mixture, and the mixture was stirred at room temperature for 30 minutes. After filtering off the insoluble material, the solvent was distilled off and the residue was subjected to column chromatography through 100 g of silica gel. 3.327 g of 1-O-hexadecyl-3-O-triphenylmethyl-sn-glycerol was obtained from the fractions eluted with mixtures of hexane and diethyl ether ranging from 19:1 to 9:1 by volume, as white crystals melting at 49°–50° C.

[α]$^{26}$+2.25° (c=1.02, CHCl$_3$).

Starting from 3.077 g of the compound described above, 3.070 g of 3-O-hexadecyl-2-O-(3-isoxazolyl)-1-O-triphenylmethyl-sn-glycerol was obtained by a similar procedure to that described in the first half of Preparation 3(b), as white crystals melting at 67°–68° C. (from hexane).

[α]$^{26}$−13.5° (c=1.02, CHCl$_3$).

Elemental analysis: Calculated for $C_{41}H_{55}NO_4$: C, 78.68%; H, 8.86%; N, 2.24%. Found C, 78.54%; H, 8.81%; N, 2.31%.

The triphenylmethyl group was removed from 2.921 g of the said compound in a similar manner to that described in the latter half of Preparation 3(b), to give 1.736 g of the title compound as white crystals melting at 50°–51° C.

[α]$^{26}$+6.24° (c=1.01, CHCl$_3$).

Elemental analysis: Calculated for $C_{22}H_{41}NO_4$: C, 68.89%; H, 10.77%; N, 3.65%. Found C, 68.87%; H, 10.75%; N, 3.72%.

PREPARATION 6

(2RS)-1-O-Hexadecyl-2-O-(5-phenyl-3-isoxazolyl)-glycerol

6(a) A benzene solution containing 2.16 ml of methanesulfonyl chloride was added dropwise, whilst ice-cooling, to a solution of 13.00 g of (2RS)-1-O-hexadecyl-3-O-triphenylmethylglycerol and 4.54 ml of triethylamine in 200 ml of benzene. The reaction mixture was stirred at room temperature for 1 hour, after which it was washed with water, dried and concentrated by evaporation under reduced pressure, to afford 13.65 g of a crude methanesulfonate.

6(b) A solution of 6.91 g of 3-hydroxy-5-phenylisoxazole in 40 ml of dimethylformamide was added dropwise to a suspension of 1.87 g of sodium hydride (as a 55% w/w dispersion in mineral oil) in 100 ml of dimethylformamide, whilst ice-cooling, and the mixture was stirred at room temperature for 1.5 hours. A solution of the whole of the crude methanesulfonate [prepared as described in step (a) above] in 60 ml of dimethylformamide was then added to the resulting mixture. The mixture was stirred on an oil bath kept at 100° C. for 64 hours. After cooling, the mixture was poured into water and then extracted twice with ethyl acetate. The combined extracts were washed with water, dried and concentrated by evaporation under reduced pressure to give 16.50 g of an oily residue, which was subjected to column chromatography through 400 g of silica gel. 7.87 g of (2RS)-1-O-hexadecyl-2-O-(5-phenyl-3-isoxazolyl)-3-O-triphenylmethylglycerol were obtained from the fractions eluted with mixtures of diethyl ether and hexane ranging from 3:100 to 1:20 by volume.

Following the procedure described in Preparation 2(c), the triphenylmethyl protecting group was removed to afford 4.529 g of the title compound as white crystals melting at 45.5°–46.5° C.

Nuclear Magnetic Resonance Spectrum (CDCl$_3$) δ ppm: 0.7–1.8 (31H, multiplet); 2.57 (1H, triplet, J=6 Hz); 3.50 (2H, triplet, J=6 Hz); 3.72 (2H, doublet, J=4.5 Hz); 3.98 (2H, doublet of triplets, J$_1$=4.5 Hz, J$_2$=6 Hz); 4.93 (1H, quintet, J=4.5 Hz); 6.20 (1H, singlet); 7.35–7.85 (5H, multiplet).

Mass spectrum (m/e): 460 (M$^+$+1).

Elemental analysis: Calculated for C$_{28}$H$_{45}$NO$_4$: C, 73.16%; H, 9.87%; N, 3.05%. Found: C, 73.06%; H, 9.54%; N, 3.04%.

PREPARATION 7

(2RS)-1-O-(2-Methoxyethoxy)methylglycerol

7(a) A solution of 9.25 g of (4RS)-2,2-dimethyl 1.3-dioxolane-4-methanol in 100 ml of tetrahydrofuran was added dropwise to a suspension of 3.36 g of sodium hydride (as a 55% w/w dispersion in mineral oil) in 300 ml of tetrahydrofuran at 20° to 24° C. over a period of 30 minutes. At the end of this time. 10.46 g of 2-methoxyethoxymethyl chloride in 50 ml of tetrahydrofuran were added dropwise to the mixture cooled on an ice bath. The reaction mixture was stirred at 0° to 2° C. for 3 hours, and then poured into water. It was then extracted twice with ethyl acetate. The combined extracts were washed with water, dried and concentrated by evaporation under reduced pressure. The residue was subjected to column chromatography through 200 g of silica gel. 12.80 g of (4RS)-2,2-dimethyl-4-(2-methoxyethoxy)methoxymethyl-1,3-dioxolane were obtained as a colorless oil from the fractions eluted with mixtures of ethyl acetate and hexane ranging from 1:5 to 1:4 by volume.

Nuclear Magnetic Resonance Spectrum (CDCl$_3$) δ ppm: 1.35 (3H, singlet); 1.40 (3H, singlet); 3.50 (3H, singlet); 3.55–4.40 (9H, multiplet); 4.75 (2H, singlet).

7(b) 12.78 g of (4RS)-2,2-dimethyl-4-(2-methoxyethoxy)methoxymethyl-1,3-dioxoane [prepared as described in step (a) above] were dissolved in a mixture of 40 ml of acetic acid and 20 ml of water, and the solution was stirred at 50° C. for 2 hours. The solvent was evaporated off under reduced pressure, and the residue was then distilled under reduced pressure to give 10.38 g of the title compound as a colorless liquid, boiling at a bath temperature of 120° C./1 mmHg (133 pa).

Nuclear Magnetic Resonance Spectrum (CDCl$_3$) δ ppm: 3.02 (2H, singlet); 3.40 (3H, singlet); 3.45–4.05 (9H, multiplet); 4.77 (2H, singlet).

Mass spectrum (m/e): 181 (M$^+$+1) and 149 (M$^+$—OCH$_3$)

Elemental analysis: Calculated for C$_7$H$_{16}$O$_5$: C, 46.66%; H, 8.95%. Found: C, 46.46%; H, 8.78%.

PREPARATION 8

3-O-(2-Methoxethoxy)methyl-sn-glycerol 9.214 g of (4S)-2,2-dimethyl-1,3-dioxolane-4-methanol {[α]$^{26}$+11.1° (c=1.72, CH$_3$OH), prepared from D-mannitol} was worked up in a similar manner to the procedure described in Preparation 7(a) to give 11.466 g of (4S)-2,2-dimethyl-4-(2-methoxyethoxy)-methyl-1,3-dioxolane boiling at a bath temperature of 80° C./4 mmHg (532 pa).

[α]$^{25}$+13.8° (c=1.05,CHCl$_3$).

Elemental analysis: Calculated for C$_{10}$H$_{20}$O$_5$: C, 54.53%; H, 9.15%. Found: C, 54.24%; H, 9.19%.

Following a similar procedure to that described in Preparation 7(b), 6.480 g of the compound described above was converted to the title compound (5.157 g). boiling at a bath temperature of 120°–130° C./1 mmHg (133 pa.

[α]$^{27}$—2.42° (c=1.65, CHCl$_3$).

Elemental analysis: Calculated for C$_7$H$_{16}$O$_5$: C, 46.66%; H, 8.95%. Found: C, 46.64%; H, 9.14%.

PREPARATION 9

(2RS)-1-O-Triphenylmethyl-3-O-(2-methoxyethoxy)-methylglycerol

A solution of 0.506 g of (2RS)-1-O-(2-methoxyethoxy)methylglycerol (prepared as described in Preparation 7), 0.939 g of triphenylmethyl chloride and 0.94 ml of triethylamine in 10 ml of toluene was heated under reflux for 1.5 hours. The mixture was allowed to cool and poured into a saturated aqueous solution of sodium bicarbonate. The organic layer was separated and the aqueous layer was extracted with ethyl acetate. The extract combined with the organic layer was washed with water, dried and concentrated by evaporation under reduced pressure. The residue was subjected to column chromatography through 25 g of silica gel. 0.818 g of the title compound was isolated as a colorless oil from the fractions eluted with mixtures of diethyl ether and hexane ranging from 1:3 to 1:2 by volume.

Nuclear Magnetic Resonance Spectrum (CDCl$_3$) δ ppm: 2.75 (1H, multiplet); 3.15 (2H, doublet, J=5.5 Hz); 3.32 (3H, singlet); 3 20–3.75 (6H, multiplet); 3.90 (1H, multiplet); 4.65 (2H, singlet); 7.0–7.5 (15H, multiplet).

PREPARATION 10

(2RS)-1-O-Triphenylmethyl-2-O-(3-isoxazolyl)-3-O-(2-methoxyethoxy)methylglycerol 1.9 ml of methanesulfonyl chloride was added dropwise to a solution of 8.68 g of (2RS)-1-O-triphenylmethyl-3-O-(2-methoxyethoxy)methylglycerol (prepared as described in Preparation 9) and 4.0 ml of triethylamine in 170 ml of benzene, whilst ice-cooling. The reaction mixture was then stirred at room temperature for 1 hour, after which it was washed with water, dried and concentrated by evaporation under reduced pressure. A solution of the resulting crude methanesulfonate in 40 ml of dimethylformamide was added to a solution of 3.50 g of the sodium salt of 3-hydroxyisoxazole (prepared according to the procedure described in Preparation 2) in 40 ml of dimethylformamide. The mixture was then stirred on an oil bath kept at 100° C. for 16.5 hours. After the mixture had cooled, it was poured into water and then extracted twice with ethyl acetate. The combined extracts were washed with water, dried and concentrated by evaporation under reduced pressure. The residue was subjected to column chromatography through 230g of silica gel. 6.38 g of the title compound were isolated as an oil from the fractions eluted with mixtures of ethyl acetate and hexane ranging from 1:4 to 1:3 by volume.

Nuclear Magnetic Resonance Spectrum (CDCl$_3$) $\delta$ ppm: 3.30 (3H, singlet); 3.3–3.7 (6H, multiplet); 3.86 (2H, doublet, J=b 5 Hz); 4.62 (2H, singlet); 4.96 (1H, multiplet); 5.90 (1H, doublet, J=2 Hz); 7.0–7.5 (15H, multiplet); 8.00 (1H, doublet, J=2 Hz).

PREPARATION 11

(2RS)-1-O-(2-Methoxyethoxy)methyl-2-O-(3-isoxazolyl)-glycerol 6.236 g of (2RS)-1-O-triphenylmethyl-2-O-(3-isoxazolyl)-3-O-(2-methoxyethoxy)methylglycerol (prepared as described in Preparation 10) and 0.727 g of p-toluenesulfonic acid were dissolved in 150 ml of 95% v/v aqueous methanol, and the mixture was heated under reflux for 1 hour. The mixture was allowed to cool, 100 ml of a saturated aqueous solution of sodium bicarbonate was added to the mixture, and then the methanol of the solvent was removed by evaporation under reduced pressure. The residual liquid was extracted twice with ethyl acetate, and the combined extracts were washed with water, dried and concentrated by evaporation under reduced pressure. The residue was subjected to column chromatography through 130 g of silica gel. 2.560 g of the title compound were obtained as a colorless liquid from fractions eluted with ethyl acetate. It boiled at a bath temperature of 130°–140° C./2 mmHg (267 pa).

Nuclear Magnetic Resonance Spectrum (CDCl$_3$) $\delta$ ppm: 2.71 (1H, triplet, J=7.5 Hz); 3 40 (3H, singlet): 3.45–3.85 (4H, multiplet); 3.85–4.0 (2H, multiplet); 3.93 (2H, doublet, J=5.5 Hz); 4.77 (2H, singlet); 4.90 (1H, quintet, J=5.5 Hz); 6.01 (1H, doublet, J=2 Hz); 8.13 (1H, doublet, J2 Hz).

Mass spectrum (m/e): 248 (M$^+$+1) and 172 (M$^+$–C$_3$H$_7$O$_2$).

Elemental analysis: Calculated for C$_{10}$H$_{17}$NO$_6$: C, 48.58%; H, 6.93%; N, 5.67%. Found: C, 48.66%; H, 6.74%; N, 5.66%.

PREPARATION 12

(2RS)-1-O-(N-Heptadecylcarbamoyl)-2-O-(3-isoxazolyl)-3-O-(2-methoxethoxy)methylglycerol A solution of 5.54 g of stearic acid, 3.50 ml of diphenylphosphoryl azide and 2.26 ml of triethylamine in 200 ml of benzene was heated under reflux for 3 hours. At the end of this time, the reaction mixture was cooled and then washed, in turn, with a saturated aqueous solution of sodium bicarbonate and with water. It was then dried and evaporated to dryness under reduced pressure. The residue was dissolved in 160 ml of benzene and 2.007 g of (2RS)-1-O-(2-methoxyethoxy)-methyl-2-O-(3-isoxazolyl)glycerol (prepared as described in Preparation 11) were added to the solution. The resulting mixture was then heated under reflux for 40 hours. At the end of time, the mixture was cooled and then concentrated by evaporation under reduced pressure. The residue was subjected to column chromatography through 160 g of silica gel. 3.831 g of the title compound were isolated as a colorless oil from the fractions eluted with mixtures of ethyl acetate and hexane ranging from 1:4 to 1:3 by volume.

Nuclear Magnetic Resonance Spectrum (CDCl$_3$) $\delta$ ppm: 0.7–1.7 (33H, multiplet); 3.15 (2H, doublet of triplets, J$_1$=J$_2$=6 Hz); 3.38 (3H, singlet); 3.45–3.80 (4H, multiplet); 3.87 (2H, doublet, J=4.5 Hz); 4.15–4.60 (2H, multiplet); 4.65–4.95 (1H, multiplet); 4.76 (2H, singlet); 5.10 (1H, multiplet); 6.00 (1H, doublet, J=2 Hz); 8.13 (1H, doublet J=2 Hz).

Mass spectrum (m/e): 528 (M$^+$).

PREPARATION 13

(2RS)-1-O-(N-Heptadecylcarbamoyl)-2-O-(3-isoxazolyl)glycerol

A solution of 3.747 g of (2RS)-1-O-(N-heptadecylcarbamoyl)-2-O-(3-isoxazolyl)-3-O-(2-methoxyethoxy)methylglycerol (prepared as described in Preparation 12) in 70 ml of methanol was mixed with 17.5 ml of concentrated hydrochloric acid, and the mixture was heated on an oil bath kept at 50° C. for 1.5 hours. At the end of this time, the reaction mixture was allowed to cool. The mixture was then poured into water and extracted twice with ethyl acetate. The combined extracts were washed with an aqueous solution of sodium bicarbonate and with water, dried and concentrated by evaporation under reduced pressure. The residue was recrystallized from diethyl ether, to afford 3.153 g of the title compound as white crystals melting at 71°–72° C.

Nuclear Magnetic Resonance Spectrum (CDCl$_3$) $\delta$ ppm: 0.7–1.8 (33H, multiple); 2.90 (1H, multiplet); 3.17 (2H, doublet of triplets, J$_1$=J$_2$=6 Hz); 3.87 (2H, multiplet); 4.47 (2H, doublet. J=4.5 Hz); 4.6–5.1 (2H, multiplet); 6.00 (1H, doublet, J=2 Hz); 8.13 (1H, doublet, J=2 Hz).

Infrared Absorption Spectrum $\nu_{max}$cm$^{-1}$: 3460 (—OH) and 1720 (—O—CO—NH—).

Mass spectrum (m/e): 440 (M$^+$) and 356 (M$^-$–C$_3$H$_2$NO$_2$).

Elemental analysis: Calculated for C$_{24}$H$_{44}$N$_2$O$_5$: C, 65.42%; H, 10.07%; N, 6.36%. Found: C, 65.48%; H, 10.04%; N, 6.44%.

PREPARATION 14

[(4R)-2,2-Dimethl-1,3-dioxolan-4-yl]methyl N-heptadecylcarbamate

A solution of 30.30 g of stearic acid, 22.9 ml of diphenylphosphoryl azide and 14.9 ml of triethylamine dissolved in 550 ml of benzene was heated under reflux for 3 hours. After cooling, the mixture was washed, in turn, with a saturated aqueous solution of sodium bicarbonate and water, dried and concentrated by evaporation under reduced pressure. The residue (29.62 g), (4S)-2,2-dimethyl-1,3-dioxolane-4-methanol {$[\alpha]^{26}+11.1°$ (C=1.72, CH$_3$OH)} (5.630 g), and 1.041 g of 4-(N,N-dimethylamino)pyridine were dissolved in 330 ml of toluene. The solution was heated on an oil bath kept at 100° for 20 hours, and then the solvent was removed by evaporation under reduced pressure. The residue was subjected to column chromatography through 400 g of silica gel, and 14.26 g of the title compound were obtained from the fractions eluted with mixtures of hexane and ethyl acetate ranging from 9:1 to 17:3 by volume, as crystals melting at 71°-73° C. (from hexane).

$[\alpha]^{26}-5.77°$ (c=1.04, CHCl$_3$)

Nuclear Magnetic Resonance Spectrum (CDCl$_3$) δ ppm: 0.7-1.8 (33H, multiplet); 1.37 (3H, singlet); 1.43 (3H, singlet); 3.17 (2H, triplet of doublets, J$_1$=J$_2$=6 Hz); 3.70 (1H, doublet of doublets, J$_1$=8 Hz, J$_2$=6 Hz); 3.9-4.5 (4H, multiplet); 4.73 (1H, multiplet).

Infrared Absorption Spectrum $\nu_{max}$cm$^{-1}$: 3480 and 1725.

Mass Spectrum (m/e): 398 (M$^+$ −CH$_3$).

Elemental analysis: Calculated for C$_{24}$H$_{47}$NO$_4$: C, 69.69%; H, 11.45%; N, 3.39%. Found: C, 69.58%; H, 11.44%; N, 3.47%.

PREPARATION 15

3-O-(N-Heptadecylcarbamoyl)-sn-glycerol

To a solution of 14.13 g of [(4R)-2,2-dimethyl-1,3-dioxolan-4-yl]methyl N-heptadecylcarbamate (prepared as described in Preparation 14) dissolved in 270 ml of acetic acid was added 30 ml of water, and the mixture was stirred at room temperature for 24 hours. The reaction mixture was then poured into ice-water (about 1 liter) and the precipitated solid was collected by filtration. It was washed with water and dried to afford 12.19 g of the title compound melting at 100°-102° C. (from ethyl acetate).

Infrared Absorption Spectrum (KBr) $\nu_{max}$cm$^{-1}$: 3350 and 1685.

Mass Spectrum (m/e): 373 (M$^+$), 342 and 313.

Elemental analysis: Calculated for C$_{21}$H$_{43}$NO$_4$: C, 67.52%; H, 11.60%; N, 3.75%. Found: C, 67.06%; H, 11.55%; N, 3.89%.

PREPARATION 16

3-O-(N-Heptadecylcarbamoyl)-1-O-triphenylmethyl-sn-glycerol

A solution of 12.03 g of 3-O-(N-heptadecylcarbamoyl)-sn-glycerol (prepared as described in Preparation 15), 10.77 g of triphenylmethyl chloride and 10.8 ml of triethylamine dissolved in 240 ml of toluene was heated under reflux for 1.5 hours. After cooling, the reaction mixture was poured into water (0.5 liter) and then extracted twice with ethyl acetate. The combined extracts were washed with water, dried and concentrated by evaporation under reduced pressure. The resulting residue was dissolved in 240 ml of tetrahydrofuran. To the resulting solution was added 120 ml of a saturated aqueous solution of sodium bicarbonate, and the mixture was stirred at room temperature for 1 hour. After pouring the reaction mixture into water followed by extracting twice with ethyl acetate, the combined extracts were washed with water, dried and concentrated by evaporation under reduced pressure. The residue was subjected to column chromatography through 400 g of silica gel and to medium pressure liquid chromatography using an NQ-3 Packed Column (Wako pure Chemical Industry Co.). 15.89 g of the title compound were obtained from the fractions eluted with mixtures of hexane and diethyl ether ranging from 3:2 to 2:3 by volume as a viscous liquid.

$[\alpha]^{26}-3.96°$ (c=1.01, CHCl$_3$).

Nuclear Magnetic Resonance Spectrum (CDCl$_3$) δ ppm: 0 7-1.8 (33H, multiplet); 2.77 (1H, multiplet); 3.10 (2H, multiplet); 3.20 (2H, doublet, J=5 Hz); 4.00 (1H, multiplet); 4.20 (2H, doublet J=4.5 Hz); 4.67 (1H, multiplet).

Mass Spectrum (m/e): 372 [M$^+$ −C(C$_6$H$_5$)$_3$] and 356.

Elemental analysis: Calculated for C$_{40}$H$_{57}$NO$_4$: C, 78.01%; H, 9.33%; N. 2.27%. Found: C, 78.36%; H, 9.53%; N, 2.10%.

PREPARATION 17

1-O-(N-Heptadecylcarbamoyl)-2-O-(3-isoxazolyl)-3-O-triphenylmethyl-sn-glycerol

To a solution of 12.74 g of the compound described in Preparation 16, 2.11 g of 3-hydroxyisoxazole and 10.85 g of triphenylphosphine dissolved in 230 ml of tetrahydrofuran was added all at once a solution of 6.04 g of dimethyl azodicarboxylate dissolved in 20 ml of tetrahydrofuran at room temperature. After the mixture had been stirred at room temperature for 1.5 hours, it was poured into a saturated aqueous solution (about 0.5 liter) of sodium bicarbonate, and was then extracted twice with ethyl acetate. The combined extracts were washed with water, dried and concentrated by evaporation under reduced pressure and the resulting residue was subjected to column chromatography through 280 g of silica gel and to medium pressure liquid chromatography using a Lobar C Column (Merck Co.). The title compound (11.13 g) was obtained from the fractions eluted with a 4:1 by volume mixture of hexane and diethyl ether, as a viscous liquid.

$[\alpha]^{26}+14.8°$ (c=1.05, CHCl$_3$).

Nuclear Magnetic Resonance Spectrum (CDCl$_3$) δ ppm: 0.75-1 75 (33H, multiplet); 3.10 (2H, multiplet) 3.32 (1H, dd, J$_1$=10.5, J$_2$=4.5 Hz); 3.51 (1H, dd, J$_1$=10.5, J$_2$=4.5 Hz); 4.44 (2H, doublet J=b 4.5 Hz); 4.53 (1H, multiplet); 5.08 (1H, quintet, J=4.5 Hz); 6.00 (1H, doublet, J=2 Hz); 7.1-7.8 (15H, multiplet); 8.15 (1H, doublet, J=2 Hz).

Mass Spectrum (m/e): 423 [M$^+$ −OC(C$_6$H$_5$)$_3$].

Elemental analysis: Calculated for C$_{43}$H$_{58}$N$_2$O$_5$: C, 75.62%; H, 8.56%; N, 4.10%. Found: C, 75.51%; H, 8.47%; N, 4.22%.

PREPARATION 18

1-O-(N-Heptadecylcarbamoyl)-2-O-(3-isoxazolyl)-sn-glycerol

Following a similar procedure to that described in the latter half of Preparation 3(b), the triphenylmethyl group was removed from 11.00 g of 1-O-(N-heptadecylcarbamoyl)- 2-O-(3-isoxazolyl)-3-O-triphenylmethylsn-glycerol (prepared as described in Preparation 17), to give 6.87 g of the title compound as white crystals melting at 89°–91° C. (from hexane).

$[\alpha]^{26} -13.04°$ (c=1.02, CHCl$_3$).

The spectra of this compound were identical with those of the compound described in Preparation 13.

Elemental analysis: Calculated for C$_{24}$H$_{44}$N$_2$O$_5$: C, 65.42%; H, 10.07%; N, 6.36%. Found: C, 65.14%; H, 10.07%; N, 6.34%.

PREPARATION 19

Diethyl 2-(5-methyl-3-isoxazolyloxy)malonate

A solution of 3.468 g of 3-hydroxy-5-methylisoxazole in 35 ml of hexamethylphosphoric triamide was added dropwise to a suspension of 1.527 g of sodium hydride (as a 55% w/w dispersion in mineral oil) in 20 ml of hexamethylphosphoric triamide, whilst ice-cooling. The mixture was then stirred at room temperature for an hour. A solution of 8.367 g of diethyl 2-bromomalonate in 35 ml of hexamethylphosphoric triamide was then added dropwise to the mixture, whilst cooling it with ice-water. The mixture was stirred at room temperature for 1 hour and then poured into ice-water. It was then extracted twice with ethyl acetate. The combined extracts were washed with water, dried and concentrated by evaporation under reduced pressure. The residue was subjected to column chromatography through 200 g of silica gel. 7.593 g of the title compound were isolated as an oily material from the fractions eluted with mixtures of ethyl acetate and hexane ranging from 1:10 to 15:100 by volume.

Nuclear Magnetic Resonance Spectrum (CDCl$_3$) δ ppm: 1.30 (6H, triplet, J=7 Hz); 2.32 (3H, singlet); 4.31 (4H, quartet, J=7 Hz); 5.57 (1H, singlet); 5.80 (1H, singlet).

Mass spectrum (m/e): 257 (M$^+$) and 212 (M$^+$–OC$_2$H$_5$).

Elemental analysis: Calculated for C$_{11}$N$_{15}$NO$_6$: C, 51.36%; H, 5.88%; N, 5.44%. Found: C, 51.38%; H, 5.92%; N, 5.36%.

PREPARATION 20

2-O-(5-Methyl-3-isoxazolyl)glycerol

A solution of 23.72 g of diethyl 2-(5-methyl-3-isoxazolyloxy)malonate (prepared as described in Preparation 19) in 120 ml of tetrahydrofuran was added dropwise to a suspension of 14.00 g of lithium aluminum hydride in 140 ml of tetrahydrofuran over a period of 30 minutes, whilst ice-cooling. The mixture was stirred at room temperature for 40 hours, after which 56 ml of a 4% w/v aqueous solution of sodium hydroxide was added dropwise to it over a period of 30 minutes, whilst ice-cooling. An insoluble material was filtered off using a Celite (trade mark) filter aid, and the filtrate was concentrated by evaporation under reduced pressure. The residue was subjected to column chromatography through 300 g of silica gel. 11.26 g of the title compound was isolated as a colorless oil from the fractions eluted with ethyl acetate.

Nuclear Magnetic Resonance Spectrum (CDCl$_3$) δ ppm: 2.31 (3H, singlet); 3.47 (2H, multiplet); 3.90 (4H, multiplet); 4.70 (1H, quintet, J=4.5 Hz); 5.70 (1H, singlet).

Mass spectrum (m/e): 174 (M$^+$+1) and 156 (M$^+$–H$_2$O).

PREPARATION 21

(2RS)-1-O-(N-Heptadecylcarbamoyl)-2-O-(5-methyl-3-isoxazolyl)glycerol

A mixture of 2.96 g of stearic acid, 1.87 ml of diphenylphosphoryl azide and 1.21 ml of triethylamine in 90 ml of benzene was heated under reflux for 16 hours. At the end of this time, the mixture was cooled and washed, in turn, with a saturated aqueous solution of sodium bicarbonate and with water. The mixture was then dried, and the solvent was evaporated off under reduced pressure, to give 2.40 g of crude heptadecyl isocyanate.

1.95 g of this crude heptadecyl isocyanate, 1.00 g of 2-O-(5-methyl-3-isoxazolyl)glycerol (prepared as described in Preparation 20) and 1.13 ml of triethylamine were dissolved in 40 ml of benzene. The solution was heated under reflux for 15 hours and cooled. The solvent was then evaporated off under reduced pressure. The residue was subjected to column chromatography through 60 g of silica gel. 1.984 g of the title compound was obtained as white crystals from the fractions eluted with mixtures of ethyl acetate and hexane ranging from 1:4 to 1:1 by volume. It melted at 77°–79° C. (on recrystallization from diethyl ether).

Nuclear Magnetic Resonance Spectrum (CDCl$_3$) δ ppm: 0.8–1.7 (33H, multiplet); 2.33 (3H, singlet); 2.97 (1H, triplet, J=6 Hz); 3.17 (2H, doublet of triplets, J$_1$=J$_2$=7 Hz); 3.83 (2H, doublet of doublets, J$_1$=6 Hz, J$_2$=5 Hz); 4.43 (2H, doublet, J=5 Hz); 4.6–5.1 (1H, multiplet); 4.87 (1H, quintet, J=5 Hz); 5.67 (1H, singlet).

Infrared Absorption Spectrum $\nu_{max}$cm$^{-1}$: 3460 (—NH, —OH) and 1720 (—O—CO—N).

Mass spectrum (m/e): 454 (M$^+$) and 356 (M$^+$–C$_3$H$_4$NO$_2$).

Elemental analysis: Calculated for C$_{25}$H$_{46}$N$_2$O$_5$: C, 66.05%; H, 10.20%; N, 6.16%. Found: C, 66.30%; H, 10.17%; N, 6.27%.

PREPARATION 22

Diethyl 2-(5-phenyl-3-isoxazolyloxy)malonate 5.629 g of 3-hydroxy-5-phenylisoxazole were terated in a similar manner to that described in Preparation 19, to give 9.923 g of the title compound as white crystals melting at 62°–64° C. (from a mixture of diethyl ether and hexane).

Magnetic Resonance Spectrum (CDCl$_3$) δ ppm: 1.33 (6H, triplet, J=7 Hz); 4.35 (4H, quartet, J=7 Hz); 5.65 (1H, singlet); 6.33 (1H, singlet); 7.35–7.85 (5H, multiplet).

Mass spectrum (m/e): 319 (M$^+$) and 274 (M$^+$–OCH$_2$CH$_3$).

Elemental analysis: Calculated for C$_{16}$H$_{17}$NO$_6$: C, 60.18%; H, 5.37%; N, 4.39%. Found: C, 60.12%; H, 5.30%; N, 4.36%.

PREPARATION 23

2-O-(5-Phenyl-3-isoxazolyl)glycerol

A solution of 9.118 g of diethyl 2-(5-phenyl-3-isoxazolyloxy)malonate (prepared as described in Preparation 22) in 50 ml of tetrahydrofuran wa added dropwise to a suspension of 4.33 g of lithium aluminum hydride in 50 ml of tetrahydrofuran, whilst ice-cooling. The reaction mixture was then heated under reflux for 5 hours, after which it was worked-up in a similar manner to that described in Preparation 20, to afford 4.394 g if the title compound as white crystals, melting at 117°–119° C. (from a mixture of methanol and methylene chloride).

Nuclear Magnetic Resonance Spectrum (CD$_3$OD) δ ppm: 3.87 (4H, doublet, J=5 Hz); 4.60–4.90 (1H, multiplet); 6.43 (1H, singlet); 7.4–7.9 (5H, multiplet).

Mass spectrum (m/e): 236 (M$^+$ +1) and 235 (M$^+$).

Elemental analysis: Calculated for C$_{12}$H$_{13}$NO$_4$: C, 61.27%; H, 5.57%; N, 5.95%. Found: C, 61.13%; H, 5.46%; N, 5.95%.

PREPARATION 24

(2RS)-1-O-(N-Heptadecylcarbamoyl)-2-O-(5-phenyl-3-isoxazolyl)glycerol 1.580 g of the title compound was prepared from 0.800 g of 2-O-(5-phenyl-3-isoxazolyl)glycerol (prepared as described in Preparation 23), following the procedure described in Preparation 21. It was in the form of white crystals melting at 72°–74° C. (from diethyl ether).

Nuclear Magnetic Resonance Spectrum (CDCl$_3$) δ ppm: 8–1.7 (33H, multiplet); 2.97 (1H, triplet, J=7 Hz); 3.17 (2H, doublet of triplets, J$_1$=J$_2$=6 Hz); 3.89 (2H, doublet of doublets, J$_1$=7 Hz, J$_2$=4.5 Hz); 4.49 (2H, doublet, J=4.5 Hz); 4.87 (1H, multiplet); 4.98 (1H, quintet, J=4.5 Hz); 6.19 (1H, singlet); 7.35–7.90 (5H, multiplet).

Mass spectrum (m/e): 516 (M$^+$) and 356 (M$^+$-C$_9$H$_6$NO$_2$).

Elemental analysis: Calculated for C$_{30}$H$_{48}$N$_2$O$_5$: C, 69.73%; H, 9.36%; N, 5.42%. Found: C, 69.80%; H, 9.47%; N, 5.52%.

PREPARATION 25

Ethyl 3-oxostearate 502 ml of a 15.12% by weight solution of butyllithium in hexane was added dropwise at −78° C. over a period of 30 minutes to a solution of 128 ml of cyclohexylisopropylamine in 800 ml of tetrahydrofuran. After the addition was complete, the reaction mixture was allowed to warm up to 0° C. over a period of 30 minutes. It was then again cooled to −78° C., after which 38 ml of ethyl acetate were added over a period of 5 minutes. The mixture was then stirred at the same temperature for 10 minutes, after which 75.0 g of palmitoyl chloride were added dropwise to it over a period of 5 minutes. The mixture was then stirred at −78° C. for 10 minutes, after which 250 ml of 20% v/v aqueous hydrochloric acid was added dropwise to the reaction mixture. The reaction mixture was then allowed to warm to room temperature, and 1 liter of diethyl ether was added. The resulting two layers were separated, and the aqueous layer was extracted with diethyl ether. The organic layer was combined with the extract, and this was washed, in turn, with a saturated aqueous solution of sodium bicarbonate and with an aqueous solution of sodium chloride. It was then dried and concentrated by evaporation under reduced pressure. The residue was allowed to stand to produce crystals, which were collected by filtration, to give 55.61 g of the title compound. Recrystallization of the product from cold ethanol gave white prisms melting at 38°–39° C.

Nuclear Magnetic Resonance Spectrum (CDCl$_3$) δ ppm: 0.7–1.8 (32H, multiplet); 2.53 (2H, triplet, J=7.5 Hz); 3.42 (2H, singlet); 8.21 (2H, quartet, J=7.5 Hz).

Infrared Absorption Spectrum $\nu_{max}$cm$^{-1}$: 1740 (—CO—O—) and 1715 (—CO—).

Mass spectrum (m/e): 326 (M$^+$) and 308 (M$^+$- H$_2$O).

Elemental analysis: Calculated for C$_{20}$H$_{38}$O$_3$: C, 73.57%; H, 11.73%. Found: C, 73.90%; H, 11.76%.

PREPARATION 26

3-Hydroxy-5-pentadecylisoxazole

26(a) A solution of 42.57 g of ethyl 3-oxostearate (prepared as described in Preparation 25). 9.71 g of ethylene glycol and 1 g of camphorsulfonic acid in 200 ml of toluene was heated under reflux for 24 hours, and the water produced was removed through a side arm attached to a water separator. The mixture was allowed to cool, and then washed, in turn, with a saturated aqueous solution of sodium bicarbonate and with water. It was then dried and concentrated by evaporation under reduced pressure, to give 29.66 g of crude ethyl 3,3-ethylenedioxystearate.

11.12 g of hydroxylamine hydrochloride were added to a solution of 12.60 g of sodium hydroxide in a mixture of 80 ml of water and 100 ml of ethanol, whilst ice-cooling. A solution of the whole of the crude ethyl 3,3-ethylenedioxystearate prepared as described above in 200 ml of ethanol was added all at once, whilst ice-cooling, to the resulting mixture. The reaction mixture was then stirred at room temperature for 2 hours. At the end of this time, 100 ml of concentrated hydrochloric acid were added, and the mixture was heated under reflux for 1.5 hours. The mixture was allowed to cool, and the precipitated solid was collected by filtration and dissolved in methylene chloride. The methylene chloride solution was washed with a saturated aqueous solution of sodium bicarbonate and with water, dried and concentrated by evaporation under reduced pressure. The residue was filtered with the aid of suction to give 7.19 g of the title compound as crystals. An oily material (19 g) separated from the filtration was subjected to column chromatography through 250 g of alumina (grade III). From the fractions eluted with a 20:1 by volume mixture of methanol and acetic acid, an additional 0.82 g of crystals was obtained. These crystals melted at 81.5°–82.5° C. (from cold methylene chloride).

Nuclear Magnetic Resonance Spectrum (CDCl$_3$) δ ppm: 0.7–1.9 (29H); 2.63 (2H, triplet, J=7 Hz); 5.67 (1H, singlet); 11.13 (1H, singlet).

Mass spectrum (m/e): 295 (M$^+$).

Elemental analysis: Calculated for C$_{18}$H$_{33}$NO$_2$: C, 73.17%; H, 11.26%; N, 4.70%. Found: C, 72.99%; H, 11.15%; N, 4.70%

26(b) 69.1 ml of a 15.13% w/w hexane solution of butyllithium was added dropwise to a solution of 15.42 ml of diisopropylamine in 500 ml of tetrahydrofuran at −10° to −15° C., and the mixture was stirred at the same temperature for 15 minutes. To it was added dropwise a solution of 4.95 g of 3-hydroxy-5-methylisoxazole dissolved in 50 ml of tetrahydrofuran at −10° C., and the mixture was stirred at the same temperature for 30 minutes. It was then cooled to −55° C. after which 41.6 g of tetradecyl bromide were added all at once. After removal from the cooling bath, the mixture was stirred for 3 hours, and then 100 ml of diethyl ether were added. The mixture was washed with 150 ml of 5% w/v aqueous hydrochloric acid, and the organic layer was washed with water, dried and concentrated by evaporation under reduced pressure. 100 ml of hexane were added to the residue, and the precipitated solid was collected by filtration and washed with hexane. It was then dried to give crude crystals (13.65 g) of the title compound. Concentration of the filtered hexane solution gave a residue, which was subjected to column chromatography through 100 g of silica gel. Crude crystals (1.40 g) were obtained from the fractions eluted with a 2:1 by volume mixture of methylene chloride and diethyl ether. The combined crude crystals were recrystallized from methylene chloride to give the pure title compound (9.65 g) melting at 82°-83° C. Further crystals (3.91 g) were obtained by concentration of the mother liquor. The spectra of these compounds were identical with those of the compound obtained as described in (a) above.

Elemental analysis: Calculated for $C_{18}H_{33}NO_2$: C, 73.17%; H, 11.26%; N, 4.74%. Found: C, 73.26%; H, 11.21%; N, 4.73%.

PREPARATION 27

(2RS)-1-O-(5-pentadecyl-3-isoxazolyl)glycerol

A suspension of 2.000 g of 3-hydroxy-5-pentadecylisoxazole (prepared as described in Preparation 26) and 0.30 g of sodium hydride (as a 55% w/w dispersion in mineral oil) in 20 ml of dimethylformamide was heated at 50° C. for 1 hour.

Meanwhile, 1.18 ml of methanesulfonyl chloride was added to a solution of 1.342 g of 2,2-dimethyl-1,3-dioxolane-4-methanol and 2.83 ml of triethylemine in benzene, whilst ice-cooling, and the mixture was stirred at room temperature for 1 hour. The mixture was washed with water, dried and concentrated by evaporation under reduced pressure, to give 1.708 g of a crude mesylate.

A solution of this crude mesylate in 10 ml of dimethylformamide was then added to the suspension prepared as described above, and the mixture was stirred on an oil bath kept at 100° C. for 18 hours. After it had been allowed to cool, the mixture was poured into water and extracted twice with ethyl acetate. The combined extracts were washed with water, dried and concentrated by evaporation under reduced pressure. The residue was subjected to column chromatography through 70 g of silica gel. 1.862 g of RS-3-(2,2-dimethyl-1,3-dioxolan-4-yl)methoxy-5-pentadecylisoxazole was isolated from the fractions eluted with a 1:20 by volume mixture of ethyl acetate and hexane. The whole of this compound was dissolved in a mixture of 12 ml of acetic acid and 6 ml of water, and the solution was heated at 60° C. for 3 hours. The reaction mixture was then poured into water and extracted with ethyl acetate. The extract was washed with water, dried and concentrated by evaporation under reduced pressure to give a residue, recrystallization of which from diethyl ether afforded 1.270 g of the title compound, melting at 84°-85° C.

Nuclear Magnetic Resonance Spectrum (CDCl$_3$) δ ppm: 0.7-1.9 (29H, multiplet); 2.57 (1H, triplet, J=5 Hz); 2.63 (2H, triplet); 3.03 (1H, doublet, J=5 Hz); 3.70 (2H, doublet of doublets, J$_1$=J$_2$=5 Hz); 4.05 (1H, multiplet); 4.33 (2H, doublet, J=5 Hz); 5.63 (1H, singlet).

Mass spectrum (m/e): 369 (M$^+$) and 338 (M$^+$-CH$_2$OH).

Elemental analysis: Calculated for $C_{21}H_{39}NO_4$: C, 68.25%; H, 10.64%; N, 3.79%. Found: C, 68.05%; H, 10.77%; N, 3.73%.

PREPARATION 28

(2RS)-1-O-(5-pentadecyl-3-isoxazolyl)-3-O-triphenylmethylglycerol

A solution of 1.200 g of (2RS)-1-O-(5-pentadecyl-3-isoxazolyl)glycerol (prepared as described in Preparation 27), 1.086 g of triphenylmethylchloride and 1.09 ml of triethylamine in 25 ml of toluene was heated under reflux for 2 hours. After the toluene had been distilled away, the residue was mixed with 30 ml of tetrahydrofuran and a saturated aqueous solution of sodium bicarbonate, and the mixture was stirred at room temperature for 1 hour. The reaction mixture was then poured into water and extracted twice with ethyl acetate. The combined extracts were washed with water, dried and concentrated by evaporation under reduced pressure. The residue was subjected to column chromatography through 50 g of silica gel. 1.571 g of of the title compound was isolated as an oil from the fractions eluted with a 1:3 by volume mixture of diethyl ether and hexane.

Nuclear Magnetic Resonance Spectrum (CDCl$_3$) δ ppm: 0.7-1.9 (29H, multiplet); 2.57 (1H, doublet, J=4.5 Hz); 2.61 (2H, triplet, J=7 Hz); 3.29 (2H, doublet. J=5 Hz); 4.10 (1H, multiplet); 4.35 (2H, doublet. J=5 Hz); 5.60 (1H, singlet); 7.1-7.7 (15H, multiplet).

Mass spectrum (m/e): 611 (M$^-$) and 534 (M$^+$- C$_6$H$_5$).

Elemental analysis: Calculated for $C_{40}H_{53}NO_4$: C, 78.52%; H, 8.73%; N, 2.29%. Found: C, 78.67%; H, 8.86%; N, 2.12%.

PREPARATION 29

(2RS)-1-O-(5-pentadecyl-3-isoxazolyl)-2-O-methylglycerol

A mixture of 0.117 g of sodium hydride (as a 55% w/W dispersion in mineral oil), 1.094 g of (2RS)-1-O-(5-pentadecyl-3-isoxazolyl)-3-O-triphenylmethylglycerol (prepared as described in Preparation 28) and 10 ml of dimethylformamide was stirred at room temperature for 1 hour. At the end of this time. 0.45 ml of methyl iodide was added to the mixture, which was then stirred for a further 3 hours. The reaction mixture was then poured into water and extracted twice with ethyl acetate. The combined extracts were washed with water, dried and concentrated by evaporation under reduced pressure. The residue (1.18 g) was dissolved in 40 ml of 95% v/v methanol. To this solution was added 0.142 g of p-toluenesulfonic acid, and then the mixture was heated under reflux for 1 hour. After the mixture had been allowed to cool, 10 ml of a saturated aqueous solution of sodium bicarbonate were added to the mixture and the methanol of the solvent was stripped off by evaporation under reduced pressure. The residual mixture was extracted twice with ethyl acetate. The combined extracts were washed with water, dried and concentrated by evaporation under reduced pressure. The residue was subjected to column chromatography through 40 g of silica gel. 0.624 g of the title compound was obtained as crystals melting at 43°-44° C. (from cold hexane).

Nuclear Magnetic Resonance Spectrum (CDCl$_3$) δ ppm: 0.7-1.9 (29H, multiplet); 2.27 (1H, triplet, J=6 Hz); 2.62 (2H, triplet, J=7 Hz); 3.50 (3H, singlet); 3.5-3.9 (3H, multiplet); 4.35 (2H, doublet, J=4.5 Hz); 5.61 (1H, singlet).

Mass spectrum (m/e): 383 (M$^+$) and 352 (M$^+$- OCH$_3$).

Elemental analysis: Calculated for $C_{22}H_{41}NO_4$: C, 68.89%; H, 10.77%; N, 3.65%. Found: C, 68.76%; H, 10.59%; N, 3.64%.

PREPARATION 30

2-Nonadecyn-1-yl 2-tetrahydropyranyl ether 50 ml of a 15% by weight solution of butyllithium in hexane was added dropwise at −50° C. to a solution of 11.48 g of 2-tetrahydropyranyl propargyl ether in 220 ml of tetrahydrofuran followed by 25 g of palmityl bromide, and the mixture was stirred for 30 minutes, during which time the temperature of the mixture was allowed to rise to room temperature. The reaction mixture was heated under reflux for 16 hours, poured into water and then extracted twice with diethyl ether. The combined extracts were washed with water, dried and concentrated by evaporation under reduced pressure. The residue was subjected to column chromatography through 500 g of silica gel. 14.59 g of the title compound were isolated as an oil from the fractions eluted with a 3:100 by volume mixture of diethyl ether and hexane.

Nuclear Magnetic Resonance Spectrum (CDCl$_3$) δ ppm: 0.7–2.0 (37H, multiplet); 2.20 (2H, multiplet); 3.3–4.1 (2H, multiplet); 4.21 (2H, triplet, J=2.5 Hz); 4.80 (1H, multiplet).

PREPARATION 31

Ethyl 2-Nonadecynoate

A mixture of 14.0 g of 2-nonadecyn-1-yl 2-tetrahydropyranyl ether (prepared as described in Preparation 30). 80 ml of acetic acid, 80 ml of tetrahydrofuran and 40 ml of water was stirred on an oil bath kept at 50° C. for 16 hours. The mixture was cooled, and then the precipitated 2-nonadecyn-1-ol (10.33 g) was collected by filtration, washed with water and dried. 27.5 ml of Jones' reagent (0.267 g of anhydrous chromic acid per 1 ml) were added to a solution of this precipitated 2-nonadecyn-1-ol in 100 ml of acetone, and then the mixture was stirred at room temperature for 15 minutes. The reaction mixture was then poured into 500 ml of water and extracted with twice diethyl ether. The combined extracts were washed with water, dried and concentrated by evaporation under reduced pressure to give 11.14 g of a crystalline residue, which was dissolved in a mixture of 150 ml of absolute ethanol and 200 ml of benzene. The mixture was heated under reflux for 16 hours in the presence of 2 ml of concentrated sulfuric acid. The reaction mixture was cooled and poured into 500 ml of ice-water, and an organic layer was separated. The organic layer was washed with a saturated aqueous solution of sodium bicarbonate and with water, dried and concentrated by evaporation under reduced pressure. The residue was subjected to column chromatography through 60 g of silica gel. 9.49 g of the title compound were isolated as an oil from the fractions eluted with a 1:1 by volume mixture of methylene chloride and hexane.

Nuclear Magnetic Resonance Spectrum (CDCl$_3$) δ ppm: 0.7–1.8 (34H, multiplet); 2.28 (2H, broad triplet, J=6 Hz); 4.15 (2H, quartet, J=7 Hz).

PREPARATION 32

3-Hydroxy-5-hexadecylisoxazole 13.24 g of hydroxylamine hydrochloride were added to a mixture of 130 ml of a 10% w/v aqueous solution of sodium hydroxide and 100 ml of ethanol, whilst ice-cooling. A solution of 5.08 g of ethyl 2-nonadecynoate (prepared as described in Preparation 31) in ethanol (30 ml) was then added dropwise to the resulting mixture, which was then stirred at room temperature for 16 hours. The mixture was then adjusted to a pH value of 3 by adding concentrated hydrochloric acid, and then the mixture was extracted three times with diethyl ether. The combined extracts were washed with water, dried and concentrated by evaporation under reduced pressure. The residue was subjected to column chromatography through 50 g of silica gel. 4.09 g of the title compound were isolated from the fractions eluted with a 1:1 by volume mixture of methylene chloride and hexane, to give crystals melting at 85°–86° C. (from cold diethyl ether).

Nuclear Magnetic Resonance Spectrum (CDCl$_3$) δ ppm: 0.8–1.9 (31H, multiplet) 2.60 (2H, triplet, J=7 Hz); 5.65 (1H, singlet); 9.88 (1H, multiplet).

Mass spectrum (m/e): 309 (M$^+$) and 277 (M$^+$- H$_2$O).

Elemental analysis: Calculated for C$_{19}$H$_{35}$NO$_2$: C, 73.74%; H, 11.40%; N, 4.52%. Found: C, 73.48%; H, 11.44%; N, 4.58%.

PREPARATION 33

(2RS)-1-O-(5-Hexadecyl-3-isoxazolyl)-2-O-(3-isoxazolyl)glycerol

33(a) 0.81 ml of methanesulfonyl chloride were added to a solution of 1.731 g of (2RS)-1-O-(2-methoxyethoxy)methyl-2-O-(3-isoxazolyl)glycerol (prepared as described in Preparation 11) and 1.95 ml of triethylamine in 35 ml of benzene, whilst ice-cooling. The reaction mixture was then stirred at room temperature for 30 minutes, after which it was washed with water, dried and concentrated by evaporation under reduced pressure, to give a crude mesylate.

33(b) Meanwhile, a mixture of 0.339 g of sodium hydride (as a 55% w/w dispersion in mineral oil) and 2.405 g of 3-hydroxy-5-hexadecylisoxazole (prepared as described in Preparation 32) in 40 ml of dimethylformamide was heated at 50° C. for 1 hour, whilst stirring. A solution of the mesylate prepared as described in step (a) above in 10 ml of dimethylformamide was then added to the resulting mixture, and the mixture was then stirred on an oil bath kept at 100° C. for 16 hours. The reaction mixture was allowed to cool, poured into 500 ml of water and extracted three times with methylene chloride. The combined extracts were washed with water, dried and concentrated by evaporation under reduced pressure. The residue was subjected to column chromatography through 70 g of silica gel. Working-up of the fractions eluted with a 20:20:1 by volume mixture of methylene chloride, hexane and ethyl acetate yielded 2.947 g of an oily substance.

33(c) 10 ml of concentrated hydrochloric acid were added to a solution of the oil prepared as described in step (b) above in 70 ml of methanol, and then the mixture was stirred at 50° C. for 3 hours. The methanol of the solvent was then removed by evaporation under reduced pressure. The residue was diluted with 100 ml of water and extracted twice with ethyl acetate. The combined extracts were washed with water, dried and concentrated by evaporation under reduced pressure. The residue was subjected to column chromatography through 70 g of silica gel. 2.247 g of the title compound were obtained from the fractions eluted with mixtures of hexane and diethyl ether ranging from 2:1 to 1:1 by volume, as white feathery crystals melting at 54°–57° C. (from hexane).

Nuclear Magnetic Resonance Spectrum (CDCl$_3$) δ ppm: 0.7–1.9 (31H, multiplet); 2.61 (2H, triplet, J=7 Hz); 2.90 (1H, triplet, J=5 Hz); 3.96 (2H, doublet of doublets, $J_1=5$, $J_2=4.5$ Hz); 4.59 (2H, doublet, J=4.5 Hz); 5.07 (1H, quintet, J=4.5 Hz); 5.63 (1H, singlet); 6.01 (1H, doublet, J=2 Hz); 8.13 (1H, doublet, J=2 Hz).

Mass spectrum (m/e): 450 (M+) and 366 (M+-$C_3H_2NO_2$).

Elemental analysis: Calculated for $C_{25}H_{42}N_2O_5$: C, 66.63%; H, 9.39%; N, 6.22%. Found: C, 66.65%; H, 9.44%; N, 6.20%.

PREPARATION 34

(2RS)-1-O-(2-Tetrahydropyranyl)-2-O-(5-methyl-3-isoxazolyl)glycerol

A solution of 11.26 g of 2-O-(5-methyl-3-isoxazolyl)glycerol (prepared as described in Preparation 20), 5.93 ml of dihydropyran and 0.15 g of pyridine p-toluenesulfonate in 110 ml of methylene chloride was stirred at room temperature for 14 hours. The solvent was removed by evaporation under reduced pressure, and then the residue was subjected to column chromatography through 350 g of silica gel. 3.32 g of the 1,3-ditetrahydropyranyl compound was first eluted with a 1:4 by volume mixture of ethyl acetate and hexane, and then 9.67 g of the title compound were isolated as a colorless oil from the fractions eluted with a 1:1 by volume mixture of ethyl acetate and hexane.

Nuclear Magnetic Resonance Spectrum (CDCl$_3$) δ ppm: 1.3-1.9 (6H, multiplet); 2.32 (3H, singlet); 2.85 (1H, multiplet); 3 2-4.2 (6H, multiplet); 4.60 (1H, multiplet); 4.84 (1H, quintet, J=5 Hz); 5.67 (1H, singlet).

PREPARATION 35

(2RS)-1-O-(5-pentadecyl-3-isoxazolyl)-2-O-(5-methyl-3-isoxazolyl)qlycerol 3.93 g of (2RS)-1-O-(2-tetrahydropyranyl)-2-O-(5-methyl-3-isoxazolyl)glycerol (prepared as described in Preparation 34) were converted to the mesylate in a similar manner to that described in Preparation 33(a). A mixture of 0.606 g of sodium hydride (as a 55% w/w dispersion in mineral oil) and 4.10 g of 3-hydroxy-5-pentadecylisoxazole (prepared as described in Preparation 26) in 40 ml of hexamethylphosphoric triamide was stirred at 50° C. for an hour. A solution of the mesylate described above in 40 ml of hexamethylphosphoric triamide was added to the mixture, which was then stirred at 100° C. for 2 hours. The reaction mixture was allowed to cool, poured into water and extracted twice with ethyl acetate. The combined extracts were washed with water, dried and concentrated by evaporation under reduced pressure. The residue was subjected to column chromatography through 150 g of silica gel. An oily material (6.81 g), obtained from the fractions eluted with mixtures of ethyl acetate and hexane ranging from 1:20 to 1:10 by volume, was dissolved in 140 ml of 95% methanol. The solution was heated under reflux for 1 hour in the presence of 0.73 g of p-toluenesulfonic acid. 1.6 g of sodium bicarbonate were added, the methanol was removed by evaporation under reduced pressure, and the residue was mixed with ethyl acetate and then filtrated. The solvent was removed by evaporation under reduced pressure, and the resulting residue was subjected to column chromatography through 120 g of silica gel. 5 50 g of the title compound were isolated from the fractions eluted with a 1:4 by volume mixture of ethyl acetate and hexane as white crystals melting at 64°-65° C. (from hexane).

Nuclear Magnetic Resonance Spectrum (CDCl$_3$) δ ppm: 0.7-1.9 (29H, multiplet); 2.33 (3H, singlet; 2.61 (2H, triplet, J=7 Hz); 2.85 (1H, triplet, J=6 Hz); 3.95 (2H, doublet of doublets, $J_1=6$ Hz. $J_2=5$ Hz); 4.57 (2H, doublet, J=5 Hz); 5.03 (1H, quintet, J=5 Hz); 5.63 (1H, singlet); 5.69 (1H, singlet).

Mass spectrum (m/e): 450 (M+) and 352 (M+-$C_4H_4NO_2$).

Elemental analysis: Calculated for $C_{25}H_{42}N_2O_5$: C, 66.64%; H, 9.39%; N, 6.22%. Found: C, 66.49%; H, 9.19%; N, 6.21%.

PREPARATION 36

(2RS)-1-O-{7-(2-Tetrahydropyranyloxy)heptyl}-2-O-(5-methyl-3-isoxazolyl)glycerol 1.062 g of 7-(2-tetrahydropyranyloxy)heptan-1-ol were converted to the methanesulfonate in a similar manner to that described in Preparation 33(a).

0.850 g of 2-O-(5-methyl-3-isoxazolyl)glycerol (prepared as described in Preparation 20) in 5 ml of dimethylformamide was added dropwise to a suspension of 0.214 g of sodium hydride (as a 55% w/w dispersion in mineral oil) in 5 ml of dimethylformamide, and the mixture was stirred at room temperature for 1 hour. A solution of the above methanesulfonate in 10 ml of dimethylformamide was then added, whilst ice-cooling, and the mixture was stirred at room temperature for 18 hours. The reaction mixture was then poured into water and twice extracted with ethyl acetate. The combined extracts were washed with water, dried and concentrated by evaporation under reduced pressure, to give a residue, which was subjected to column chromatography using a Lobar B column. 0.820 g of the title compound was isolated as a colorless oil from the fractions eluted with a 1:2 by volume mixture of ethyl acetate and hexane.

Nuclear Magnetic Resonance Spectrum (CDCl$_3$) δ ppm: 1.15-2.00 (16H, multiplet); 2.30 (3H, singlet); 2.61 (1H, multiplet); 3.2-3.7 (4H, multiplet); 3.73 (2H, doublet, J=4.5 Hz); 3.91 (2H, doublet, J=4.5 Hz); 3.8-4.1 (2H, multiplet); 4.57 (1H, multiplet); 4.80 (1H, quintet, J4.5 Hz); 5.65 (1H, singlet).

Mass spectrum (m/e): 372 (M++1).

PREPARATION 37

(2RS)-1-O-(5-pentadecyl-3-isoxazolyl)-2-O-(5-methyl-3-isoxazolyl)-3-O-(7-hydroxyheptyl)glycerol 0.797 g of (2RS)-1-O-{7-(2-tetrahydropyranyloxy)heptyl}-2-O-(5-methyl-3-isoxazolyl)glycerol (prepared as described in Preparation 36) was converted to the methanesulfonate in a similar manner to that described in Preparation 33(a). A mixture of 0.140 g of sodium hydride (as a 55% w/w dispersion in mineral oil) and 0.951 g of 3-hydroxy-5-pentadecylisoxazole [prepared as described in Preparation 26(a)] in 10 ml of hexamethylphosphoric triamide was stirred at 50° C. for an hour, and then the resulting mixture was mixed with a solution of the above methanesulfonate in 10 ml of hexamethylphosphoric triamide. The reaction mixture was heated at 100° C. for 3 hours, and then poured into water and extracted with ethyl acetate. The combined extracts were washed with water, dried and concentrated by evaporation under reduced pressure, to give a residue, which was subjected to column chromatography using alumina (grade II to III, 65 g). An oily material (1.199 g) obtained from the fractions eluted with a mixture of ethyl acetate and hexane was dissolved in 10 ml of acetic acid, and then 2.0 ml of water were added.

The mixture was stirred at room temperature for 26 hours. The reaction mixture was then diluted with 100 ml of water and extracted six times with ethyl acetate. The combined extracts were washed with a saturated aqueous solution of sodium bicarbonate, dried and concentrated by evaporation under reduced pressure. The residue was subjected to column chromatography through 20 g of silica gel. 0.746 g of the title compound was isolated as a waxy material from the fractions eluted with mixtures of ethyl acetate and hexane ranging from 1:5 to 1:1 by volume.

Nuclear Magnetic Resonance Spectrum (CDCl$_3$) δ ppm: 0.7–1.9 (39H, multiplet); 1.60 (1H, multiplet); 2.30 (3H, singlet); 2.63 (2H, triplet, J=7 Hz); 3.47 (2H, triplet, J=6 Hz); 3.63 (2H, triplet of multiplets, J6 Hz); 3.79 (2H, doublet, J=4.5 Hz); 4.53 (2H, multiplet); 5.13 (1H, multiplet); 5.61 (1H, singlet); 5.67 (1H, singlet).

Mass spectrum (m/e): 564 (M$^+$) and 465 (M$^+$-C$_4$H$_5$NO$_2$).

PREPARATION 38

(2RS)-2-(5-Methyl-3-isoxazolyloxy)-3-(5-pentadecyl-3-isoxazolyloxy)propyl N-[5-(t-butoxycarbonylamino)pentyl]carbamate 13.12 g of 6-aminohexanoic acid and 14 ml of triethylamine were dissolved in a mixture of 90 ml of water and 95 ml of dioxane, and the solution was stirred at 0° C. for 15 minutes. To it was then added dropwise a solution of 24.00 g of di-t-butyl dicarbonate dissolved in 10 ml of dioxane at 0° to 5° C. over a period of 20 minutes. The reaction mixture was then stirred overnight at room temperature. After ethyl acetate had been added to the mixture, the resulting layers of the reaction mixture were separated, and the aqueous layer was adjusted to a pH value of 2.5 by adding 10% w/v aqueous hydrochloric acid. It was extracted twice with ethyl acetate and the combined extracts were washed with water, dried and concentrated by evaporation under reduced pressure, to give 22.21 g of 6-(t-butoxycarbonyl)aminohexanoic acid, as a white solid melting at 37°–38° C.

A solution of 1.388 g of 6-(t-butoxycarbonyl)aminohexanoic acid, 1.651 g of diphenylphosphoryl azide and 1.25 ml of triethylamine dissolved in 40 ml of benzene was heated under reflux for 3 hours. After the mixture had been allowed to cool, it was washed with a saturated aqueous solution of sodium bicarbonate and an aqueous solution of sodium chloride, dried and concentrated by evaporation under reduced pressure. The residue was dissolved in 30 ml of toluene. To the solution were added 0.901 g of (2RS)-1-O-(5-pentadecyl-3-isoxazolyl)-2-O-(5-methyl-3-isoxazolyl)glycerol (prepared as described in Preparation 35) and 1.25 ml of triethylamine, and the mixture was heated on an oil bath kept at 85° C. for 14 hours. After distilling away the solvent by evaporation under reduced pressure, the residue was subjected to column chromatography through 50 g of silica gel. 1.288 g of the title compound was obtained from the fractions eluted with mixtures of hexane and ethyl acetate ranging from 3:1 to 2:1 by volume, as white crystals melting at 86°–87° C. (from a mixture of hexane and methylene chloride).

Nuclear Magnetic Resonance Spectrum (CDCl$_3$) δ ppm: 0.75–2.00 (35H, multiplet); 1.43 (9H, singlet); 2.30 (3H, singlet); 2.61 (2H, triplet, J=7.5 Hz); 3.12 (4H, multiplet); 4.25–5.0 (6H, multiplet); 5.20 (1H, multiplet); 5.62 (1H, singlet); 5.66 (1H, singlet).

Infrared Absorption Spectrum ν$_{max}$cm$^{-1}$: 3450 and 1715.

Mass Spectrum (m/e): 678 (M$^+$) and 605 [M$^+$—OC(CH$_3$)$_3$].

Elemental analysis: Calculated for C$_{36}$H$_{62}$N$_4$O$_8$: C, 63.68%; H, 9.20%; N, 8.25%. Found: C, 63.62%; H, 9.13%; N, 8.12%.

PREPARATION 39

5-(2-Methoxyethoxy)methoxy-1-pentanol

A solution of 50.00 g of 1,5-pentanediol dissolved in 100 ml of dimethylformamide was added dropwise to a mixture of 23.00 g of sodium hydride (as a 55% w/w dispersion in mine al oil) in 300 ml of dimethylformamide, whilst ice-cooling at 5° to 7° C. The mixture was stirred at room temperature for one hour, after which 65.79 g of 2-methoxyethoxymethyl chloride dissolved in 100 ml of dimethylformamide were added dropwise, whilst ice-cooling at 5° to 7° C. The mixture was stirred at room temperature for 3 hours, after which it was poured into 2.5 liters of water and then extracted five times with methylene chloride. The combined extracts were washed with water, dried and concentrated by evaporation under reduced pressure. The residue was subjected to column chromatography through 850 g of silica gel and 48.40 g of the title compound were obtained from the fractions eluted with a mixtures of methylene chloride and methanol ranging from 98:2 to 95:5 by volume, as a colorless oil.

Nuclear Magnetic Resonance Spectrum (CDCl$_3$) δ ppm: 1.3–1.8 (7H, multiplet); 3.39 (3H, singlet); 3.4–3.8 (8H, multiplet); 4.72 (2H, singlet).

Infrared Absorption Spectrum ν$_{max}$cm$^{-1}$: 3480 (—OH) and 1050 (C—O—C).

Mass Spectrum (m/e): 193 (M$^+$+1) and 117 [M$^+$—C$_3$H$_7$O$_2$].

Elemental analysis: Calculated for C$_9$H$_{20}$O$_4$: C, 56.23%; H,10.49%. Found: C, 55.95%; H, 10.28%.

PREPARATION 40

1-Bromo-5-(2-methoxyethoxy)methoxypentane

To a solution of 48.40 g of 5-(2-methoxyethoxy)methoxy-1-pentanol (prepared as described in Preparation 39) and 100.19 g of carbon tetrabromide dissolved in 500 ml of methylene chloride was added 79.32 g of triphenylphosphine, whilst ice-cooling (at 5° to 8° C.). The mixture was stirred at room temperature for one hour, after which the solvent was removed by evaporation under reduced pressure. Diethyl ether was then added. The insoluble materials were filtered off and the filtrate was concentrated by evaporation under reduced pressure. The residue was subjected to column chromatography through 850 g of silica gel and 57.87 g of the title compound were obtained from the fractions eluted with a 1:9 by volume mixture of ethyl acetate and hexane, as a colorless oil.

Nuclear Magnetic Resonance Spectrum (CDCl$_3$) δ ppm: 1.4–1.8 (4H, multiplet); 1.90 (2H, quintet, J=6.5 Hz); 3.40 (3H, singlet); 3.4–3.8 (8H, multiplet); 4.72 (2H, singlet).

Infrared Absorption Spectrum ν$_{max}$cm$^{-1}$: 1045 (C—O—C) and 565 (—Br).

Mass Spectrum (m/e): 225, 223 (M$^+$—OCH$_3$), 181 and 179 (M$^+$—OCH$_2$CH$_2$OCH$_3$).

Elemental analysis: Calculated for C$_9$H$_{19}$BrO$_3$: C, 42.37%; H, 7.51%; Br, 31.32%. Found: C, 42.39%; H, 7.31%; Br, 31.13%.

PREPARATION 41

Diethyl 2-[5-(2-methoxyethoxy)methoxypentyl]malonate

A solution of 37.80 of diethyl malonate dissolved in 20 ml of absolute ethanol was added dropwise to a solution of sodium ethoxide prepared by gradually adding 3.00 g of metallic sodium to 30 ml of absolute ethanol. To the mixture was added a solution of 30.01 g of 1-bromo-5-(2-methoxyethoxy)methoxypentane (prepared as described in Preparation 40) dissolved in 10 ml of absolute ethanol. The mixture was heated under reflux for 21 hours, after which it was allowed to cool, and then the solvent was distilled off. The residue was mixed with water, and the mixture was extracted three times with ethyl acetate. The combined extracts were washed with water, dried and concentrated by evaporation under reduced pressure. The residue was subjected to column chromatography through 850 g of silica gel, and 32.78 g of the title compound was obtained from the fractions eluted with a 4:1 by volume mixture of hexane and ethyl acetate, as a colorless oil.

Nuclear Magnetic Resonance Spectrum (CDCl$_3$) δ ppm: 1.26 (6H, triplet, J=7.0 Hz); 1.3–2.1 (8H, multiplet); 3.2–3.8 (7H, multiplet); 3.40 (3H, singlet); 4.20 (4H, quartet, J=7.0 Hz); 4.71 (2H, singlet).

Infrared Absorption Spectrum $\nu_{max}$cm$^{-1}$: 1725 (C—O—C) and 1040 (—C—O—C).

Mass Spectrum (m/e): 275 (M$^+$—C$_3$H$_7$O) and 259 (M$^+$—C$_3$H$_7$O$_2$).

Elemental analysis: Calculated for C$_{16}$H$_{30}$O$_7$: C, 57.47%; H, 9.04%. Found: C, 57.56%; H, 8.98%.

PREPARATION 42

2-Hydroxymethyl-7-(2-methoxyethoxy)methoxy-1-heptanol

A solution of 10.29 g of diethyl 2-[5-(2-methoxyethoxy)methoxypentyl]malonate (prepared as described in Preparation 41) dissolved in 100 ml of tetrahydrofuran was added dropwise to 2.40 g of lithium aluminum hydride dispersed in 100 ml of tetrahydrofuran, whilst ice-cooling (at 5° to 7° C.). The mixture was stirred at room temperature for 3 hours, and then 9.60 ml of a 4% w/v aqueous solution of sodium hydroxide was added dropwise at 5° to 9° C. After stirring the mixture for 30 minutes at room temperature, it was filtered with a Celite filter aid, and the filtrate was concentrated by evaporation under reduced pressure. The residue was subjected to column chromatography through 105 g of silica gel and 6.94 g of the title compound were obtained from the fractions eluted with mixtures of methylene chloride and methanol ranging from 98:2 to 95:5 by volume, as a colorless oil.

Nuclear Magnetic Resonance Spectrum (CDCl$_3$) δ ppm: 1.2–2.0 (9H, multiplet); 2.52 (2H, multiplet); 3.40 (3H, singlet); 3.5–4.0 (10H, multiplet); 4.71 (2H, singlet).

Infrared Absorption Spectrum $\nu_{max}$cm$^{-1}$: 3420 (OH) and 1040 (C—O—C—).

Mass Spectrum (m/e): 251 (M$^+$+1).

Elemental analysis: Calculated for C$_{12}$H$_{26}$O$_5$: C, 57.57%; H, 10.47%. Found: C, 57.46%; H, 10.22%.

PREPARATION 43

(2RS)-2-Benzyloxymethyl-7-(2-methoxyethoxy)methoxy-1-heptanol

A solution of 3.06 g of 2-hydroxymethyl-7-(2-methoxyethoxy)methoxy-1-heptanol (prepared as described in Preparation 42) dissolved in 20 ml of dimethylformamide was added dropwise to 587 mg of sodium hydride (as a 55% dispersion in mineral oil) dispersed in 40 ml of dimethylformamide, whilst ice-cooling (at 5° to 7° C.). The mixture was then stirred at room temperature for 1 hour, after which 1.60 ml of benzyl bromide were added dropwise, whilst ice-cooling (at 5° to 7° C.). After stirring the reaction mixture at room temperature for 2 hours, it was poured into 300 ml of water and then extracted five times with ethyl acetate. The combined extracts were washed with water, dried and concentrated by evaporation under reduced pressure. The oily residue was subjected to column chromatography through 60 g of silica gel, and 2.37 g of the title compound were obtained from the fractions eluted with mixtures of hexane and ethyl acetate ranging from 2:1 to 1:1 by volume, as a colorless oil.

Nuclear Magnetic Resonance Spectrum (CDCl$_3$) δ ppm: 1.2–2.0 (9H, multiplet); 2.47 (1H, triplet, J=6 Hz); 3.39 (3H, singlet); 3.4–3.8 (10H, multiplet); 4.52 (2H, singlet); 4.71 (2H, singlet); 7.26 (5H, singlet).

Infrared Absorption Spectrum $\nu_{max}$cm$^{-1}$: 3500 (—OH) and 1040 (C—O—C—).

Mass Spectrum (m/e): 341 (M$^+$+1).

Elemental analysis: Calculated for C$_{19}$H$_{32}$O$_5$: C, 67.03%; H, 9.47%. Found: C, 66.88%; H, 9.39%.

PREPARATION 44

(2RS)-3-O-[(2RS)-2-Benzyloxymethyl-7-hydroxyheptyl]-2-O-(5-methyl-3-isoxazolyl)-1-O-(5-pentadecyl-3-isoxazolyl)glycerol Following a similar procedure to that described in Preparation 2(a), 0.340 g of (2RS)-2-benzyloxymethyl-7-(2-methoxyethoxy)methoxy-1-heptanol (prepared as described in Preparation 43) was converted to 0.42 g of the corresponding crude methanesulfonate.

A solution of 0.300 g of (2RS)-1-O-(5-pentadecyl-3-isoxazolyl)-2-O-(5-methyl-3-isoxazolyl)glycerol (prepared as described in Preparation 35) dissolved in 3 ml of dimethylformamide was added to 0.044 g of sodium hydride suspended in 2 ml of dimethylformamide, whilst ice-cooling. The mixture was stirred at room temperature for one hour, after which a solution of the said methanesulfonate dissolved in 3 ml of dimethylformamide was added to it, followed by heating on an oil bath kept at 50° C. for 65 hours. After it had been allowed to cool, the reaction mixture was poured into 100 ml of water and then extracted twice with ethyl acetate. The combined extracts were washed with water, dried and concentrated by evaporation under reduced pressure. The residue was subjected to column chromatography through 10 g of silica gel. Concentration of the fractions eluted with mixtures of hexane and ethyl acetate ranging from 9:1 to 4:1 by volume afforded an oily material (0.343 g), which had an Rf value of 0.71 on thin-layer chromatography on silica gel (developing solvent: a 1:1 by volume mixture of hexane and ethyl acetate; visualization with iodine).

To a solution of the oily material dissolved in 7 ml of methanol was added 1.75 ml of concentrated hydrochloric acid and the mixture was heated for 2 hours at 50° C. on an oil bath. After cooling, it was poured into 100 ml of water and then extracted twice with ethyl acetate. The combined extracts were washed with a saturated aqueous solution of sodium bicarbonate and with water, dried and concentrated by evaporation under reduced pressure. The residue was purified by medium pressure liquid chromatography using a Lobar B Column. 0.216 of the title compound was obtained from the fractions eluted with a 3:1 by volume mixture of hexane and ethyl acetate, as an oil.

Nuclear Magnetic Resonance Spectrum (CDCl$_3$) δ ppm: 0.7–2.05 (38H, multiplet); 2.30 (9H, singlet); 2.60 (3H, triplet. J=7 Hz); 3.3–3.9 (6H, multiplet); 4.2–4.6 (3H, multiplet); 4.45 (2H, singlet); 5.10 (1H, multiplet); 5.60 (2H, multiplet); 7.31 (5H, singlet).

Mass Spectrum (m/e): 684 (M+), 593 and 494.

PREPARATION 45

(2RS)-3-O-[(2RS)-3-Benzyloxymethyl-7-iodoheptyl]-2-O-(5-methyl-3-isoxazolyl)-1-O-(5-centadecyl-3-isoxazolyl)glycerol Following a similar procedure to that described in Preparation 2(a), 0.209 g of (2RS)-3-O-[(2RS)-2-benzyloxymethyl-7-hydroxyheptyl]-2-O-(5-methyl-3-isoxazolyl)-1-O-(5-pentaldecyl-3-isoxazolyl)glycerol (prepared as described in Preparation 44) was converted to 0.24 g of the corresponding crude methanesulfonate. A mixture of the methanesulfonate, sodium iodide (0.227 g) and acetone (6 ml) was heated under reflux for 17 hours. After insoluble materials were filtered off, the solvent was distilled off and the residue was dissolved in ethyl acetate. The solution was washed with a 10% w/v aqueous solution of sodium thiosulfate and with water, and then the solvent was removed by evaporation under reduced pressure. The residue was subjected to column chromatography through silica gel (5 g) and the title compound (0.245 g) was obtained as an oil from the fractions eluted with a 19:1 by volume mixture of hexane and ethyl acetate.

Nuclear Magnetic Resonance Spectrum (CDCl$_3$) δ ppm: 0.7–2.1 (38H, multiplet); 2.28 (3H, singlet); 2.60 (2H, triplet, J=7 Hz); 3.13 (2H, triplet, J=7 Hz); 3.3–4.0 (6H, multiplet); 4.1–4.7 (2H, multiplet); 4.45 (2H, singlet); 5.20 (1H, multiplet); 5.60 (2H, multiplet); 7.30 (5H, singlet).

Mass Spectrum (m/e): 794 (M+), 703, 696 and 668.

PREPARATION 46

(2RS)-7-Iodo-2-[(2RS)-2-(5-methyl-3-isoxazolyloxy)-3-(5-pentadecyl-3-isoxazolyloxy)propoxy]methyl-1-heptanol To a mixture of acetonitrile (6 ml) and methylene chloride (3 ml) cooled with ice were added aluminum chloride (0.260 g), sodium iodide (0.292 g) and a solution of 0.155 g of (2RS)-3-O-[(2RS)-3-benzyloxymethyl-7-iodoheptyl]-2-O-(5-methyl-3-isoxazolyl)-1-O-(5-pentadecyl-3-isoxazolyl)glycerol (prepared as described in Preparation 45) in 20 ml of methylene chloride, in that order. The mixture was stirred at 0° C. for 3 hours and then at room temperature for 3 hours, after which it was poured into water (60 ml), and then extracted twice with ethyl acetate. The combined extracts were washed with a 10% w/v aqueous solution of sodium thiosulfate and with water, dried and concentrated by evaporation under reduced pressure. The residue was subjected to column chromatography through silica gel (4 g), and the title compound (0.114 g) was obtained from the fractions eluted with a 9:1 to 4:1 by volume mixture of hexane and ethyl acetate as an oil.

Nuclear Magnetic Resonance Spectrum (CDCl$_3$) δ ppm: 0.7–2.1 (38H, multiplet); 2.32 (3H, singlet); 2.60 (3H, triplet, J=7 Hz); 2.73 (1H, singlet); 3.16 (2H, triplet, J=7 Hz); 3.45–3.95 (6H, multiplet); 4.1–4.8 (2H, multiplet); 5.15 (1H, multiplet); 5.63 (2H, multiplet).

PREPARATION 47

(2RS)-7-Iodo-2-(2RS)-2-(5-methyl-3-isoxazolyloxy)-3-(5-pentadecyl-3-isoxazolyloxy)propoxy]methylheptanoic acid To a solution of 0.114 g of (2RS)-7-iodo-2-[(2RS)-2-(5-methyl-3-isoxazolyloxy)-3-(5-pentadecyl-3-isoxazolyloxy)propoxy]methyl-1-heptanol (prepared as described in Preparation 46) dissolved in 2 ml of acetone was added Jones' reagent (0.12 ml; each ml contained 0.267 g of chromic anhydride), whilst ice-cooling. After stirring for 1 hour whilst ice-cooling, the reaction mixture was poured into water (20 ml), and then extracted four times with ethyl acetate. The combined extracts were washed with water, dried and concentrated by evaporation under reduced pressure. The residue was subjected to column chromatography through silica gel (1 g) and the title compound (0.105 g) was obtained, as an oil, from the fractions eluted with mixtures of hexane and ethyl acetate ranging from 9:1 to 4:1 by volume.

Nuclear Magnetic Resonance Spectrum (CDCl$_3$) δ ppm: 0.7–2.1 (37H, multiplet); 2.32 (3H, singlet); 2.4–2.9 (3H, multiplet); 3.18 (3H, triplet, J=7 Hz); 3.45–4.1 (4H, multiplet); 4.2–4.8 (2H, multiplet); 5.11 (1H, multiplet); 5.65 (2H, multiplet).

Infrared Absorption Spectrum $v_{max}$cm$^{-1}$: 3600–2400 and 1710.

PREPARATION 48

Ethyl hydrogen 2-[5-(2-methoxyethoxy)methoxypentyl]malonate

To a solution of 1.029 g of diethyl 2-[5-(2-methoxyethoxy)methoxypentyl]malonate (prepared as described in Preparation 41) dissolved in ethanol (1.5 ml) was added an aqueous solution (1.5 ml) containing potassium hydroxide (0.203 g) whilst ice-cooling. The reaction mixture was stirred at room temperature for 5 hours, after which it was washed with diethyl ether. The aqueous layer was adjusted to a pH value of 2 by adding 10% aqueous hydrochloric acid, and it was then extracted four times with methylene chloride. The combined extracts were dried and concentrated by evaporation under reduced pressure. The oily residue (0.94 g) was subjected to column chromatography through silica gel (20 g) and the title compound (0.764 g) Was obtained, as a colorless oil, from the fractions eluted with mixtures of hexane and ethyl acetate ranging from 2:1 to 1:1 by volume.

Nuclear Magnetic Resonance Spectrum (CDCl$_3$) δ ppm: 1.28 (3H, triplet, J=7 Hz); 1.15–2.10 (8H, multiplet); 3.25–3.80 (7H, multiplet); 3.42 (3H, singlet); 4.24 (2H, quartet, J=7 Hz); 4.73 (2H, singlet).

Elemental analysis: Calculated for $C_{14}H_{26}O_7$: C, 54.88%; H, 8.55%. Found: C, 54.70%; H, 8.45%.

PREPARATION 49

(2RS)-3-(5-Hexadecyl-3-isoxazolyloxy)-2-(3-isoxazolyloxy)propyl N-[(1RS)-1-ethoxycarbonyl-6-(2-methoxyethoxy)methoxy]hexylcarbamate A solution of 0.306 g of ethyl hydrogen 2-[5-(2-methoxyethoxy)methoxypentyl]malonate (prepared as described in Preparation 48), diphenylphosphoryl azide (0.275 g) and triethylamine (0.21 ml) dissolved in benzene (7 ml) was heated for 4.5 hours under reflux. After cooling, the reaction mixture was successively washed with a saturated aqueous solution of sodium bicarbonate and with water, dried and concentrated by evaporation under reduced pressure. The residue, 0.150 g of (2RS)-1-O-(5-hexadecyl-3-isoxazolyl)-2-O-(3-isoxazolyl)-glycerol (prepared as described in Preparation 33) and triethylamine (0.21 ml) were dissolved in toluene (7 ml) and the solution was heated on an oil bath kept at 85° C. for 16 hours. Ater allowing it to cool, the solvent was removed by evaporation under reduced pressure, and the residue was subjected to column chromatography through silica gel (5 g). The title compound (0.257 g) was obtained, as a viscous oil, from the fractions eluted with mixtures of hexane and diethyl ether ranging from 1:1 to 1:2 by volume.

Nuclear Magnetic Resonance spectrum (CDCl$_3$) δ ppm: 0.7–2.0 (42H, multiplet); 2.62 (2H, triplet, J=7 Hz); 3.39 (3H, singlet); 3.4–3.85 (6H, multiplet); 4.18 (2H, quartet, J=7 Hz); 4.1–4.6 (5H, multiplet); 4.70 (2H, singlet); 5.27 (2H, multiplet); 5.63 (1H, singlet); 6.03 (1H, doublet, J=2 Hz); 8.17 (1H, doublet, J=2 Hz).

PREPARATION 50

(2RS)-3-(5-Hexadecyl-3-isoxazolyloxy)-2-(3-isoxazolyloxy)propyl N-[(1RS)-1-ethoxycarbonyl-6-hydroxy]hexylcarbamate To a solution of 0.255 g of (2RS)-3-(5-hexadecyl-3-isoxazolyloxy)-2-(3-isoxazolyloxy)propyl N-[(1RS)-1-ethoxycarbonyl-6-(2-methoxyethoxy)methoxy]hexylcarbamate (prepared as described in Preparation 49) dissolved in 5 ml of absolute ethanol was added acetyl chloride (0.1 ml), whilst ice-cooling. The reaction mixture was stirred at room temperature for 4 hours, after which it was diluted with ethyl acetate (25 ml) and then washed with a saturated aqueous solution of sodium bicarbonate and with water. After drying, the solvent was removed by evaporation under reduced pressure, and the residue was subjected to column chromatography through silica gel (4 g). The title compound (0.211 g) was obtained from the fractions eluted with a 2:1 by volume mixture of hexane and ethyl acetate as an oil.

Nuclear Magnetic Resonance Spectrum (CDCl$_3$) δ ppm: 0.8–2.0 (42H, multiplet); 2.30 (1H, singlet): 2.61 (2H, triplet, J=7 Hz); 3.60 (2H, multiplet); 4.16 (2H, quartet, J=7 Hz): 4.3–4.8 (5H, multiplet); 5.21 (1H, multiplet); 5.51 (1H, multiplet); 5.59 (1H, doublet, J=2 Hz); 5.60 (1H, singlet); 8.14 (1H, doublet, J=2 Hz).

EXPERIMENT 1

Inhibition of PAF-induced hypotension

The test animals employed were rats of the Wistar-Imamichi strain, each weighing between 350 and 450 g.

Under Inactin anesthesia (90 mg/kg administered intraperitoneally) the left femoral artery and vein of each test animal were cannulated to enable the arterial blood pressure to be monitored continuously and for drug administration, respectively. At intervals of about 5 minutes, each animal was given by intravenous injection 10 ng/kg of synthetic 1-C$_{16:0}$ PAF until a steady hypotensive response was achieved. At this time, the drug to be tested was administered by intravenous injection in doses increasing cumulatively by a factor of 3. Within 1 minute of this injection, a further 10 ng/kg of the 1-C$_{16:0}$ PAF was administered. The hypotensive response to PAF was inhibited by the test drug in a dose-related manner.

The PAF was administered in the form of a solution in physiological saline containing 0.25% w/v bovine serum albumin. The test drugs were dissolved in physiological saline containing either 0.25% w/v BSA or 20% v/v ethanol.

The 50% inhibitory dose (ID$_{50}$) was calculated from the dose-response curve constructed for the inhibition of PAF-induced hypotension.

This test was carried out using compounds of the invention, as well as the prior art compound CV-3988, disclosed in U.S. Pat. No. 4,408,052 and represented by the foregoing formula (B). The results are shown in the following Table 6.

EXPERIMENT 2

Inhibition of PAF-induced platelet aggregation in vitro

Blood was drawn from a rabbit and immediately mixed with one nineth of its volume of a 3.8% w/v aqueous solution of sodium citrate. A platelet-rich plasma (PRP) was obtained as a supernatant by centrifugation of the blood at 150×g for 15 minutes at room temperature. The precipitated fraction was centrifuged for a further 15 minutes at 1000×g to obtain a platelet-poor plasma (PPP) as a supernatant. Appropriate proportions of this PRP and PPP were mixed to obtain a plasma having a platelet count of $6 \times 10^5/\mu l$.

Platelet aggregation was determined by the method of Born et al. [G. V. R. Born et al., J. Physiol., 62, 67–68 (1962)] where an increase in light transmission is measured by the aggregometer.

25 μl of a saline solution containing the compound to be tested at an appropriate concentration was added to 250 μl of the above plasma. One minute thereafter. 25 μl of a saline solution of synthetic C$_{16:0}$ PAF (at a concentration sufficient to give a final concentration of $1 \times 10^{-8} - 3 \times 10^{-8}$M) was added and aggregation was observed for 5 minutes. The aggregation resulting from the addition of PAF alone, without the prior addition of the test compound was taken as 100%.

The IC$_{50}$ values (i.e. concentrations to inhibit aggregation by 50%) were calculated from dose-response curves and are shown in Table 6.

TABLE 6

| Test compound | Inhibition of Hypotension ID$_{50}$ (mg/kg) | Inhibition of Platelet aggregation IC$_{50}$ (M) |
| --- | --- | --- |
| Cpd. of Ex. 13 | 0.096 | $3.4 \times 10^{-6}$ |
| Cpd. of Ex. 18 | 0.081 | $4.8 \times 10^{-6}$ |
| Cpd. of Ex. 23 | 0.067 | $1.4 \times 10^{-6}$ |
| Cpd. of Ex. 24 | 0.030 | $3.1 \times 10^{-7}$ |
| Cpd. of Ex. 25 | 0.055 | $2.7 \times 10^{-7}$ |
| Cpd. of Ex. 33 | 0.086 | $3.1 \times 10^{-7}$ |
| Cpd. of Ex. 38 | 0.004 | $8.1 \times 10^{-8}$ |
| Cpd. of Ex. 41 | 0.054 | $3.5 \times 10^{-7}$ |
| CV - 3988 | 0.415 | $9.8 \times 10^{-6}$ |

We claim:

1. A compound of formula (I):

in which:

R$^1$ represents an alkylcarbamoyl group in which the alkyl part is C$_8$–C$_{22}$;

R² represents unsubstituted 3-isoxazolyl or 3-isoxazolyl substituted by $C_1$-$C_6$-alkyl, $C_1$-$C_6$-aliphatic acyl, aromatic acyl, aryl or $C_7$-$C_{14}$-aralkyl;

Y represents a group of formula —X—P(O)(OH)—O—, where:
X represents an oxygen atom;
D represents a $C_1$-$C_{14}$ alkylene group;
Q represents unsubstituted thiazolyl, unsubstituted pyridyl or thiazolyl or pyridyl substituted with $C_1$-$C_6$ alkyl groups, $C_1$-$C_6$ alkoxy groups, carbamoyl groups, halogen atoms or $C_1$-$C_6$ hydroxyalkyl groups;

and pharmaceutically acceptable salts, esters and amides thereof.

2. A compound as claimed in claim 1, wherein:
R¹ represents an alkylcarbamoyl group in which the alkyl part is $C_8$-$C_{22}$;
R² represents unsubstituted 3-isoxazolyl or 3-isoxazolyl substituted by $C_1$-$C_6$ alkyl, $C_1$-$C_6$-aliphatic acyl, or aryl;
Y represents a group of formula

—X—P(O)(OH)—O—;

where:
X represents an oxygen atom;
D represents a $C_1$-$C_{10}$ alkylene group;
Q represents
unsubstituted thiazolyl, unsubstituted pyridyl or thiazolyl or pyridyl substituted with $C_1$-$C_6$ alkyl groups, $C_1$-$C_6$ alkoxy groups, halogen atoms or $C_1$-$C_6$ hydroxyalkyl groups;

and pharmaceutically acceptable salts, esters and amides thereof.

3. A compound as claimed in claim 2, wherein:
R¹ represents an alkylcarbamoyl group in which the alkyl part is $C_8$-$C_{22}$;
R² represents unsubstituted 3-isoxazolyl or 3-isoxazolyl substituted by $C_1$-$C_6$-alkyl, or aryl;
Y represents a group of formula

—X—P(O)(OH)—O—, where:
X represents an oxygen atom;
D represents a $C_1$-$C_{10}$ alkylene group
Q represents substituted thiazolyl, unsubstituted pyridyl or thiazolyl or pyridyl substituted with $C_1$-$C_6$ alkyl groups or $C_1$-$C_6$ hydroxyalkyl groups;
and pharmaceutically acceptable salts, esters and amides thereof.

4. A compound as claimed in claim 3, wherein:
R¹ represents an alkylcarbamoyl group in which the alkyl part is $C_8$-$C_{22}$;
R² represents unsubstituted 3-isoxazolyl or 3-isoxazolyl substituted by $C_1$-$C_6$-alkyl, or aryl;
Y represents a group of formula

—X—P(O)(OH)—O—, where:

X represents an oxygen atom;
D represents a $C_1$-$C_8$ alkylene group;
Q represents unsubstituted thiazolyl, unsubstituted pyridyl, thiazolyl substituted with $C_1$-$C_6$ alkyl groups, or pyridyl substituted with $C_1$-$C_6$ alkyl groups;

and pharmaceutically acceptable salts, esters and amides thereof.

5. A compound as claimed in claim 1, which is 3-(5-pentadecyl-3-isoxazolyloxy)-2-(5-methyl-3-isoxazolyloxy)propyl 6-thiazoliohexyl phosphate inner salt.

6. A compound as claimed in claim 1, which is 3-(N-heptadecylcarbamoyloxy)-2-(5-methyl-3-isoxazolyloxy)propyl 2-thiazolioethyl phosphate inner salt.

7. A compound as claimed in claim 1, which is 3-(N-heptadecylcarbamoyloxy)-2-(3-isoxazolyloxy)propyl 2-thiazolioethyl phosphate inner salt.

8. The compound of claim 1 wherein R¹ represents $C_8$-$C_{22}$ alkyl carbamoyl; R² represents 3-isoxazolyl Y represents (—OPO—O) anion
 |
 O—

D represents —C(CH₂)—; Q represents ethylthiazolyl-3 cation.

9. The compound as claimed in claim 1, wherein R² is unsubstituted 3-isoxazolyl or 3-isoxazolyl substituted by $C_1$-$C_6$ alkyl.

10. The compound as claimed in claim 2, wherein R² is unsubstituted 3-isoaxazolyl or 3-isoxazolyl substituted by $C_1$-$C_6$ alkyl.

11. The compound as claimed in claim 3, wherein R² is unsubstituted 3-isoaxazolyl or 3-isoxazolyl substituted by $C_1$-$C_6$ alkyl.

12. The compound as claimed in claim 4 wherein R² is unsubstituted 3-isoaxazolyl or 3-isoxazolyl substituted by $C_1$-$C_6$ alkyl.

13. The compound as claimed in claim 1, wherein R² is unsubstituted 3-isoxazolyl or 3-isoxazolyl substituted by a $C_1$-$C_6$ alkyl selected from the group consisting of methyl, ethyl, propyl, isopropyl, butyl, sec-butyl, t-butyl, pentyl, isopentyl, 2-methylbutyl, neopentyl, hexyl, 4-methylpentyl, 3-methylpentyl, 2-methylpentyl, 3,3-dimethylbutyl, 2,2-dimethylbutyl, 1,1-dimethylbutyl, 1,2-dimethylbutyl, 1,3-dimethylbutyl and 2,3-dimethylbutyl, a $C_1$-$C_6$ aliphatic acyl selected from the group consisting of formyl, acetyl, chloroacetyl, dichloroacetyl, trichloroacetyl, trifluoroacetyl, methoxyacetyl, propionyl, butyryl, (E)-2-methyl-2-butenoyl, isobutyryl, pentanoyl and pivaloyl; an aromatic acyl selected from the group consisting of benzoyl, o-(dibromomethyl)benzoyl, o-methoxycarbonyl) benzoyl, p-phenylbenzoyl, 2,4,6-trimethylbenzoyl, p-toluoyl, p-anisoyl, p-chlorobenzyl, p-nitrobenzoyl, o-nitrobenzoyl, 1-naphthoyl and 2-naphthoyl; an aryl selected from the group consisting of phenyl, tolyl, xylyl and naphthyl; or a $C_7$-$C_{14}$ aralkyl selected from the group consisting of benzyl, phenethyl, phenylpropyl, 1-naphthylmethyl and 2-naphthylmethyl.

* * * * *

UNITED STATES PATENT AND TRADEMARK OFFICE
CERTIFICATE OF CORRECTION

PATENT NO. : 5,068,340
DATED : November 26, 1991
INVENTOR(S) : NAKAMURA et al

It is certified that error appears in the above-identified patent and that said Letters Patent is hereby corrected as shown below:

Column 9, line 51, "substituents (a')" should be a separate line.

Column 26, line 34, delete "Period", and insert --period--.

Signed and Sealed this

Thirtieth Day of August, 1994

Attest:

BRUCE LEHMAN

Attesting Officer      Commissioner of Patents and Trademarks